US008911786B2

(12) United States Patent
Desai et al.

(10) Patent No.: US 8,911,786 B2
(45) Date of Patent: Dec. 16, 2014

(54) NANOPARTICLE COMPRISING RAPAMYCIN AND ALBUMIN AS ANTICANCER AGENT

(75) Inventors: Neil P. Desai, Los Angeles, CA (US); Patrick Soon-Shiong, Los Angeles, CA (US); Vuong Trieu, Calabasas, CA (US)

(73) Assignee: Abraxis Bioscience, LLC, Los Angeles, CA (US)

( * ) Notice: Subject to any disclaimer, the term of this patent is extended or adjusted under 35 U.S.C. 154(b) by 344 days.

(21) Appl. No.: 12/530,188

(22) PCT Filed: Mar. 7, 2008

(86) PCT No.: PCT/US2008/003096
§ 371 (c)(1),
(2), (4) Date: Mar. 4, 2010

(87) PCT Pub. No.: WO2008/109163
PCT Pub. Date: Sep. 12, 2008

(65) Prior Publication Data
US 2010/0183728 A1    Jul. 22, 2010

Related U.S. Application Data

(60) Provisional application No. 60/905,669, filed on Mar. 7, 2007, provisional application No. 60/905,734, filed on Mar. 7, 2007, provisional application No. 60/905,662, filed on Mar. 7, 2007, provisional application No. 60/905,735, filed on Mar. 7, 2007, provisional application No. 60/905,672, filed on Mar. 7, 2007, provisional application No. 60/905,787, filed on Mar. 7, 2007, provisional application No. 60/905,663, filed on Mar. 7, 2007, provisional application No. 60/905,767, filed on Mar. 7, 2007, provisional application No. 60/905,750, filed on Mar. 7, 2007, provisional application No. 60/923,248, filed on Apr. 13, 2007, provisional application No. 60/923,456, filed on Apr. 13, 2007.

(51) Int. Cl.
| | | |
|---|---|---|
| *A61K 9/50* | (2006.01) | |
| *A61K 31/675* | (2006.01) | |
| *A61K 9/00* | (2006.01) | |
| *A61K 9/19* | (2006.01) | |
| *A61K 9/51* | (2006.01) | |
| *A61K 31/436* | (2006.01) | |
| *A61K 31/517* | (2006.01) | |
| *A61K 31/685* | (2006.01) | |
| *A61K 45/06* | (2006.01) | |
| *A61K 47/42* | (2006.01) | |
| *A61N 5/10* | (2006.01) | |
| *A61N 7/00* | (2006.01) | |

(52) U.S. Cl.
CPC ............. *A61K 31/675* (2013.01); *A61K 9/0019* (2013.01); *A61K 9/19* (2013.01); *A61K 9/5169* (2013.01); *A61K 31/436* (2013.01); *A61K 31/517* (2013.01); *A61K 31/685* (2013.01); *A61K 45/06* (2013.01); *A61K 47/42* (2013.01); *A61N 5/10* (2013.01); *A61N 7/00* (2013.01)
USPC ............ 424/491; 424/489; 424/490; 424/500

(58) Field of Classification Search
USPC .......... 424/465–489, 490, 491, 500; 514/19.3
See application file for complete search history.

(56) References Cited

U.S. PATENT DOCUMENTS

| | | | |
|---|---|---|---|
| 5,206,018 A * | 4/1993 | Sehgal et al. ................. 424/122 |
| 5,362,478 A | 11/1994 | Desai et al. |
| 5,439,686 A | 8/1995 | Desai et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,540,931 A | 7/1996 | Hewitt et al. |
| 5,560,933 A | 10/1996 | Soon-Shiong et al. |
| 5,635,207 A | 6/1997 | Grinstaff et al. |
| 5,639,473 A | 6/1997 | Grinstaff et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,916,596 A | 6/1999 | Desai et al. |

(Continued)

FOREIGN PATENT DOCUMENTS

| | | |
|---|---|---|
| EP | 1 683 517 A1 | 7/2006 |
| JP | 2004-525950 A | 8/2004 |

(Continued)

OTHER PUBLICATIONS

Adnot, S. et al. (Jan. 1991). "Loss of Endothelium-Dependent Relaxant Activity in the Pulmonary Circulation of Rats Exposed to Chronic Hypoxia," *J. Clin. Invest.* 87(1):155-162.

(Continued)

*Primary Examiner* — Michael G. Hartley
*Assistant Examiner* — Micah-Paul Young
(74) *Attorney, Agent, or Firm* — Morrison & Foerster LLP

(57) ABSTRACT

The present invention features methods for treating, stabilizing, preventing, and/or delaying cancer by administering nanoparticles that comprise rapamycin or a derivative thereof. The invention also provides compositions (e.g., unit dosage forms) comprising nanoparticles that comprise a carrier protein and rapamycin or a derivative thereof. The invention further provides combination therapy methods of treating cancer comprising administering to an individual an effective amount of nanoparticles that comprise rapamycin or a derivative thereof and a second therapy.

37 Claims, 7 Drawing Sheets

(56) References Cited

U.S. PATENT DOCUMENTS

| | | | |
|---|---|---|---|
| 5,997,904 A | 12/1999 | Magdassi et al. | |
| 6,096,331 A | 8/2000 | Desai et al. | |
| 6,506,405 B1 | 1/2003 | Desai et al. | |
| 6,528,067 B1 | 3/2003 | Magdassi et al. | |
| 6,537,579 B1 | 3/2003 | Desai et al. | |
| 6,652,884 B2 | 11/2003 | Falciani | |
| 6,749,868 B1 | 6/2004 | Desai et al. | |
| 6,753,006 B1 | 6/2004 | Desai et al. | |
| 7,771,751 B2 | 8/2010 | Desai et al. | |
| 7,820,788 B2 | 10/2010 | Desai et al. | |
| 7,923,536 B2 | 4/2011 | Desai et al. | |
| 7,981,445 B2 | 7/2011 | De et al. | |
| 8,034,375 B2 | 10/2011 | Desai et al. | |
| 8,034,765 B2 | 10/2011 | De et al. | |
| 8,137,684 B2 | 3/2012 | Desai et al. | |
| 8,138,229 B2 | 3/2012 | Desai et al. | |
| 8,257,733 B2 | 9/2012 | Desai et al. | |
| 8,268,348 B2 | 9/2012 | Desai et al. | |
| 8,314,156 B2 | 11/2012 | Desai et al. | |
| 2003/0054042 A1 | 3/2003 | Liversidge et al. | |
| 2003/0199425 A1 | 10/2003 | Desai et al. | |
| 2004/0126400 A1* | 7/2004 | Iversen et al. | 424/400 |
| 2005/0004002 A1* | 1/2005 | Desai et al. | 514/2 |
| 2005/0038498 A1 | 2/2005 | Dubrow et al. | |
| 2005/0119330 A1 | 6/2005 | Kao et al. | |
| 2005/0152979 A1 | 7/2005 | Besman et al. | |
| 2005/0203013 A1 | 9/2005 | Soker et al. | |
| 2005/0209266 A1 | 9/2005 | Garvey | |
| 2005/0244339 A1 | 11/2005 | Jauernigh et al. | |
| 2006/0073182 A1* | 4/2006 | Wong et al. | 424/426 |
| 2006/0210638 A1 | 9/2006 | Liversidge et al. | |
| 2007/0066522 A1* | 3/2007 | McCormick et al. | 514/12 |
| 2007/0087022 A1 | 4/2007 | Desai et al. | |
| 2007/0092563 A1 | 4/2007 | Desai et al. | |
| 2007/0093547 A1 | 4/2007 | Desai et al. | |
| 2007/0116774 A1 | 5/2007 | Desai et al. | |
| 2007/0117744 A1* | 5/2007 | Desai et al. | 514/11 |
| 2007/0129448 A1 | 6/2007 | Desai et al. | |
| 2007/0166388 A1 | 7/2007 | Desai et al. | |
| 2008/0063724 A1 | 3/2008 | Desai et al. | |
| 2008/0153738 A1 | 6/2008 | Desai et al. | |
| 2008/0161382 A1 | 7/2008 | Desai et al. | |
| 2008/0213370 A1 | 9/2008 | Desai et al. | |
| 2008/0280939 A1 | 11/2008 | Izumo et al. | |
| 2008/0280987 A1 | 11/2008 | Desai et al. | |
| 2009/0098210 A1 | 4/2009 | Desai et al. | |
| 2009/0175951 A1 | 7/2009 | Liversidge | |
| 2009/0263483 A1 | 10/2009 | Desai et al. | |
| 2009/0304805 A1 | 12/2009 | Desai et al. | |
| 2010/0035800 A1 | 2/2010 | Desai et al. | |
| 2010/0048499 A1 | 2/2010 | Desai et al. | |
| 2010/0112077 A1 | 5/2010 | Desai et al. | |
| 2010/0166869 A1 | 7/2010 | Desai et al. | |
| 2010/0215751 A1 | 8/2010 | Desai et al. | |
| 2010/0297243 A1 | 11/2010 | Desai et al. | |
| 2011/0052708 A1 | 3/2011 | Soon-Shiong et al. | |
| 2011/0064812 A1 | 3/2011 | Bahl et al. | |
| 2011/0118342 A1 | 5/2011 | De et al. | |
| 2011/0151012 A1 | 6/2011 | Desai et al. | |
| 2011/0165256 A1 | 7/2011 | Desai et al. | |
| 2011/0196026 A1 | 8/2011 | De et al. | |
| 2011/0301248 A1 | 12/2011 | Desai et al. | |
| 2012/0004177 A1 | 1/2012 | Desai et al. | |
| 2012/0070502 A1 | 3/2012 | Desai et al. | |
| 2012/0076862 A1 | 3/2012 | Desai et al. | |
| 2012/0128732 A1 | 5/2012 | Trieu et al. | |
| 2012/0189701 A1 | 7/2012 | Desai et al. | |
| 2012/0231082 A1 | 9/2012 | Desai et al. | |
| 2012/0283205 A1 | 11/2012 | Desai et al. | |
| 2013/0045240 A1 | 2/2013 | Tao et al. | |
| 2013/0071438 A1 | 3/2013 | Desai et al. | |
| 2013/0115296 A1 | 5/2013 | Yeo et al. | |
| 2013/0195922 A1 | 8/2013 | Desai et al. | |
| 2013/0195983 A1 | 8/2013 | Desai et al. | |
| 2013/0195984 A1 | 8/2013 | Desai et al. | |
| 2013/0202709 A1 | 8/2013 | Desai et al. | |
| 2013/0209518 A1 | 8/2013 | Desai et al. | |
| 2013/0244952 A1 | 9/2013 | Desai et al. | |
| 2013/0266659 A1 | 10/2013 | Desai et al. | |
| 2013/0280336 A1 | 10/2013 | Desai et al. | |
| 2013/0280337 A1 | 10/2013 | Desai et al. | |
| 2014/0017315 A1 | 1/2014 | Desai et al. | |
| 2014/0017316 A1 | 1/2014 | Desai et al. | |
| 2014/0017323 A1 | 1/2014 | Desai et al. | |
| 2014/0023717 A1 | 1/2014 | Desai et al. | |
| 2014/0039069 A1 | 2/2014 | Desai et al. | |
| 2014/0039070 A1 | 2/2014 | Desai et al. | |
| 2014/0056986 A1 | 2/2014 | Desai et al. | |
| 2014/0072630 A1 | 3/2014 | Tao et al. | |
| 2014/0072631 A1 | 3/2014 | Trieu et al. | |
| 2014/0072643 A1 | 3/2014 | Desai et al. | |
| 2014/0079787 A1 | 3/2014 | Yeo et al. | |
| 2014/0079788 A1 | 3/2014 | Desai et al. | |
| 2014/0079793 A1 | 3/2014 | Desai et al. | |
| 2014/0080901 A1 | 3/2014 | Desai et al. | |
| 2014/0134257 A1 | 5/2014 | Desai et al. | |

FOREIGN PATENT DOCUMENTS

| | | |
|---|---|---|
| WO | WO-94/18954 A1 | 9/1994 |
| WO | WO-98/14174 A1 | 4/1998 |
| WO | WO-98/14175 A1 | 4/1998 |
| WO | WO-99/00113 A1 | 1/1999 |
| WO | WO-00/64437 A1 | 11/2000 |
| WO | WO-00/71079 A2 | 11/2000 |
| WO | WO-00/71079 A3 | 11/2000 |
| WO | WO-01/89522 A1 | 11/2001 |
| WO | WO-02/080975 A1 | 10/2002 |
| WO | WO-02/087545 A1 | 11/2002 |
| WO | WO-03/096944 A1 | 11/2003 |
| WO | WO-2004/052401 A2 | 6/2004 |
| WO | WO-2004/052401 A3 | 6/2004 |
| WO | WO 2005117952 A2 * | 12/2005 |
| WO | WO-2006/053754 A1 | 5/2006 |
| WO | WO-2006/089207 A2 | 8/2006 |
| WO | WO-2006/089207 A3 | 8/2006 |
| WO | WO-2006/089290 A1 | 8/2006 |
| WO | WO 2006089290 A1 * | 8/2006 |
| WO | WO-2006/124739 A1 | 11/2006 |
| WO | WO-2007/027819 A2 | 3/2007 |
| WO | WO-2007/027941 A2 | 3/2007 |
| WO | WO-2007/027941 A3 | 3/2007 |
| WO | WO-2008/027055 A1 | 3/2008 |
| WO | WO-2008/057562 A1 | 5/2008 |
| WO | WO-2008/076373 A1 | 6/2008 |
| WO | WO-2008/109163 A1 | 9/2008 |
| WO | WO-2008/137148 A2 | 11/2008 |
| WO | WO-2008/137148 A3 | 11/2008 |
| WO | WO-2008/150532 A1 | 12/2008 |

OTHER PUBLICATIONS

Al Housseini, A et al. (Mar. 1, 2008). "A Phase II, Non-Randomized Study of Abraxane plus Carboplatin in Patents With Recurrent Platinum-Sensitive Ovarian or Primary Peritoneal Cancer: Evaluation of the Response and Survival and Progression-Free Survival," *Gynecologic Oncology*, 108(Suppl. 1): S129-S130, Abstract No. 293.

Carmeliet, P. et al. (Sep. 14, 2000). "Angiogenesis in Cancer and Other Diseases," *Nature* 407(6801):249-257.

Carter, D. C. et al. (1994). "Structure of Serum Albumin," *Adv. Protein. Chem.* 45:153-203.

Chauhan, D. et al. (Feb. 1, 1996). "Multiple Myeloma Cell Adhesion-Induced Interleukin-6 Express in Bone Marrow Stromal Cells Involves Activation of NF-Kappa B," *Blood* 87(3):1104-1112.

Curry, S. et al. (Sep. 1998). "Crystal Structure of Human Serum Albumin Complexed with Fatty Acid Reveals an Asymmetric Distribution of Binding Sites," *Nat. Struct. Biol.* 5(9):827-835.

Curry, S. et al. (1999). "Fatty Acid Binding to Human Serum Albumin: New Insights from Crystallographic Studies," *Biochim. Biophys. Acta* 1441:131-140.

De Tapas, K. et al. (Apr. 17, 2007) "Nanoparticle Albumin-Bound (nab) Rapamycin as an Anticancer Agent," *Proceedings of the Annual*

(56) References Cited

OTHER PUBLICATIONS

*Meeting of the American Association for Cancer Research*, held on Apr. 14, 18, 2007, in Los Angeles, California 48(1):1117, Abstract No. 4719.

Ellerby, H. M. et al. (Sep. 1999). "Anti-Cancer Activity of Targeted Pro-Apoptotic Peptides," *Nat. Med.* 5(9):1032-1038.

Fehske, K. J. et al. (Apr. 1, 1981). "The Location of Drug Binding Sites in Human Serum Albumin," *Biochem. Pharmacol.* 30(7):687-692.

Gartner, S. et al. (Aug. 1980). "Long-Term Culture of Human Bone Marrow Cells," *Proc. Natl. Acad. Sci. USA* 77(8):4756-4759.

Gupta, D. et al. (Dec. 2001). "Adherence of Multiple Myeloma Cells to Bone Marrow Stromal Cells Upregulates Vascular Endothelial Growth Factor Secretion: Therapeutic Applications," *Leukemia* 15(12):1950-1961.

Hawkins, M. J. et al. (May 22, 2008, e-pub. Feb. 7, 2008). "Protein Nanoparticles as Drug Carriers in Clinical Medicine," *Advanced Drug Delivery Reviews* 60(8):876-885.

He, X. M. et al. (Jul. 16, 1992). "Atomic Structure and Chemistry of Human Serum Albumin," *Nature* 358(6383):209-215.

Herzog, T. J. (Nov. 15, 2004). "Recurrent Ovarian Cancer: How Important is it to Treat to Disease Progression?" *Clin. Cancer Res.* 10:7439-7449.

Hideshima, T. et al. (May 15, 2006). "Perifosine, An Oral Bioactive Novel Alkylphospholipid, Inhibits Akt and Induces in Vitro and in Vivo Cytotoxicity in Human Multiple Myeloma Cells," *Blood* 107(10):4053-4062.

Icon et al. (Jun. 21, 2003). "Paclitaxel Plus Platinum-Based Chemotherapy Versus Conventional Platinum-Based Chemotherapy in Women with Relapsed Ovarian Cancer: The ICON4/AGO-OVAR-2.2 Trial," *Lancet* 361(9375):2099-2106.

Koshkina, N. V. et al. (2003). "Camptothecins and Lung Cancer: Improved Delivery Systems by Aerosol," *Current Cancer Drug Targets* 3(4):251-264.

Kragh-Hansen, U. (Feb. 1990). "Structure and Ligand Binding Properties of Human Serum Albumin," *Dan. Med. Bull.* 37(1)57-84.

Micha, J. P. et al. (Feb. 2006, e-pub. Oct. 15, 2005). "Abraxane in the Treatment of Ovarian Cancer: The Absence of Hypersensitivity Reactions," *Gynecologic Oncology* 100(2):437-438.

Mitsiades, C. S. et al. (Aug. 1, 2001). "Trail/Apo2L Ligand Selectively Induces Apoptosis and Overcomes Drug Resistance in Multiple Myeloma: Therapeutic Applications," *Blood* 98(3):795-804.

Mitsiades, N. et al. (Oct. 29, 2002). "Molecular Sequelae of Proteasome Inhibition in Human Multiple Myeloma Cells," *Proc. Natl. Acad. Sci. USA* 99(22):14374-14379.

Mitsiades, N. et al. (May 15, 2003). "Molecular Sequelae of Histone Deacetylase Inhibition in Human Malignant B Cells," *Blood* 101(10):4055-4062.

Mitsiades, N. et al. (Mar. 15, 2003). "The Proteasome Inhibitor PS-341 Potentiates Sensitivity of Multiple Myeloma Cells to Conventional Chemotherapeutic Agents: Therapeutic Applications," *Blood* 101(6):2377-2380.

Muggia, F. M. (Dec. 2006). "New and Emerging Intraperitoneal (IP) Drugs for Ovarian Cancer Treatment," *Seminars in Oncology* 33(6)(Suppl. 12):S18-S24.

Nishimura. T. et al. (Feb. 2001). "40-O-(2-Hydroxyethyl)-rapamycin Attenuates Pulmonary Arterial Hypertension and Neointimal Formation in Rats," *Am. J. Respir. Crit. Care Med.* 163(2):498-502.

Paddenberg, R. et al. (Feb. 24, 2007). "Rapamycin Attenuates Hypoxia-Induced Pulmonary Vascular Remodeling and Right Ventricular Hypertrophy in Mice," *Respiratory Research* 8(1):15, total of 12 pages.

Rustin, G. J. et al. (Jun. 1, 2004). "Use of CA-125 in Clinical Trial Evaluation of New Therapeutic Drugs for Ovarian Cancer," *Clin. Cancer Res.* 10(11):3919-3926.

Sugio, S. et al. (Jun. 1999). "Crystal Structure of Human Serum Albumin at 2.5 Å Resolution," *Protein. Eng.* 12(6):439-446.

Tai, Y.-T. et al. (Feb. 21, 2000). "Isolation and Characterization of Human Multiple Myeloma Cell Enriched Populations," *J. Immunol. Methods* 235(1-2):11-19.

Therasse, P. et al. (Feb. 2, 2000). "New Guidelines to Evaluate the Response to Treatment in Solid Tumors," *J. Natl. Cancer Inst.* 92(3):205-216.

Trieu, V. et al. (Dec. 2007). "mTOR Inhibitor Nanoparticle Albumin-Bound (nab) Rapamycin is Effective in a Breast Cancer Xenograft Model," *Breast Cancer Research and Treatment, 30th Annual San Antonio Breast Cancer Symposium;* San Antonio, Texas, USA, held on Dec. 13-16, 2007 106(supplement 1):S268, Abstract 6063.

Uchiyama, H. et al. (Dec. 15, 1993). "Adhesion of Human Myeloma-Derived Cell Lines to Bone Marrow Stromal Cells Stimulates Interleukin-6 Secretion," *Blood* 82(12):3712-3720.

Vorum, H. (Nov. 1999). "Reversible Ligand Binding to Human Serum Albumin. Theoretical and Clinical Aspects," *Dan. Med. Bull.* 46(5):379-399.

Zaiman, A. et al. (Nov. 2005). "One Hundred Years of Research in the Pathogenesis of Pulmonary Hypertension," *Am. J. Respir. Cell Mol. Biol.* 33(5):425-431.

Zhou, H. al. (Jan. 2006). "Heme Oxygenase-1 Mediates the Protective Effects of Rapamycin in Monocrotaline-Induced Pulmonary Hypertension," *Lab. Investigation* 86(1):62-71.

International Search Report mailed on Jul. 22, 2008, for PCT Patent Application No. PCT/US2008/003096 filed on Mar. 7, 2008, published as WO 2008/109163 on Sep. 12, 2008, 3 pages.

Written Opinion mailed on Jul. 22, 2008, for PCT Patent Application No. PCT/US2008/003096 filed on Mar. 7, 2008, published as WO 2008/109163 on Sep. 12, 2008, 10 pages.

International Search Report mailed on Dec. 22, 2008, for PCT Patent Application No. PCT/US2008/005792 filed on May 5, 2008, published as WO 2008/137148 on Nov. 13, 2008, 7 pages.

Written Opinion mailed on Dec. 22, 2008, for PCT Patent Application No. PCT/US2008/005792 filed on May 5, 2008, published as WO 2008/150531 on Nov. 13, 2008, 10 pages.

International Search Report mailed on Oct. 9, 2008, for PCT Patent Application No. PCT/US2008/007024 filed on Jun. 2, 2008, published as WO 2008/150532 on Dec. 11, 2008, 3 pages.

Written Opinion mailed on Oct. 9, 2008, for PCT Patent Application No. PCT/US2008/007024 filed on Jun. 2, 2008, published as WO 2008/150532 on Dec. 11, 2008, 6 pages.

European Office Action mailed on Jun. 30, 2011, for European Patent Application No. 08 768 111.0 filed on Jun. 2, 2008, 5 pages.

Non Final Office Action mailed on Sep. 27, 2011, for U.S. Appl. No. 12/832,876, filed Jul. 8, 2010, for Desai et al., 16 pages.

Non Final Office Action mailed on Nov. 21, 2011, for U.S. Appl. No. 12/422,192, filed Apr. 10, 2009, 20 pages.

U.S. Appl. No. 09/937,840, filed Jan. 28, 2002, for Desai et al.

U.S. Appl. No. 12/479,710, filed Jun. 5, 2009, for Desai et al.

U.S. Appl. No. 13/228,323, filed Sep. 8, 2011, for Desai et al.

U.S. Appl. No. 13/263,723, internationally filed Apr. 9, 2010, for Desai et al.

U.S. Appl. No. 13/133,367, internationally filed Dec. 11, 2009, for Trieu et al.

U.S. Appl. No. 13/255,893, internationally filed Mar. 12, 2010, for Desai et al.

U.S. Appl. No. 13/073,824, filed Mar. 28, 2011, for Desai et al.

U.S. Appl. No. 13/073,861, filed Mar. 28, 2011, for Desai et al.

Ballou, L. M. et al. (Jun. 27, 2003). "Activated $G\alpha_q$ inhibits p110$\alpha$ Phosphatidylinositol 3-Kinase and Akt," *J. Biol. Chem.* 278(26):23472-23479.

De Mulder, P.H. et al. (2004). "Current Treatment of Renal Cell Carcinoma," *Ann. Oncol.* 15(Suppl. 4):319-328.

Desai, N. et al. (Dec. 2009). Combination Regimens of nab-Rapamycin (ABI-009) Effective Against MDA-MB-231 Breast-Tumor Xenografts, Cancer Res. 69(24), Supplement 3, ABS 6106, 32nd *Annual San Antonio Breast Cancer Symposium*, San Antonio, Texas, USA, located at <http://cancerres.aacrjournals.org/cgi/content/abstract/69/24_MeetingAbstracts/6106>, one page.

Hung, G. Y. et al. (Jan. 2002). "Nonmyeloablative Allogeneic Bone Marrow Transplantation for Orbital Granulocytic Sarcoma Associated with t(8;21)(q22;q22) in Acute Myeloid Leukemia," *Bone Marrow Transplant.* 29(1):67-70.

Kim. D. et al. (Dec. 1, 2005). "Targeting the Phosphatidylinositol-3 Kinase /Akt Pathway for the Treatment of Cancer," *Curr. Opin. Invest. Drugs.* 6(12):1250-1258.

(56) References Cited

OTHER PUBLICATIONS

Konski, A. et al. (Jan. 1, 2006, e-ub. Dec. 1, 2005). "Long-Term Hormone Therapy and Radiation is Cost-Effective for Patients With Locally Advanced Prostate Carcinoma," *Cancer* 106(1):51-57.
Liu, X. Y. et al. (Oct. 2006). "A Mini-Review of Targeting Gene-Virotherapy of Cancer," *Chinese Journal of Cancer* 25(10):1320-1322.
Liu, L. et al. (Nov. 9, 2006). "Rapamycin Inhibits Cell Motility by Suppression of mTOR-Mediated S6K1 and 4E-BP1 Pathways," *Oncogene* 25(10) :7029-7040.
Luan, F. L. et al. (May 27, 2022). "Rapamycin Blocks Tumor Progression: Unlinking Immunosuppression From Antitumor Efficacy," *Transplantation* 73(10)1565-1572.
Muramatsu, T. et al. (Jul. 1, 2006). "Treatment Strategy for Recurrent and Refractory Epithelial Ovarian Cancer: Efficacy of High-Dose Chemotherapy With Hematopoietic Stem Cell Transplantation,"*Acta Histochem. Cytochem.* 39(3):61-67.
Sarbassov, D. D. et al. (Apr. 21, 2006). "Prolonged Rapamycin Treatment Inhibits mTORC2 Assembly and Akt/PKB," *Mol. Cell.* 22(2):159-168.
Sato, A. et al. (2006). "Prophylaxis of Mucosal Toxicity by Oral Propantheline and Cryotherapy in Children With Malignancies Undergoing Myeloablative Chemo-Radiotherapy," *Tohoku J. Exp. Med.* 210(4) :315-320.
Wu, F. et al. (Jul. 2005). "Extracorporeal High Intensity Focused Ultrasound Treatment for Patients With Breast Cancer," *Breast Cancer Res. Treat.* 92(1):51-60.
Wullschleger, S. et al. (2006). "TOR Signalling in Growth and Metabolism," *Cell* 124(3):471-484.
European Search Report mailed on Sep. 7, 2012, for European Patent Application No. 12152463.1, filed on Mar. 7, 2008, published on Aug. 1, 2012, as EP 2 481 409, 7 pages.
European Search Report mailed on Sep. 11, 2012, for European Patent Application No. 08767585.6, filed on Mar. 5, 2008, published on Jan. 27, 2010, as EP 2 146 707, 4 pages.
European Office Action mailed on Jul. 5, 2012, for European Patent Application No. 08768111.0 filed on Jun. 2, 2008, 3 pages.
European Office Action mailed on Sep. 4, 2012, for European Patent Application No. 08726605.2 filed on Mar. 7, 2008, 7 pages.
European Search Report and European Search Opinion mailed on Sep. 17, 2012, for European Patent Application No. 12152455.7, filed on Mar. 7, 2008, published on Aug. 1, 2012, as EP 2 481 402, 9 pages.
Final Office Action mailed on Apr. 27, 2012, for U.S. Appl. No. 12/832,876, filed Jul. 8, 2010, for Desai et al., 14 pages.
Final Office Action mailed on May 22, 2012, for U.S. Appl. No. 12/422,192, filed Apr. 10, 2009, 26 pages.
U.S. Appl. No. 09/446,783, filed May 16, 2000, for Desai et al.
U.S. Appl. No. 13/392,501, internationally filed Aug. 25, 2010, for Tao et al.
U.S. Appl. No. 13/368,250, filed Feb. 7, 2012, for Desai et al.
U.S. Appl. No. 13/368,297, filed Feb. 7, 2012, for Desai et al.
U.S. Appl. No. 13/408,994, filed Feb. 29, 2012, for De et al.
U.S. Appl. No. 13/423,095, filed Mar. 16, 2012, for Desai et al.
Duan Qiong-wen et al. "Rapamycin Associated Molecular Target mTOR Development of Novel Antineoplastic Drugs," translated as "Molecular Target of Rapamycin mTOR Associated With the Development of New Anticancer Drugs," *Journal of Medicine Research* 35(4):55-58, (Apr. 30, 2006).
Noh, W-C. et al. (Feb. 1, 2004). "Determinants of Rapamycin Sensitivity in Breast Cancer Cells," *Clinical Cancer Research* 10:1013-1023.
Beppo, M. et al. (May 2001). "Weekly Paclitaxel and Cisplatin in Recurrent Ovarian Cancer," *Japanese Journal of Cancer and Chemotherapy* 28(50):643-648. (English Abstract).
Gonzalez-Martin, A.J. et al. (2005). "Randomized Phase II Trial of Carboplatin Versus Paclitaxel and Carboplatin in Platinum-Sensitive Recurrent Advanced Ovarian Carcinoma: A GEICO (Grupo Español de Investigacion en Cáncer de Ovario) Study," *Annuals of Oncology* 16(5):749-755.

Kawagoe, H. et al. (Jan. 2003). "Weekly Paclitaxel Infusion in Patients with Recurrent Ovarian Cancer—A Pilot Study," *Japanese Journal of Cancer and Chemotherapy* 30(1):151-154. (English Abstract).
Pfizer. (2012). Patient Information Leaflet included with Rapamune® (Sirolimus) Oral Solution and Tablets Packages Insert LAB-0579-1.0, instructions approved by the U.S. Food and Drug Administration, published under "Full Prescribing Information," at http://labeling.pfizer.com/showlabeling.aspx?id=139, instructions revised Dec. 2012 by Pfizer distributed by Wyeth Pharmaceuticals, Inc., 53 pages.
Rose, P.G. et al. (1998). "Second-Line Therapy With Paclitaxel and Carboplatin for Recurrent Disease Following First-Line Therapy With Paclitaxel and Platinum in Ovarian or Peritoneal Carcinoma," *Journal of Clinical Oncology* 16(4):1494-1497.
Uraba, S. et al. (Mar. 2004). "Recurrent Ovarian Cancer Peritonitis Treated with Weekly Paclitaxel Infusion: A Clinicopharmacological Study," *Japanese Journal of Cancer and Chemotherapy* 31(3):449-451. (English Abstract).
U.S. Appl. No. 13/649,987, filed Oct. 11, 2012, for Desai et al.
U.S. Appl. No. 13/777,980, filed Feb. 26, 2013, for Desai et al.
U.S. Appl. No. 13/777,988, filed Feb. 26, 2013, for Desai et al.
U.S. Appl. No. 13/564,633, filed Aug. 1, 2012, for Desai et al.
U.S. Appl. No. 13/585,696, filed Aug. 14, 2012, for Desai et al.
U.S. Appl. No. 13/743,212, filed Jan. 1, 2013, for Desai et al.
U.S. Appl. No. 13/776,481, filed Feb. 25, 2013, for Desai et al.
U.S. Appl. No. 13/776,484, filed Feb. 25, 2013, for Desai et al.
U.S. Appl. No. 13/779,625, filed Feb. 27, 2013, for Desai et al.
U.S. Appl. No. 13/779,624, filed Feb. 27, 2013, for Desai et al.
U.S. Appl. No. 13/779,621, filed Feb. 27, 2013, for Desai et al.
U.S. Appl. No. 13/781,482, filed Feb. 28, 2013, for Desai et al.
U.S. Appl. No. 13/781,479, filed Feb. 28, 2013, for Desai et al.
U.S. Appl. No. 13/781,489, filed Feb. 28, 2013, for Trieu et al.
U.S. Appl. No. 13/781,487, filed Feb. 28, 2013, for Tao et al.
U.S. Appl. No. 13/781,480, filed Feb. 28, 2013, for Yeo et al.
U.S. Appl. No. 13/782,990, filed Mar. 1, 2013, for Desai et al.
U.S. Appl. No. 13/782,988, filed Mar. 1, 2013, for Desai et al.
U.S. Appl. No. 13/701,003, filed May 20, 2011, for Desai et al.
U.S. Appl. No. 13/782,984, filed Mar. 1, 2013, for Desai et al.
U.S. Appl. No. 13/701,002, filed May 20, 2011, for Desai et al.
U.S. Appl. No. 13/783,122, filed Mar. 1, 2013, for Desai et al.
U.S. Appl. No. 13/701,001, filed May 20, 2011, for Desai et al.
U.S. Appl. No. 13/782,992, filed Mar. 1, 2013, for Desai et al.
U.S. Appl. No. 13/794,705, filed Mar. 12, 2013, for Desai et al.
U.S. Appl. No. 13/791,841, filed Mar. 12, 2013, for Desai et al.
U.S. Appl. No. 13/794,480, filed Mar. 12, 2013, for Desai et al.
U.S. Appl. No. 13/794,486, filed Mar. 12, 2013, for Heise et al.
U.S. Appl. No. 13/794,712, filed Mar. 11, 2013, for Pierce et al.
Aapro, M. et al. (Apr. 2014). "Adverse Event Management in Patients With Advanced Cancer Receiving Oral Everolimus: Focus on Breast Cancer," *Annals of Oncology* 25(4):763-773.
AFINITOR® Insert. (Feb. 2014). "Highlights of Prescribing Information," AFINITOR® pp. 1-41.
Amato, R. J. et al. (Jun. 1, 2009, e-pub. Mar. 20, 2009). "A Phase 2 Study With a Daily Regimen of the Oral mTOR Inhibitior RAD001 (Everolimus) in Patients With Metastatic Clear Cell Renal Cell Cancer," *Cancer* 115:2438-2446.
Atkins, M.B. et al. (Mar. 1, 2004). "Radomized Phase II Study of Multiple Dose Levels of CCI-779, a Novel Mammalian Target of Rapamycin Kinase Inhibitor, in Patients With Advanced Refractory Renal Cell Carcimona," *Journal of Clinical Oncology* 22(5):909-918.
Baselga, J. et al. (Feb. 9, 2012, e-pub. Dec. 7, 2011). "Everolimus in Postmenopausal Hormone-Receptor-Positive Advanced Breast Cancer," *The New England Journal of Medicine* 366(6):520-529.
Baselga, J. et al. (Jun. 1, 2009, e-pub. Jan. 12, 2009). "Phase II Randomized study of Neoadjuvant Everolimus Plus Letrozole Compared With Placebo Plus Letrozole in Patients With Estrogen Receptor-Positive Breast Cancer," *Journal of Clinical Oncology* 27(16):2630-2637.
Bryce, A.H. et al. (Oct. 2012). "Phase I Study of Temsirolimus in Combination With EKB-569 in Patients With Advanced Solid Tumors," *Invest. New Drugs* 30(5):1-16.

(56) References Cited

OTHER PUBLICATIONS

Buckner, J.C. et al. (2010, e-pub. May 5, 2009). "Phase I, Pharmacokinetic Study of Termsirolimus Administered Orally to Patients With Advanced Cancer," *Invest. New Drugs* 28:334-342.

Campone, M. et al. (2009, e-pub. Jan. 6, 2009). "Safety and Pharmacokinetics of Paclitaxel and the Oral mTOR Inhibitor Everolimus in Advanced Solid Tumuors," *British Journal of Cancer* 100(2):315-321.

Chan, S. et al. (Aug. 10, 2005). "Phase II Study of Temsirolimus (CCI-779), A Novel Inhibitor of mTOR, in Heavily Pretreated Patients With Locally Advanced or Metastatic Breast Cancer," *Journal of Clinical Oncology* 23(23):5314-5322.

Chawla, S.P. et al. (Jan. 1, 2012, e-pub. Nov. 7, 2011). "Phase II Study of the Mammalian Target of Rapamycin Inhibitor Ridaforolimus in Patients With Advanced Bone and Soft Tissue Sarcomas," *Journal of Clinical Oncology* 30(1):78-84.

Cohen, E.E.W. et al. (Sep. 1, 2012, e-pub. Aug. 7, 2012). "Phase I Studies of Sirolimus Alone or in Combination With Pharmacokinetic Modulators in Advanced Cancer Patients," *Clin. Cancer Res.* 18(17):4785-4793.

Deenen, M.J. et al. (2012, e-pub. Aug. 2, 2011). "Phase I and Pharmacokinetic Study of Capecitabine and the Oral mTOR Inhibitor Everolimus in Patients with Advanced Solid Malignancies," *Invest. New Drugs* 30:1557-1565.

Doi, T. et al. (Apr. 10, 2010, e-pub. Mar. 15, 2010). "Multicenter Phase II Study of Everolimus in Patients With Previously Treated Metastatic Gastric Cancer," *Journal of Clinical Oncology* 28(11):1904-1910.

Duran, I. et al. (2006, e-pub. Oct. 10, 2006). "A Phase II Clinical and Pharmacodynamic Study of Temsirolimus in Advanced Neuroendocrine Carcinomas," *British Journal of Cancer* 95(9):1148-1154.

Ellard, S.L. et al. (Sep. 20, 2009, e-pub. Aug. 17, 2009). "Randomized Phase II Study Comparing Two Schedules of Everolimus in Patients With Recurrent/Metastatic Breast Cancer: NCIC Clinical Trials Group IND. 163," *Journal of Clinical Oncology* 27(27):4536-4541.

Farag, S.S. et al. (Nov. 2009). "Phase II Trial of Temsirolimus in Patients with Relapsed or Refractory Multiple Myeloma," *Leuk. Res.* 33(11):1475-1480.

Fouladi, M. et al. (Oct. 20, 2007). "Phase I Study of Everolimus in Pediatric Patients With Refractory Solid Tumors," *Journal of Clinical Oncology* 25(30):4806-4812.

Fujisaka, Y. et al. (2010, e-pub. Apr. 29, 2010). "A Phase 1 Clinical Study of Temsirolimus (CCI-779) in Japanese Patients With Advanced Solid Tumor," *Jpn. J. Clin. Oncol.* 40(8):732-738.

Galanis, E. et al. (Aug. 10, 2005). "Phase II Trial of Temsirolimus (CCI-779) in Recurrent Glioblastoma Multiforme: A North Central Cancer Treatment Group Study," *Journal of Clinical Oncology* 23(23):5294-5304.

Gonzalez-Angulo, A.M. et al. (Oct. 1, 2013). "Weekly nab-Rapamycin in Patients With Advanced Nonhematologic Malignancies: Final Results of a Phase I Trial," *Clinical Cancer Research* 19(19):5474-5484.

Hainsworth, J.D. et al. (May 1, 2010, e-pub. Apr. 5, 2010). "Phase II Trial of Bevacizumab and Everolimus in Patients With Advanced Renal Cell Carcinoma," *Jounal of Clinical Oncology* 28(13):2131-2136.

Hartford, C.M. et al. (Feb. 15, 2009). "A Phase I Trial to Determine the Safety, Tolerability, and Maximum Tolerated Dose of Deforolimus in Patients With Advanced Malignancies," *Clin. Cancer Res.* 15(4):1428-1434.

Hess, G. et al. (Aug. 10, 2009, e-pub. Jul. 6, 2009). "Phase III Study to Evaluate Temsirolimus Compared With Investigator's Choice Therapy for the Treatment of Relapsed or Refractory Mantle Cell Lymphoma," *Journal of Clinical Oncology* 27(23):3822-2829.

Hidalgo, M. et al. (Oct. 1, 2006). "A Phase I and Pharmacokinetic Study of Temsirolimus (CCI-779) Administered Intravenously Daily for 5 Days Every 2 Weeks to Patients With Advanced Cancer," *Clin. Cancer Res.* 12(19):5755-5763.

Hudes, G. et al. (May 31, 2007). "Temsirolimus, Interferon Alfa, or Both for Advanced Renal-Cell Carcinoma," *The New England Journal of Medicine* 356(22):2271-2281.

Javle, M.M. et al. (2010). "Inhibition of the Mammalian Target of Rapamycin (mTOR) in Advanced Pancreatic Cancer: Results of Two Phase II Studies," *BMC Cancer* 10(368)1-7.

Kita, T. et al. (2004). The Effect of Single Weekly Paclitaxel in Heavily Pretreated Patients with Recurrent or Persistent Advanced Ovarian Cancer, *Gynecologic Oncology* 92:813-818.

Margolin, K. et al. (Sep. 1, 2005, e-pub. Jul. 8, 2005). "CCI-779 in Metastatic Melanoma. A Phase II Trial of the California Cancer Consortium," *Cancer* 104(5):1045-1048.

Martins, F. et al. (2013, e-pub. Jan. 9, 2013). "A Review of Oral Toxicity Associated With mTOR Inhibitor Therapy in Cancer Patients," *Oral Oncology* 49:293-298.

Meier-Kriesche, H-U. et al. (2000). "Toxicity and Efficacy of Sirolimus: Relationship to Whole-Blood Concentrations," *Clinical Therapeutics* 22(Suppl. B):B93-B100.

Milton, D.T. et al. (Aug. 1, 2007, e-pub.Jun. 18, 2007). "Phase 1 Trial of Everolimus and Gefitinib in Patients With Advanced Nonsmall-Cell Lung Cancer," *Cancer* 110(3):599-605.

Mita, M.M. et al. (Jan. 20, 2008). "Phase I Trial of the Novel Mammalian Target of Rapamycin Inhibitor Deforolimus (AP23573; MK-8669) Administered Intravenously Daily for 5 Days Every 2 Weeks to Patients With Advanced Malignancies," *Journal of Clinical Oncology* 26(3):361-367.

Motzer, R. J. et al. (Sep. 1, 2007). "Phase I/II Trial of Temsirolimus Combined With Interferon Alfa for Advanced Renal Cell Carcinoma," *Journal of Clinical Oncology* 25(25):3958-3965.

Motzer, R.J. et al. (Sep. 15, 2010, e-pub. Jun. 14, 2010). "Phase 3 Trial of Everolimus for Metastatic Renal Cell Carcinoma," *Cancer* 116:4256-4265.

Naing, A. et al. (Sep. 15, 2011, e-pub. Jul. 12, 2011). "Phase I Trial of Cixutumumab Combined With Temsirolimus in Patients With Advanced Cancer," *Clin. Cancer Res.* 17(18):6052-6060.

O'Donnell, A. et al. (Apr. 1, 2008, e-pub. Mar. 10, 2008). "Phase I Pharmacokinetic and Pharmacodynamic Study of the Oral Mammalian Target of Rapamycin Inhibitior Everolimus in Patients With Advanced Solid Tumors," *Journal of Clinical Oncology* 26(10):1588-1595.

Okuno, S. et al. (Aug. 1, 2011, e-pub. Feb. 1, 2011). A Phase 2 Study of Temsirolimus (CCI-779) in Patients With Soft Tissue Sarcomas, *Cancer* 117:3468-3475.

Perotti, A. et al. (Oct. 20, 2010, e-pub. Sep. 20, 2010). "Phase IB Study of the mTOR Inhibitor Ridaforolimus With Capecitabine," *Journal of Clinical Oncology* 28(30):4554-4561.

Pham, P-T.T. et al. (Apr. 27, 2004). "Sirolimus-Associated Pulmonary Toxicity," *Transplantation* 77(8):1215-1220.

Punt, C.J.A. et al. (2003). "Phase I and Pharmacokinetic Study of CCI-779, a Novel Cytostatic Cell-Cycle Inhibitor, in Combination With 5-Fluorouracil and Leucovorin in Patients With Advanced Solid Tumors," *Annals of Oncology* 14:931-937.

Quek, R. et al. (Feb. 15, 2011, e-pub. Dec. 22, 2010). "Combination mTOR and IGF-1 R Inhibition: Phase I Trial of Everolimus and Figitumumab in Patients With Advanced Sarcomas and Other Solid Tumors," *Clin. Cancer Res.* 17(4):871-879.

Raymond, E. et al. (Jun. 15, 2004). "Safety and Pharmacokinetics of Escalated Doses of Weekly Intravenous Infusion of CCI-779, a Novel mTOR Inhibitor, in Patients With Cancer," *Journal of Clinical Oncology* 22(12):2336-2347.

Rizzieri, D.A. et al. (May 1, 2008). "A Phase 2 Clinical Trial of Deforolimus (AP23573, MK-8669), A Novel Mammalian Target of Rapamycin Inhibitor, in Patients With Relapsed or Refractory Hematologic Malignancies," *Clin. Cancer Res.* 14(9):2756-2762.

Seront, E. et al. (Oct. 2012, e-pub. Apr. 3, 2012). "Phase II Study of Everolimus in Patients With Locally Advanced or Metastatic Transitional Cell Carcinoma of the Urothelial Tract: Clinical Activity, Molecular Response, and Biomarkers," *Annals of Oncology* 23(10):2663-2670.

Sessa, C. et al. (Jun. 2010, e-pub. Nov. 9, 2009). "Phase lb Study of Weekly Mammalian Target of Rapamycin Inhibitor Ridaforolimus (AP23573; MK-8669) With Weekly Paclitaxel," *Annals of Oncology* 21(6):1315-1322.

(56) References Cited

OTHER PUBLICATIONS

Sivendran, S. et al. (2014). "Metabolic Complications With the Use of mTOR Inhibitors for Cancer Therapy," *Cancer Treatment Reviews* 40:190-196.

Slomovitz, B.M. et al. (Dec. 1, 2010, e-pub. Aug. 2, 2010). "A Phase 2 Study of the Oral Mammalian Target of Rapamycin Inhibitor, Everolimus, in Patients With Recurrent Endometrial Carcinoma," *Cancer* 116:5415-5419.

Smith, S.M. et al. (Nov. 1, 2010, e-pub. Sep. 13, 2010). "Termsirolimus Has Activity in Non-Mantle Cell Non-Hodgkin's Lymphoma Subtypes: The University of Chicago Phase II Consortium," *Journal of Clinical Oncology* 28(31):4740-4746.

Soria, J-C. et al. (Oct. 2009, e-pub. Jun. 23, 2009). "Efficacy of Everolimus (RAD001) in Patients With Advanced NSCLC Previously Treated With Chemotherapy Alone or With Chemotherapy and EGFR Inhibitors," *Annals of Oncology* 20(10):1674-1681.

Tabernero, J. et al. (Apr. 1, 2008, e-pub. Mar. 10, 2008). "Dose- and Schedule-Dependent Inhibition of the Mammalian Target of Rapamycin Pathway With Everolimus: A Phase I Tumor Pharmacodynamic Study in Patients With Advanced Solid Tumors," *Journal of Clinical Oncology* 28(10):1603-1610.

Tarhini, A. et al. (Dec. 1, 2010, e-pub. Nov. 2, 2010). "Phase II Study of Everolimus (RAD001) in Previously Treated Small Cell Lung Cancer," *Clin. Cancer Res.* 16(23):5900-5907.

Torisel®. (May 2014). "Highlights of Prescribing Information," located at <http://labeling.pfizer.com/showlabeling.aspx?id=490>, last visited on May 15, 2014, 21 pages.

Witzig, T.E. et al. (Aug. 10, 2005). "Phase II Trial of Single-Agent Temsirolimus (CCI-779) for Relapsed Mantle Cell Lymphoma," *Journal of Clinical Onology* 23(23):5347-5356.

Wolpin, B.M. et al. (Jan. 10, 2009, e-pub. Dec. 1, 2008). "Oral mTOR Inhibitor Everolimus in Patients With Gemcitabine-Refractory Metastatic Pancreatic Cancer," *Journal of Clinical Oncology* 27(2):193-198.

Yao, J.C. et al. (Feb. 10, 2011). "Everolimus for Advanced Pancreatic Neuroendocrine Tumors," *New England Journal of Medicine* 364(6):514-523.

Yao, J.C. et al. (Jan. 1, 2010, e-pub. Nov. 23, 2009). "Daily Oral Everolimus Activity in Patients With Metastatic Pancreatic Neuroendocrine Tumors After Failure of Cytotoxic Chemotherapy: A Phase II Trial," *Journal of Clinical Oncology* 28(1):69-76.

Yee, K.W.L. et al. (Sep. 1, 2006). "Phase I/II Study of the Mammalian Target of Rapamycin Inhibitor Everolimus (RAD001) in Patients With Relapsed or Refractory Hematologic Malignancies," *Clin. Cancer Res.* 12(17):5165-5173.

Non-Final Office Action mailed on Feb. 13, 2014, for U.S. Appl. No. 13/781,479, filed Feb. 28, 2013, 39 Pages.

European Examination Report mailed May 9, 2014, for EP Application No. 08767585.6, filed on May 5, 2008, 7 pages.

\* cited by examiner

Figure 1.

| | 1 mg/kg (N=5) | 15 mg/kg (N=4) | 30 mg/kg (N=3) | 45 mg/kg (N=4) |
|---|---|---|---|---|
| HL (hr) | 14.3 ± 6.3 | 25.83 ± 10.05 | 18.47 ± 1.61 | 13.45 ± 3.24 |
| $T_{max}$ (hr) | 0.017 ± 0.000 | 0.017 ± 0.000 | 0.017 ± 0.000 | 0.017 ± 0.000 |
| $C_{max}$ (ng/ml) | 958.7 ± 677.0 | 7354 ± 2233 | 54118 ± 39758 | 70436 ± 38396 |
| $AUC_{last}$ (hr*ng/ml) | 487.3 ± 101.7 | 5654 ± 910 | 14834 ± 4764 | 25421 ± 4085 |
| $AUC_{inf}$ (hr*ng/ml) | 669.1 ± 222.1 | 6017 ± 647 | 15309 ± 4899 | 25774 ± 4108 |
| $AUC_{Extrap}$ (%) | 24.1 ± 14.1 | 6.450 ± 6.16 | 3.13 ± 0.24 | 1.38 ± 0.83 |
| $V_z$ (L/kg) | 30.6 ± 7.2 | 66.04 ± 57.45 | 56.11 ± 18.36 | 34.15 ± 8.17 |
| CL (L/hr/kg) | 1.6 ± 0.6 | 2.51 ± 0.28 | 2.08 ± 0.58 | 1.78 ± 0.26 |
| $V_{ss}$ (L/kg) | 24.8 ± 7.6 | 33.82 ± 22.19 | 14.91 ± 4.54 | 9.55 ± 2.24 |
| MRT (hr) | | 15.76 ± 6.94 | 7.11 ± 0.30 | 5.35 ± 0.94 |

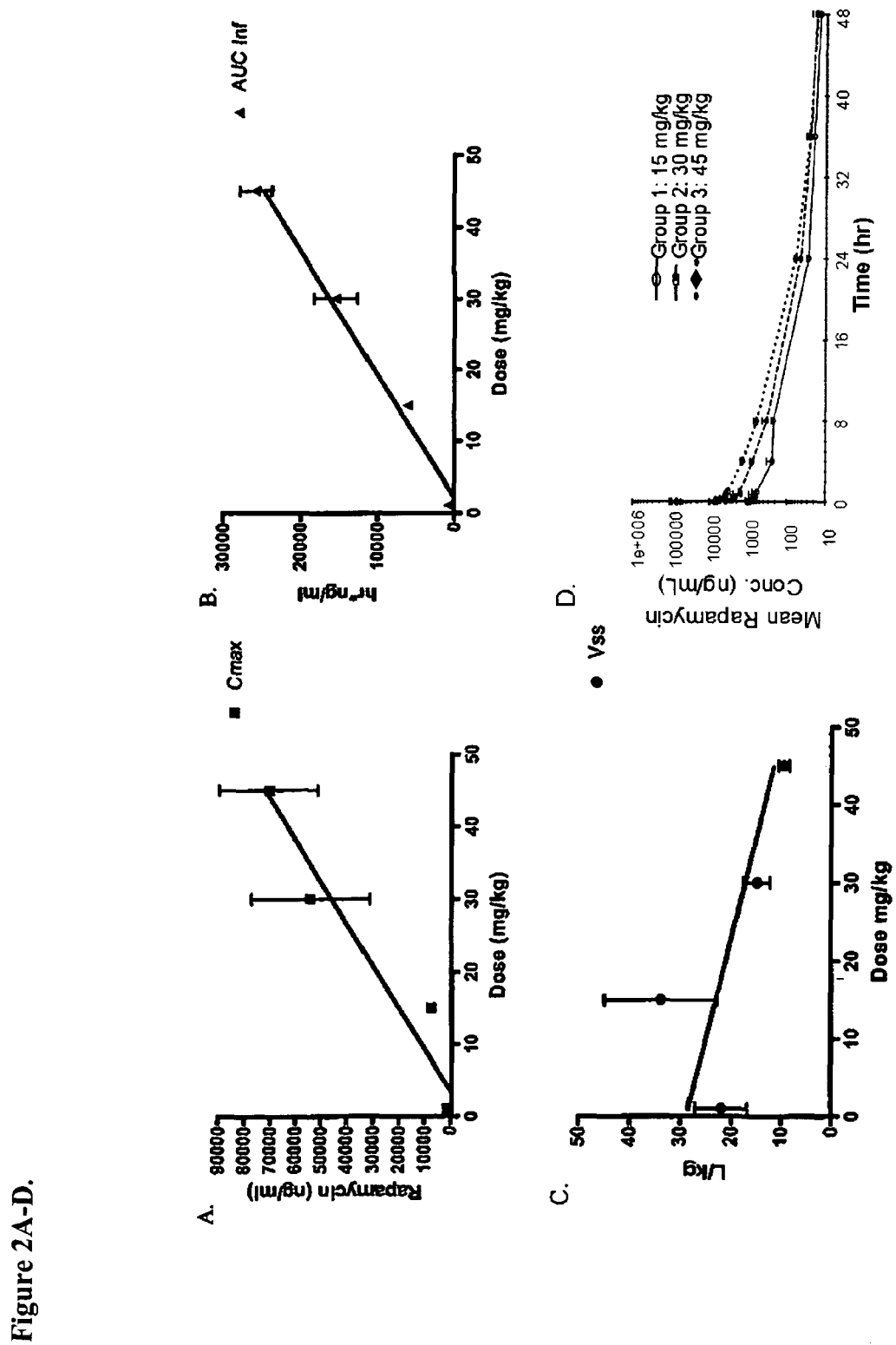
Figure 2A-D.

Antitumor Activity of Nab-Rapamycin in MM1S Multiple Myeloma Xenograft Model

NANOPARTICLE COMPRISING RAPAMYCIN AND ALBUMIN AS ANTICANCER AGENT

CROSS-REFERENCE TO RELATED APPLICATIONS

This application is a National Phase filing under 35 U.S.C. §371 of International Application No. PCT/US2008/003096 having an international filing date of Mar. 7, 2008, which claims priority benefit to provisional application Ser. No. 60/905,669, filed Mar. 7, 2007, provisional application Ser. No. 60/905,734, filed Mar. 7, 2007, provisional application Ser. No. 60/905,662, filed Mar. 7, 2007, provisional application Ser. No. 60/905,735, filed Mar. 7, 2007, provisional application Ser. No. 60/905,672, filed Mar. 7, 2007, provisional application Ser. No. 60/905,787, filed Mar. 7, 2007, provisional application Ser. No. 60/905,663, filed Mar. 7, 2007, provisional application Ser. No. 60/905,767, filed Mar. 7, 2007, provisional application Ser. No. 60/905,750, filed Mar. 7, 2007, provisional application Ser. No. 60/923,248, filed Apr. 13, 2007, and provisional application Ser. No. 60/923,456, filed Apr. 13, 2007, the entire disclosures of each of which are hereby incorporated by reference.

TECHNICAL FIELD

This application relates to methods and compositions for treating, stabilizing, preventing, and/or delaying cancer using nanoparticles that comprise rapamycin or a derivative thereof The application further provides combination therapy methods of treating cancer comprising administering to an individual an effective amount of nanoparticles that comprise rapamycin or a derivative thereof and a second therapy.

BACKGROUND

The failure of a significant number of tumors to respond to drug and/or radiation therapy is a serious problem in the treatment of cancer. In fact, this is one of the main reasons why many of the most prevalent forms of human cancer still resist effective chemotherapeutic intervention, despite certain advances in the field of chemotherapy.

Cancer is now primarily treated with one or a combination of three types of therapies: surgery, radiation, and chemotherapy. Surgery is a traditional approach in which all or part of a tumor is removed from the body. Surgery generally is only effective for treating the earlier stages of cancer. While surgery is sometimes effective in removing tumors located at certain sites, for example, in the breast, colon, and skin, it cannot be used in the treatment of tumors located in other areas, inaccessible to surgeons, nor in the treatment of disseminated neoplastic conditions such as leukemia. For more than 50% of cancer individuals, by the time they are diagnosed they are no longer candidates for effective surgical treatment. Surgical procedures may increase tumor metastases through blood circulation during surgery. Most of cancer individuals do not die from the cancer at the time of diagnosis or surgery, but rather die from the metastasis and the recurrence of the cancer.

Other therapies are also often ineffective. Radiation therapy is only effective for individuals who present with clinically localized disease at early and middle stages of cancer, and is not effective for the late stages of cancer with metastasis. Radiation is generally applied to a defined area of the subject's body which contains abnormal proliferative tissue, in order to maximize the dose absorbed by the abnormal tissue and minimize the dose absorbed by the nearby normal tissue. However, it is difficult (if not impossible) to selectively administer therapeutic radiation to the abnormal tissue. Thus, normal tissue proximate to the abnormal tissue is also exposed to potentially damaging doses of radiation throughout the course of treatment. The efficacy of radiotherapeutic techniques in destroying abnormal proliferative cells is therefore balanced by associated cytotoxic effects on nearby normal cells. Because of this, radiotherapy techniques have an inherently narrow therapeutic index which results in the inadequate treatment of most tumors. Even the best radiotherapeutic techniques may result in incomplete tumor reduction, tumor recurrence, increased tumor burden, and induction of radiation resistant tumors.

Chemotherapy involves the disruption of cell replication or cell metabolism. Chemotherapy can be effective, but there are severe side effects, e.g., vomiting, low white blood cells, loss of hair, loss of weight and other toxic effects. Because of the extremely toxic side effects, many cancer individuals cannot successfully finish a complete chemotherapy regime. Chemotherapy-induced side effects significantly impact the quality of life of the individual and may dramatically influence individual compliance with treatment. Additionally, adverse side effects associated with chemotherapeutic agents are generally the major dose-limiting toxicity in the administration of these drugs. For example, mucositis is one of the major dose limiting toxicities for several anticancer agents, including 5-FU, methotrexate, and antitumor antibiotics, such as doxorubicin. Many of these chemotherapy-induced side effects if severe may lead to hospitalization, or require treatment with analgesics for the treatment of pain. Some cancer individuals die from the chemotherapy due to poor tolerance to the chemotherapy. The extreme side effects of anticancer drugs are caused by the poor target specificity of such drugs. The drugs circulate through most normal organs of individuals as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

Another problem associated with chemotherapy is the development of drug resistance. Drug resistance is the name given to the circumstances when a disease does not respond to a treatment drug or drugs. Drug resistance can be either intrinsic, which means that disease has never been responsive to the drug or drugs, or it can be acquired, which means the disease ceases responding to a drug or drugs that the disease had previously been responsive. Combination therapy, including combination chemotherapy, has the potential advantages of both avoiding the emergence of resistant cells and to kill pre-existing cells which are already drug resistant.

Due to the limitations of current treatments for cancer, the severity and breadth of neoplasm, tumor and cancer, there remains a significant interest in and need for additional or alternative therapies for treating, stabilizing, preventing, and/ or delaying cancer. Preferably, the treatments overcome the shortcomings of current surgical, chemotherapy, and radiation treatments.

BRIEF SUMMARY OF THE INVENTION

The present invention provides methods for the treatment of cancer using nanoparticles that comprise rapamycin or a derivative thereof Accordingly, the invention in some embodiments provides a method of treating cancer in an individual by administering to the individual (e.g., a human) an effective amount of a composition comprising nanoparticles that comprise rapamycin or a derivative thereof and a carrier protein. In some embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is not a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

In some embodiments, the amount of the rapamycin or derivative thereof in the effective amount of the composition is in the range of about 54 mg to about 540 mg, such as about 180 mg to about 270 mg or about 216 mg. In some embodiments, the rapamycin or derivative thereof is administered parenterally (e.g., intravenously). In some embodiments, a taxane is not administered to the individual (i.e., other than a taxane). In some embodiments, the taxane administered is not a nanoparticle taxane composition. In some embodiments, the rapamycin or derivative thereof is the only pharmaceutically active agent for the treatment of cancer that is administered to the individual. In some embodiments, rapamycin is administered. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

The invention also provides pharmaceutical compositions such as unit dosage forms that are useful for treating cancer. Accordingly, the invention in some embodiments provides a pharmaceutical composition (e.g., a unit dosage form of a pharmaceutical composition) that includes nanoparticles that comprise rapamycin or a derivative thereof and a carrier protein. In some embodiments, the composition also includes a pharmaceutically acceptable carrier. In various embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is not a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

In some embodiments, the amount of the rapamycin or derivatives thereof in the composition (e.g., a dose or a unit dosage form) is in the range of about 54 mg to about 540 mg, such as about 180 mg to about 270 mg, or about 216 mg. In some embodiments, the carrier is suitable for parenteral administration (e.g., intravenous administration). In some embodiments, a taxane is not contained in the composition. In some embodiments, the rapamycin or derivative thereof is the only pharmaceutically active agent for the treatment of cancer that is contained in the composition. In some embodiments, the composition comprises rapamycin. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

In yet another aspect, the invention includes a kit with (i) a composition comprising nanoparticles that comprise rapamycin or a derivative thereof and a carrier protein and (ii) instructions for use in treating cancer. In various embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is a plasmacytoma. In some embodiments, the cancer is multiple myeloma, renal cell carcinoma, prostate cancer, lung cancer, melanoma, brain cancer (e.g. glioblastoma), ovarian cancer, or breast cancer. In some embodiments, the cancer is not colon cancer. In some embodiments, the cancer is not breast cancer. In some embodiments, one or more symptoms of the cancer are ameliorated. In some embodiments, the cancer is delayed or prevented.

In some embodiments, the amount of the rapamycin or derivative thereof in the kit is in the range of about 54 mg to about 540 mg, such as about 180 mg to about 270 mg or about 216 mg. In some embodiments, the rapamycin or derivative thereof is administered parenterally (e.g., intravenously). In some embodiments, the kit does not contain a taxane. In some embodiments, the rapamycin or derivative thereof is the only pharmaceutically active agent for the treatment of cancer that is contained in the kit. In some embodiments, the kit comprises another pharmaceutically active agent for the treatment of cancer. In some embodiments, the other pharmaceutically active agent is a chemotherapeutic agent. In some embodiments, the kit comprises rapamycin. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

The present invention also provides methods for the treatment of cancer using combination therapies. The invention provides a method of treating cancer comprising a) a first therapy comprising administering to an individual an effective amount of a composition comprising nanoparticles comprising rapamycin or a derivative thereof and a carrier protein and b) a second therapy, such as surgery, radiation, gene therapy, immunotherapy, bone marrow transplantation, stem cell transplantation, hormone therapy, targeted therapy, cryotherapy, ultrasound therapy, photodynamic therapy, and/or chemotherapy (e.g., one or more compounds or pharmaceutically acceptable salts thereof useful for treating cancer).

In some embodiments, the invention provides a method of treating cancer in an individual comprising administering to the individual a) an effective amount of a composition comprising nanoparticles comprising a rapamycin or a derivative thereof and a carrier protein and b) an effective amount of at least one other chemotherapeutic agent. In some embodiments, the chemotherapeutic agent is any of (and in some embodiments selected from the group consisting of) taxane, antimetabolites (including nucleoside analogs), platinum-based agents, alkylating agents, tyrosine kinase inhibitors, anthracycline antibiotics, vinca alkloids, proteasome inhibitors, modulators of HER2/neu, modulators of EGFR, modulators of VEGFR, and topoisomerase inhibitors. In some embodiments, the chemotherapeutic agent is a platinum-based agent, such as carboplatin. In some embodiments, the chemotherapeutic agent is a modulator of HER2/neu (such as an inhibitor of HER2/neu for example Herceptin®). In some embodiments, the chemotherapeutic agent is a modulator of EGFR (such as an inhibitor of EGFR for example Erbitux®). In some embodiments, the chemotherapeutic agent is an anti-VEGF antibody (such as bevacizumab, e.g., Avastin®). In some embodiments, the effective amounts of the nanoparticle composition and the anti-VEGF antibody synergistically inhibit cell proliferation or metastasis. In some embodiments, the chemotherapeutic agent affects a signaling pathway involving a target of rapamycin. In some embodiments the chemotherapeutic agent affects a signaling pathway involving mTOR (such as the PI3K/Akt signaling pathway). In some embodiments, a taxane is not administered to the individual. In some embodiments, the taxane administered is not in a nanoparticle composition.

In some embodiments, the composition comprising nanoparticles comprising a rapamycin or a derivative thereof and a carrier protein and the chemotherapeutic agent are administered simultaneously, either in the same composition or in separate compositions. In some embodiments, the nanoparticle composition comprising a rapamycin or a derivative thereof and a carrier protein and the chemotherapeutic agent are administered sequentially, e.g., the nanoparticle composition is administered either prior to or after the administration of the chemotherapeutic agent. In some embodiments, the administration of the nanoparticle composition comprising a rapamycin or a derivative thereof and a carrier protein and the chemotherapeutic agent are concurrent, e.g., the administration period of the nanoparticle composition and that of the chemotherapeutic agent overlap with each other. In some embodiments, the administration of the nanoparticle composition comprising a rapamycin or a derivative thereof and a carrier protein and the chemotherapeutic agent are non-concurrent. For example, in some embodiments, the administration of the nanoparticle composition comprising a rapamycin or a derivative thereof and a carrier protein is terminated before the chemotherapeutic agent is administered. In some embodiments, the administration of the chemotherapeutic agent is terminated before the nanoparticle composition comprising a rapamycin or a derivative thereof and a carrier protein is administered.

In some embodiments, there is provided a method of treating cancer in an individual comprising a) a first therapy comprising administering to the individual a composition comprising nanoparticles comprising rapamycin or a derivative thereof and a carrier protein, and b) a second therapy comprising surgery, radiation, gene therapy, immunotherapy, bone marrow transplantation, stem cell transplantation, hormone therapy, targeted therapy, cryotherapy, ultrasound therapy, photodynamic therapy, or combinations thereof In some embodiments, the second therapy is hormone therapy. In some embodiments, the second therapy is radiation therapy. In some embodiments, the second therapy is surgery. In some embodiments, the first therapy is carried out prior to the second therapy. In some embodiments, the first therapy is carried out after the second therapy.

In some embodiments, the cancer being treated by combination therapy is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is not a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

In some embodiments, the amount of the rapamycin or derivative thereof in the effective amount of the composition used in combination therapy is in the range of about 54 mg to about 540 mg, such as about 180 mg to about 270 mg or about 216 mg. In some embodiments, the rapamycin or derivative thereof is administered parenterally (e.g., intravenously). In some embodiments, a taxane is not administered to the individual (i.e., other than taxane). In some embodiments, the taxane administered is not a nanoparticle taxane composition. In some embodiments, rapamycin is administered. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

The invention also provides pharmaceutical compositions such as unit dosage forms that are useful in combination therapy for treating cancer. Accordingly, the invention in some embodiments provides a pharmaceutical composition (e.g., a unit dosage form of a pharmaceutical composition) for use in combination therapy that includes nanoparticles that comprise rapamycin or a derivative thereof and a carrier protein. In some embodiments, the pharmaceutical composition includes a) nanoparticles comprising rapamycin or a derivative thereof and a carrier protein and b) at least one other therapeutic agent. In some embodiments, the other therapeutic agent comprises a chemotherapeutic agent. In some embodiments, the other therapeutic agent comprises a hormone therapeutic agent. In some embodiments, the composition also includes a pharmaceutically acceptable carrier. In some embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

In some embodiments, the amount of the rapamycin or derivatives thereof in the composition (e.g., a dose or a unit dosage form) for use in combination therapy is in the range of about 54 mg to about 540 mg, such as about 180 mg to about 270 mg, or about 216 mg. In some embodiments, the carrier is suitable for parenteral administration (e.g., intravenous administration). In some embodiments, a taxane is not contained in the composition. In some embodiments, the rapamycin or derivative thereof is the only pharmaceutically active agent for the treatment of cancer that is contained in the composition (for example, as part of a kit that contains instructions for using the composition with another therapy).

In some embodiments, the composition comprises rapamycin. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

In yet another aspect, the invention includes a kit with (i) a composition comprising nanoparticles that comprise rapamycin or a derivative thereof and a carrier protein and (ii) instructions for use in combination therapy for treating cancer. The invention also provides kits for using the rapamycin (or its derivatives) compositions described herein in combination therapy context. For example, a kit may provide such a composition in addition to another therapeutic composition. In some embodiments, the instructions are instructions for providing a first and second therapy, wherein either the first or second therapy comprises administering a composition that comprises nanoparticles of rapamycin or derivative thereof and a carrier protein. In some embodiments, the kit further comprises at least one other therapeutic agent. In some embodiments, the other therapeutic agent comprises a chemotherapeutic agent. In some embodiments, the other therapeutic agent comprises a hormone therapeutic agent. In some embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

In some embodiments, the amount of the rapamycin or derivative thereof in the kit for use in combination therapy is in the range of about 54 mg to about 540 mg, such as about 180 mg to about 270 mg or about 216 mg. In some embodiments, the rapamycin or derivative thereof is administered parenterally (e.g., intravenously). In some embodiments, the kit does not contain a taxane. In some embodiments, the rapamycin or derivative thereof is the only pharmaceutically active agent for the treatment of cancer that is contained in the kit. In some embodiments, the kit comprises another pharmaceutically active agent for the treatment of cancer. In some embodiments, the other pharmaceutically active agent is a chemotherapeutic agent. In some embodiments, the kit comprises rapamycin. In some embodiments, the composition comprises more than about 50% of the rapamycin or derivative thereof in nanoparticle form. In some embodiments, the carrier protein is albumin, such as human serum albumin. In some embodiments, the average diameter of the nanoparticles in the composition is no greater than about 200 nm (such as no greater than about 100 nm). In some embodiments, the nanoparticle compositions are sterile filterable. In some embodiments, the weight ratio of the carrier protein to the rapamycin or derivative thereof in the nanoparticles is less than about 18:1. In some embodiments, the weight ratio of the carrier protein to the rapamycin or derivative thereof in the nanoparticle compositions is less than about 18:1.

The invention also provides any of the compositions described (e.g., a composition comprising nanoparticles that comprise rapamycin or a derivative thereof and a carrier protein) for any use described herein whether in the context of use as a medicament and/or use for manufacture of a medicament. Also provided are unit dosage forms of compositions described herein, articles of manufacture comprising the inventive compositions or unit dosage forms in suitable packaging (e.g., vials or vessels including sealed vials or vessels and sterile sealed vials or vessels), and kits comprising the unit dosage forms. The invention also provides methods of making and using these compositions as described herein.

It is to be understood that one, some, or all of the properties of the various embodiments described herein may be combined to form other embodiments of the present invention.

BRIEF DESCRIPTION OF FIGURES

FIG. 1 is a table listing the intravenous pharmacokinetic parameters for the albumin-containing nanoparticle formulation of rapamycin (hereinafter referred to as Nab-rapamycin).

FIG. 2A is a graph of Cmax versus dose, showing linearity for the Nab-rapamycin.

FIG. 2B is a graph of AUC versus dose, showing linearity for Nab-rapamycin.

FIG. 2C is a graph of Vss versus dose, showing possible saturable volume of distribution for Nab-rapamycin.

FIG. 2D is a graph showing the log-linear plot of Nab-rapamycin blood concentration vs. time following IV administration to rats at dose levels of 15 mg/kg, 30 mg/kg, and 45 mg/kg.

DETAILED DESCRIPTION OF THE INVENTION

Figures 3A, 3B:
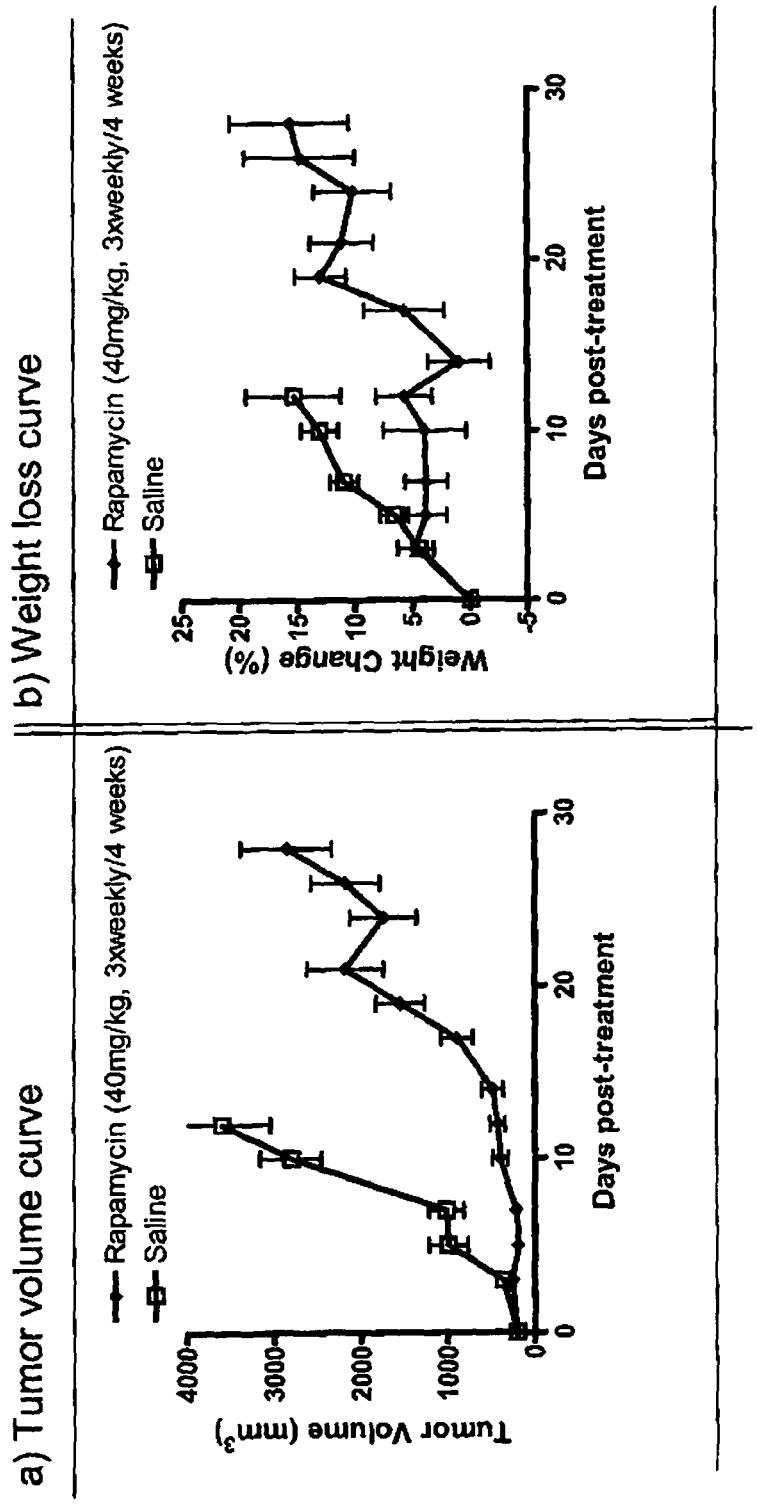
FIG. 3A is a graph of the antitumor activity of Nab-rapamycin in mice with MX-1 breast tumor xenografts.
FIG. 3B is a graph of the weight loss in mice with MX-1 breast tumor xenografts after the administration of Nab-rapamycin or saline.

The present invention provides methods, compositions, and kits for the treatment or prevention of cancer using nanoparticles that comprise rapamycin or a derivative thereof and a carrier protein (such as albumin). The present invention further provides methods, compositions, and kits for use in combination therapy for the treatment or prevention of cancer using nanoparticles that comprise rapamycin or a derivative thereof and a carrier protein (such as albumin). Any of these compositions can be used to treat, stabilize, prevent, and/or delay cancer.

In particular, nanoparticles comprising rapamycin (also referred to as a "nanoparticle composition") and the carrier protein albumin were shown to significantly inhibit the growth of a human mammary carcinoma implanted into a mouse model (Example 3) and inhibit tumor growth in mice with MM1S multiple myeloma tumor xenografts (Example 12B). This albumin-containing nanoparticle formulation of rapamycin was nontoxic at the doses tested and displayed linear pharmacokinetics with respect to dose (Example 2). The nanoparticle formulation of albumin and rapamycin enhances tumor penetration through albumin receptor (gp60)-mediated binding of the SPARC protein, which is upregulated in some cancer cells (e.g., breast cancer cells). This increased specificity of Nab-rapamycin may increase the effectiveness of rapamycin and may allow lower doses of rapamycin to be used, which would minimize toxic effects from rapamycin while still inhibiting, stabilizing, preventing, or delaying tumor growth. The increased specificity may also reduce toxic side-effects from interactions of rapamycin with noncancerous cells and tissues, such as intestinal toxicity that sometimes limits the dose of rapamycin that can be given to a patient. The nanoparticle formulation of rapamycin also increases the solubility of rapamycin and allows larger doses to be used, if desired.

Definitions

As used herein, "the composition" or "compositions" includes and is applicable to compositions of the invention. The invention also provides pharmaceutical compositions comprising the components described herein.

The term, "rapamycin" herein refers to rapamycin or its derivatives and accordingly the invention contemplates and includes all these embodiments. Rapamycin is sometimes referred to elsewhere as sirolimus, rapammune, or rapamune. Reference to "rapamycin" is to simplify the description and is exemplary. Derivatives of rapamycin include, but are not limited to, compounds that are structurally similar to rapamycin, or are in the same general chemical class as rapamycin, analogs of rapamycin, or pharmaceutically acceptable salts of rapamycin or its derivatives or analogs. In some embodiments, rapamycin or a derivative thereof increases basal AKT activity, increases AKT phosphorylation, increases PI3-kinase activity, increases the length of activation of AKT (e.g., activation induced by exogenous IGF-1), inhibits serine phosphorylation of IRS-1, inhibits IRS-1 degradation, inhibits or alters CXCR4 subcellular localization, inhibits VEGF secretion, decreases expression of cyclin D2, decreases expression of survivin, inhibits IL-6-induced multiple myeloma cell growth, inhibits cancer cell proliferation, increases apoptosis, increases cell cycle arrest, increases cleavage of poly(ADPribose) polymerase, increases cleavage of caspase-8/caspase-9, alters or inhibits signaling in the phosphatidylinositol 3-kinase/AKT/mTOR and/or cyclin D1/retinoblastoma pathways, inhibits angiogenesis, and/or inhibits osteoclast formation. In some embodiments, the derivative of rapamycin retains one or more similar biological, pharmacological, chemical and/or physical properties (including, for example, functionality) as rapamycin. In some embodiments, the rapamycin derivative has at least about any of 10%, 20%, 30%, 40%, 50%, 60%, 70%, 80%, 90%, 95% or 100% of an activity of rapamycin. For example, the decrease in the size of a tumor, the number of cancer cells, or the growth rate of a tumor caused by a rapamycin derivative is preferably at least about any of 10%, 20%, 30%, 40%, 50%, 60%, 70%, 80%, 90%, 95% or 100% of the corresponding decrease caused by the same amount of rapamycin. An exemplary rapamycin derivative includes benzoyl rapamycin, such as that disclosed in paragraph [0022] of WO 2006/089207, which is hereby incorporated by reference in its entirety. Other exemplary rapamycin derivatives include WY-090217, AY-22989, NSC-226080, SiiA-9268A, oxaazacyclohentriacontine, temsirolimus (CCI 779 (Wyeth)), everolimus (RAD 001 (Novartis)), pimecrolimus (ASM981), SDZ-RAD, SAR943, ABT-578, AP23573, and Biolimus A9.

Unless clearly indicated otherwise, "an individual" as used herein intends a mammal, including but not limited to a primate, human, bovine, horse, feline, canine, or rodent.

As used herein, "treatment" or "treating" is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsening of the disease), preventing or delaying the spread (e.g., metastasis) of the disease, preventing or delaying the occurrence or recurrence of the disease, delay or slowing the progression of the disease, ameliorating the disease state, providing a remission (whether partial or total) of the disease, decreasing the dose of one or more other medications required to treat the disease, delaying the progression of the disease, increasing the quality of life, and/or prolonging survival. In some embodiments, the composition reduces the severity of one or more symptoms associated with cancer by at least about any of 10%, 20%, 30%, 40%, 50%, 60%, 70%, 80%, 90%, 95% or 100% compared to the corresponding symptom in the same subject prior to treatment or compared to the corresponding symptom in other subjects not receiving the composition. Also encompassed by "treatment" is a reduction of pathological consequence of cancer. The methods of the invention contemplate any one or more of these aspects of treatment.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of subjects. Cancer development can be detectable using standard methods, such as routine physical exams, mammography, imaging, or biopsy. Development may also refer to disease progression that may be initially undetectable and includes occurrence, recurrence, and onset.

As used herein, an "at risk" individual is an individual who is at risk of developing cancer. An individual "at risk" may or may not have detectable disease, and may or may not have displayed detectable disease prior to the treatment methods described herein. "At risk" denotes that an individual has one or more so-called risk factors, which are measurable parameters that correlate with development of cancer, which are described herein. An individual having one or more of these risk factors has a higher probability of developing cancer than an individual without these risk factor(s).

"Adjuvant setting" refers to a clinical setting in which an individual has had a history of cancer, and generally (but not necessarily) been responsive to therapy, which includes, but is not limited to, surgery (e.g., surgical resection), radiotherapy, and chemotherapy. However, because of their history of the cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is be carried out before the primary/definitive therapy.

As used herein, by "pharmaceutically active compound" is meant a chemical compound that induces a desired effect, e.g., treating, stabilizing, preventing, and/or delaying cancer.

As used herein, by "combination therapy" is meant a first therapy that includes nanoparticles comprising rapamycin or a derivative thereof and a carrier protein in conjunction with a second therapy (e.g., radiation, surgery, or chemotherapeutic agent) useful for treating, stabilizing, preventing, and/or delaying cancer. Administration in "conjunction with" another compound includes administration in the same or different composition(s), either sequentially, simultaneously, or continuously. In some variations, the combination therapy optionally includes one or more pharmaceutically acceptable carriers or excipients, non-pharmaceutically active compounds, and/or inert substances.

The term "effective amount" intends such amount of a composition (e.g., nanoparticles that comprise rapamycin or a derivative thereof and a carrier protein), first therapy, second therapy, or a combination therapy, which in combination with its parameters of efficacy and toxicity, should be effective in a given therapeutic form based on the knowledge of the practicing specialist. In various embodiments, an effective amount of the composition or therapy may (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

In some embodiments, the amount of the composition, first therapy, second therapy, or combination therapy is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

As is understood in the art, an "effective amount" may be in one or more doses, i.e., a single dose or multiple doses may be required to achieve the desired treatment endpoint. An effective amount may be considered in the context of administering one or more therapeutic agents, and a nanoparticle composition (e.g., a composition including rapamycin and a carrier protein) may be considered to be given in an effective amount if, in conjunction with one or more other agents, a desirable or beneficial result may be or is achieved. The components (e.g., the first and second therapies) in a combination therapy of the invention may be administered sequentially, simultaneously, or continuously using the same or different routes of administration for each component. Thus, an effective amount of a combination therapy includes an amount of the first therapy and an amount of the second therapy that when administered sequentially, simultaneously, or continuously produces a desired outcome.

A "therapeutically effective amount" refers to an amount of a composition (e.g., nanoparticles that comprise rapamycin or a derivative thereof and a carrier protein), first therapy, second therapy, or a combination therapy sufficient to produce a desired therapeutic outcome (e.g., reducing the severity or duration of, stabilizing the severity of, or eliminating one or more symptoms of cancer). For therapeutic use, beneficial or desired results include, e.g., decreasing one or more symptoms resulting from the disease (biochemical, histologic and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients.

A "prophylactically effective amount" refers to an amount of a composition (e.g., nanoparticles that comprise rapamycin or a derivative thereof and a carrier protein), first therapy, second therapy, or a combination therapy sufficient to prevent or reduce the severity of one or more future symptoms of cancer when administered to an individual who is susceptible and/or who may develop cancer. For prophylactic use, beneficial or desired results include, e.g., results such as eliminating or reducing the risk, lessening the severity of future disease, or delaying the onset of the disease (e.g., delaying biochemical, histologic and/or behavioral symptoms of the disease, its complications, and intermediate pathological phenotypes presenting during future development of the disease).

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

The term "proteins" refers to polypeptides or polymers of amino acids of any length (including full length or fragments), which may be linear or branched, comprise modified amino acids, and/or be interrupted by non-amino acids. The term also encompasses an amino acid polymer that has been modified naturally or by intervention, including, for example, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally-occurring, i.e., obtained or derived from a natural source (e.g., blood) or synthesized (e.g., chemically synthesized or by synthesized by recombinant DNA techniques). Exemplary carrier proteins are described herein.

The term "antimicrobial agent" used herein refers to an agent that is capable of inhibiting (e.g., delaying, reducing, slowing, and/or preventing) the growth of one or more microorganisms. Significant microbial growth can be measured or indicated by a number of ways known in the art, such as one or more of the following: (i) microbial growth in a composition that is enough to cause one or more adverse effects to an individual when the composition is administered to the individual; (ii) more than about 10-fold increase in microbial growth over a certain period of time (for example over a 24 hour period) upon extrinsic contamination (e.g., exposure to 10-103 colony forming units at a temperature in the range of 20 to 25° C.). Other indicia of significant microbial growth are described in U.S. Ser. No. 11/514,030, filed Aug. 30, 2006, which is hereby incorporated by reference in its entirety.

"Sugar" as used herein includes, but is not limited to, monosaccharides, disaccharides, polysaccharides, and derivatives or modifications thereof. Suitable sugars for compositions described herein include, for example, mannitol, sucrose, fructose, lactose, maltose, and trehalose.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

As used herein, reference to "not" a value or parameter generally means and describes "other than" a value or parameter. For example, if a taxane is not administered, it means an agent other than a taxane is administered.

Reference to "about" a value or parameter herein includes (and describes) embodiments that are directed to that value or parameter per se. For example, description referring to "about X" includes description of "X".

As used herein and in the appended claims, the singular forms "a," "or," and "the" include plural referents unless the context clearly dictates otherwise. It is understood that aspect and embodiments of the invention described herein include "consisting" and/or "consisting essentially of aspects and embodiments.

Methods of Treating Cancer

The invention provides methods of treating cancer in an individual (e.g., human) comprising administering to the individual an effective amount of a composition comprising nanoparticles comprising rapamycin or a derivative thereof and a carrier protein (e.g., albumin). The present invention provides a method of treating cancer in an individual (e.g., human) comprising administering to the individual an effective amount of a composition comprising nanoparticles comprising rapamycin and an albumin. The therapy may be monotherapy or in a combination therapy context. Additionally, the invention provides a method of treating cancer in an individual by administering to the individual an effective amount of a combination of a) a first therapy that comprises a composition comprising nanoparticles that comprise rapamycin or a derivative thereof and a carrier protein (e.g., albumin) and b) a second therapy useful for treating cancer. In some embodiments, the second therapy includes surgery, radiation, gene therapy, immunotherapy, bone marrow transplantation, stem cell transplantation, hormone therapy, targeted therapy, cryotherapy, ultrasound therapy, photodynamic therapy, and/or chemotherapy (e.g., one or more compounds useful for treating cancer). It is understood that reference to and description of methods of treating cancer below is exemplary and that this description applies equally to and includes methods of treating cancer using combination therapy.

Examples of cancers that may be treated by the methods of the invention include, but are not limited to, adenocortical carcinoma, agnogenic myeloid metaplasia, AIDS-related cancers (e.g., AIDS-related lymphoma), anal cancer, appendix cancer, astrocytoma (e.g., cerebellar and cerebral), basal cell carcinoma, bile duct cancer (e.g., extrahepatic), bladder cancer, bone cancer, (osteosarcoma and malignant fibrous histiocytoma), brain tumor (e.g., glioma, brain stem glioma, cerebellar or cerebral astrocytoma (e.g., pilocytic astrocytoma, diffuse astrocytoma, anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, and glioblastoma), breast cancer, bronchial adenomas/carcinoids, carcinoid tumor (e.g., gastrointestinal carcinoid tumor), carcinoma of unknown primary, central nervous system lymphoma, cervical cancer, colon cancer, colorectal cancer, chronic myeloproliferative disorders, endometrial cancer (e.g., uterine cancer), ependymoma, esophageal cancer, Ewing's family of tumors, eye cancer (e.g., intraocular melanoma and retinoblastoma), gallbladder cancer, gastric (stomach) cancer, gastrointestinal carcinoid tumor, gastrointestinal stromal tumor (GIST), germ cell tumor, (e.g., extracranial, extragonadal, ovarian), gestational trophoblastic tumor, head and neck cancer, hepatocellular (liver) cancer (e.g., hepatic carcinoma and heptoma), hypopharyngeal cancer, islet cell carcinoma (endocrine pancreas), laryngeal cancer, laryngeal cancer, leukemia, lip and oral cavity cancer, oral cancer, liver cancer, lung cancer (e.g., small cell lung cancer, non-small cell lung cancer, adenocarcinoma of the lung, and squamous carcinoma of the lung), lymphoid neoplasm (e.g., lymphoma), medulloblastoma, melanoma, mesothelioma, metastatic squamous neck cancer, mouth cancer, multiple endocrine neoplasia syndrome, myelodysplastic syndromes, myelodysplastic/myeloproliferative diseases, nasal cavity and paranasal sinus cancer, nasopharyngeal cancer, neuroblastoma, neuroendocrine cancer, oropharyngeal cancer, ovarian cancer (e.g., ovarian epithelial cancer, ovarian germ cell tumor, ovarian low malignant potential tumor), pancreatic cancer, parathyroid cancer, penile cancer, cancer of the peritoneal, pharyngeal cancer, pheochromocytoma, pineoblastoma and supratentorial primitive neuroectodermal tumors, pituitary tumor, pleuropulmonary blastoma, lymphoma, primary central nervous system lymphoma (microglioma), pulmonary lymphangiomyomatosis, rectal cancer, renal cancer, renal pelvis and ureter cancer (transitional cell cancer), rhabdomyosarcoma, salivary gland cancer, skin cancer (e.g., nonmelanoma (e.g., squamous cell carcinoma), melanoma, and Merkel cell carcinoma), small intestine cancer, squamous cell cancer, testicular cancer, throat cancer, thymoma and thymic carcinoma, thyroid cancer, tuberous sclerosis, urethral cancer, vaginal cancer, vulvar cancer, Wilms' tumor, and post-transplant lymphoproliferative disorder (PTLD), abnormal vascular proliferation associated with phakomatoses, edema (such as that associated with brain tumors), and Meigs' syndrome.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is a lymphoid neoplasm (e.g., lymphoma). In some embodiments, there are provided methods of treating cancer in an individual by administering to the individual (e.g., a human) an effective amount of a composition comprising nanoparticles comprising a rapamycin and an albumin, wherein the cancer is a lymphoid neoplasm (e.g., lymphoma).

In some embodiments the lymphoid neoplasm (e.g., lymphoma) is a B-cell neoplasm. Examples of B-cell neoplasms include, but are not limited to, precursor B-cell neoplasms (e.g., precursor B-lymphoblastic leukemia/lymphoma) and peripheral B-cell neoplasms (e.g., B-cell chronic lymphocytic leukemia/prolymphocytic leukemia/small lymphocytic lymphoma (small lymphocytic (SL) NHL), lymphoplasmacytoid lymphoma/immunocytoma, mantel cell lymphoma, follicle center lymphoma, follicular lymphoma (e.g., cytologic grades: I (small cell), II (mixed small and large cell), III (large cell) and/or subtype: diffuse and predominantly small cell type), low grade/follicular non-Hodgkin's lymphoma (NHL), intermediate grade/follicular NHL, marginal zone B-cell lymphoma (e.g., extranodal (e.g., MALT-type +/− monocytoid B cells) and/or Nodal (e.g., +/− monocytoid B cells)), splenic marginal zone lymphoma (e.g., +/− villous lymphocytes), Hairy cell leukemia, plasmacytoma/plasma cell myeloma (e.g., myeloma and multiple myeloma), diffuse large B-cell lymphoma (e.g., primary mediastinal (thymic) B-cell lymphoma), intermediate grade diffuse NHL, Burkitt's lymphoma, High-grade B-cell lymphoma, Burkitt-like, high grade immunoblastic NHL, high grade lymphoblastic NHL, high grade small non-cleaved cell NHL, bulky disease NHL, AIDS-related lymphoma, and Waldenstrom's macroglobulinemia).

In some embodiments the lymphoid neoplasm (e.g., lymphoma) is a T-cell and/or putative NK-cell neoplasm. Examples of T-cell and/or putative NK-cell neoplasms include, but are not limited to, precursor T-cell neoplasm (precursor T-lymphoblastic lymphoma/leukemia) and peripheral T-cell and NK-cell neoplasms (e.g., T-cell chronic lymphocytic leukemia/prolymphocytic leukemia, and large granular lymphocyte leukemia (LGL) (e.g., T-cell type and/or NK-cell type), cutaneous T-cell lymphoma (e.g., mycosis fungoides/Sezary syndrome), primary T-cell lymphomas unspecified (e.g., cytological categories (e.g., medium-sized cell, mixed medium and large cell), large cell, lymphoepitheloid cell, subtype hepatosplenic γδ T-cell lymphoma, and subcutaneous panniculitic T-cell lymphoma), angioimmunoblastic T-cell lymphoma (AILD), angiocentric lymphoma, intestinal T-cell lymphoma (e.g., +/− enteropathy associated), adult T-cell lymphoma/leukemia (ATL), anaplastic large cell lymphoma (ALCL) (e.g., CD30+, T- and null-cell types), anaplastic large-cell lymphoma, and Hodgkin's like).

In some embodiments the lymphoid neoplasm (e.g., lymphoma) is Hodgkin's disease. For example, the Hodgkin's disease may be lymphocyte predominance, nodular sclerosis, mixed cellularity, lymphocyte depletion, and/or lymphocyte-rich.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is leukemia. In some embodiments, there are provided methods of treating cancer in an individual by administering to the individual (e.g., a human) an effective amount of a composition comprising nanoparticles comprising a rapamycin and an albumin, wherein the cancer is leukemia. In some embodiments, the leukemia is chronic leukemia. Examples of chronic leukemia include, but are not limited to, chronic myelocytic I (granulocytic) leukemia, chronic myelogenous, and chronic lymphocytic leukemia (CLL). In some embodiments, the leukemia is acute leukemia. Examples of acute leukemia include, but are not limited to, acute lymphoblastic leukemia (ALL), acute myeloid leukemia, acute lymphocytic leukemia, and acute myelocytic leukemia (e.g., myeloblastic, promyelocytic, myelomonocytic, monocytic, and erythroleukemia).

In some embodiments, there are provided methods of treating cancer with compositions comprising nanoparticles comprising rapamycin or a derivative thereof and a carrier protein (e.g., albumin), wherein the cancer is a liquid tumor or plasmacytoma. In some embodiments, there are provided methods of treating cancer in an individual by administering to the individual (e.g., a human) an effective amount of a composition comprising nanoparticles comprising a rapamycin and an albumin, wherein the cancer is a liquid tumor or plasmacytoma. Plasmacytoma includes, but is not limited to, myeloma. Myeloma includes, but is not limited to, an extramedullary plasmacytoma, a solitary myeloma, and multiple myeloma. In some embodiments, the plasmacytoma is multiple myeloma.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is multiple myeloma. In some embodiments, there are provided methods of treating cancer in an individual by administering to the individual (e.g., a human) an effective amount of a composition comprising nanoparticles comprising a rapamycin and an albumin, wherein the cancer is multiple myeloma. Examples of multiple myeloma include, but are not limited to, IgG multiple myeloma, IgA multiple myeloma, IgD multiple myeloma, IgE multiple myeloma, and nonsecretory multiple myeloma. In some embodiments, the multiple myeloma is IgG multiple myeloma. In some embodiments, the multiple myeloma is IgA multiple myeloma. In some embodiments, the multiple myeloma is a smoldering or indolent multiple myeloma. In some embodiments, the multiple myeloma is progressive multiple myeloma. In some embodiments, multiple myeloma may be resistant to a drug, such as, but not limited to, bortezomib, dexamethasone (Dex-), doxorubicin (Dox-), and melphalan (LR).

In some embodiments, the individual may be a human who has a gene, genetic mutation, or polymorphism associated with multiple myeloma (e.g., ras, PTEN, Rb1, MTS1/p16INK4A/ CDKN2, MTS2/p15INK4B, and/or p53) or has one or more extra copies of a gene associated with multiple myeloma. In some embodiments, the individual has a ras or PTEN mutation. In some embodiments, the cancer cells are dependent on an mTOR pathway to translate one or more mRNAs. In some embodiments, the cancer cells are not capable of synthesizing mRNAs by an mTOR-independent pathway. In some embodiments, the cancer cells have decreased or no PTEN activity or have decreased or no expression of PTEN compared to non-cancerous cells. In some embodiments, the cancer cells have increased AKT activity and/or expression compared to non-cancerous cells.

In some embodiments, there are provided methods of treating cancer in an individual by administering to the individual (e.g., a human) an effective amount of a composition comprising nanoparticles of rapamycin or a derivative thereof and a carrier protein (e.g., albumin), wherein the cancer is a solid tumor. In some embodiments, there are provided methods of treating cancer in an individual by administering to the individual (e.g., a human) an effective amount of a composition comprising nanoparticles comprising a rapamycin and an albumin, wherein the cancer is a solid tumor. In some embodiments, the solid tumor includes, but is not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, Kaposi's sarcoma, soft tissue sarcoma, uterine sacronomasynovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Accordingly, in some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is breast cancer. In some embodiments, there are provided a method of treating breast cancer in an individual by administering to the individual (e.g., a human) an effective amount of a composition comprising nanoparticles that comprise rapamycin or a derivative thereof and an albumin. In some embodiments, the breast cancer is early stage breast cancer, non-metastatic breast cancer, advanced breast cancer, stage IV breast cancer, locally advanced breast cancer, metastatic breast cancer, breast cancer in remission, breast cancer in an adjuvant setting, or breast cancer in a neoadjuvant setting. In some specific embodiments, the breast cancer is in a neoadjuvant setting. In some embodiments, there are provided methods of treating cancer at advanced stage(s). In some embodiments, there are provided methods of treating breast cancer (which may be HER2 positive or HER2 negative), including, for example, advanced breast cancer, stage IV breast cancer, locally advanced breast cancer, and metastatic breast cancer. In some embodiments, the individual may be a human who has a gene, genetic mutation, or polymorphism associated with breast cancer (e.g., BRCA1, BRCA2, ATM, CHEK2, RAD51, AR, DIRAS3, ERBB2, TP53, AKT, PTEN, and/or PI3K) or has one or more extra copies of a gene (e.g., one or more extra copies of the HER2 gene) associated with breast cancer. In some embodiments, the method further comprises identifying a cancer patient population (i.e. breast cancer population) based on a hormone receptor status of patients having tumor tissue not expressing both ER and PgR and administering to the patient population an effective amount of a composition comprising nanoparticles comprising rapamycin or a derivative thereof and a carrier protein (e.g., albumin)

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is a renal cell carcinoma (also called kidney cancer, renal adenocarcinoma, or hypernephroma). In some embodiments, there are provided methods of treating cancer by administering to the individual (e.g., a human) an effective amount of a composition comprising nanoparticles comprising an albumin, wherein the cancer is a renal cell carcinoma. In some embodiments, the renal cell carcinoma is an adenocarcinoma. In some embodiments, the renal cell carcinoma is a clear cell renal cell carcinoma, papillary renal cell carcinoma (also called chromophilic renal cell carcinoma), chromophobe renal cell carcinoma, collecting duct renal cell carcinoma, granular renal cell carcinoma, mixed granular renal cell carcinoma, renal angiomyolipomas, or spindle renal cell carcinoma. In some embodiments, the individual may be a human who has a gene, genetic mutation, or polymorphism associated with renal cell carcinoma (e.g., VHL, TSC1, TSC2, CUL2, MSH2, MLH1, INK4a/ARF, MET, TGF-α, TGF-β1, IGF-1, IGF-1R, AKT, and/or PTEN) or has one or more extra copies of a gene associated with renal cell carcinoma. In some embodiments, the renal cell carcinoma is associated with (1) von Hippel-Lindau (VHL) syndrome, (2) hereditary papillary renal carcinoma (HPRC), (3) familial renal oncocytoma (FRO) associated with Birt-Hogg-Dube syndrome (BHDS), or (4) hereditary renal carcinoma (HRC). There are provided methods of treating renal cell carcinoma at any of the four stages, I, II, III, or IV, according to the American Joint Committee on Cancer (AJCC) staging groups. In some embodiments, the renal cell carcinoma is stage IV renal cell carcinoma.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is prostate cancer. In some embodiments, there are provided methods of treating cancer by administering to the individual (e.g., a human) an effective amount of a composition comprising nanoparticles comprising a rapamycin and an albumin, wherein the cancer is prostate cancer. In some embodiments, the prostate cancer is an adenocarcinoma. In some embodiments, the prostate cancer is a sarcoma, neuroendocrine tumor, small cell cancer, ductal cancer, or a lymphoma. There are provided methods of treating prostate cancer at any of the four stages, A, B, C, or D, according to the Jewett staging system. In some embodiments, the prostate cancer is stage A prostate cancer (The cancer cannot be felt during a rectal exam.). In some embodiments, the prostate cancer is stage B prostate cancer (The tumor involves more tissue within the prostate, it can be felt during a rectal exam, or it is found with a biopsy that is done because of a high PSA level.). In some embodiments, the prostate cancer is stage C prostate cancer (The cancer has spread outside the prostate to nearby tissues.). In some embodiments, the prostate cancer is stage D prostate cancer. In some embodiments, the prostate cancer may be androgen independent prostate cancer (AIPC). In some embodiments, the prostate cancer may be androgen dependent prostate cancer. In some embodiments, the prostate cancer may be refractory to hormone therapy. In some embodiments, the prostate cancer may be substantially refractory to hormone therapy. In some embodiments, the individual may be a human who has a gene, genetic mutation, or polymorphism associated with prostate cancer (e.g., RNA-SEL/HPC1, ELAC2/HPC2, SR-A/MSR1, CHEK2, BRCA2, PON1, OGG1, MICA-1, TLR4, and/or PTEN) or has one or more extra copies of a gene associated with prostate cancer.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is lung cancer. In some embodiments, there are provided methods of treating cancer by administering to the individual (e.g., a human) an effective amount of a composition comprising nanoparticles comprising a rapamycin and an albumin, wherein the cancer is lung cancer. In some embodiments, the cancer is lung cancer is a non-small cell lung cancer (NSCLC). Examples of NCSLC include, but are not limited to, large-cell carcinoma (e.g., large-cell neuroendocrine carcinoma, combined large-cell neuroendocrine carcinoma, basaloid carcinoma, lymphoepithelioma-like carcinoma, clear cell carcinoma, and large-cell carcinoma with rhabdoid phenotype), adenocarcinoma (e.g., acinar, papillary (e.g., bronchioloalveolar carcinoma, nonmucinous, mucinous, mixed mucinous and nonmucinous and indeterminate cell type), solid adenocarcinoma with mucin, adenocarcinoma with mixed subtypes, well-differentiated fetal adenocarcinoma, mucinous (colloid) adenocarcinoma, mucinous cystadenocarcinoma, signet ring adenocarcinoma, and clear cell adenocarcinoma), neuroendocrine lung tumors, and squamous cell carcinoma (e.g., papillary, clear cell, small cell, and basaloid). In some embodiments, the NSCLC may be, according to TNM classifications, a stage T tumor (primary tumor), a stage N tumor (regional lymph nodes), or a stage M tumor (distant metastasis). In some embodiments, the lung cancer is a carcinoid (typical or atypical), adenosquamous carcinoma, cylindroma, or carcinoma of the salivary gland (e.g., adenoid cystic carcinoma or mucoepidermoid carcinoma). In some embodiments, the lung cancer is a carcinoma with pleomorphic, sarcomatoid, or sarcomatous elements (e.g., carcinomas with spindle and/or giant cells, spindle cell carcinoma, giant cell carcinoma, carcinosarcoma, or pulmonary blastoma). In some embodiments, the cancer is small cell lung cancer (SCLC; also called oat cell carcinoma). The small cell lung cancer may be limited-stage, extensive stage or reoccurent small cell lung cancer. In some embodiments, the individual may be a human who has a gene, genetic mutation, or polymorphism suspected or shown to be associated with lung cancer (e.g., SASH1, LATS1, IGF2R, PARK2, KRAS, PTEN, Kras2, Krag, Pas1, ERCC1, XPD, IL8RA, EGFR, $\alpha_1$-AD, EPHX, MMP1, MMP2, MMP3, MMP12, IL1β, RAS, and/or AKT) or has one or more extra copies of a gene associated with lung cancer.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is brain cancer. In some embodiments, there are provided methods of treating cancer by administering to the individual (e.g., a human) an effective amount of a composition comprising nanoparticles comprising a rapamycin and an albumin, wherein the cancer is brain cancer. In some embodiments, the brain cancer is glioma, brain stem glioma, cerebellar or cerebral astrocytoma (e.g., pilocytic astrocytoma, diffuse astrocytoma, or anaplastic (malignant) astrocytoma), malignant glioma, ependymoma, oligodenglioma, meningioma, craniopharyngioma, haemangioblastomas, medulloblastoma, supratentorial primitive neuroectodermal tumors, visual pathway and hypothalamic glioma, or glioblastoma. In some embodiments, the brain cancer is glioblastoma (also called glioblastoma multiforme or grade 4 astrocytoma). In some embodiments, the glioblastoma is radiation-resistant. In some embodiments, the glioblastoma is radiation-sensitive. In some embodiments, the glioblastoma may be infratentorial. In some embodiments, the glioblastoma is supratentorial. In some embodiments, the individual may be a human who has a gene, genetic mutation, or polymorphism associated with brain cancer (e.g., glioblastoma) (e.g., NRPB, MAGE-E1, MMACI-E1, PTEN, LOH, p53, MDM2, DCC, TP-73, Rb1, EGFR, PDGFR-α, PMS2, MLH1, and/or DMBT1) or has one or more extra copies of a gene associated with brain cancer (e.g., glioblastoma) (e.g., MDM2, EGFR, and PDGR-α).

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is melanoma. In some embodiments, there are provided methods of treating cancer by administering to the individual (e.g., a human) an effective amount of a composition comprising nanoparticles comprising a rapamycin and an albumin, wherein the cancer is melanoma.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is ovarian cancer. In some embodiments, there are provided methods of treating cancer by administering to the individual (e.g., a human) an effective amount of a composition comprising nanoparticles comprising a rapamycin and an albumin, wherein the cancer is ovarian cancer. In some embodiments, the cancer is ovarian epithelial cancer. Exemplary ovarian epithelial cancer histological classifications include: serous cystomas (e.g., serous benign cystadenomas, serous cystadenomas with proliferating activity of the epithelial cells and nuclear abnormalities but with no infiltrative destructive growth, or serous cystadenocarcinomas), mucinous cystomas (e.g., mucinous benign cystadenomas, mucinous cystadenomas with proliferating activity of the epithelial cells and nuclear abnormalities but with no infiltrative destructive growth, or mucinous cystadenocarcinomas), endometrioid tumors (e.g., endometrioid benign cysts, endometrioid tumors with proliferating activity of the epithelial cells and nuclear abnormalities but with no infiltrative destructive growth, or endometrioid adenocarcinomas), clear cell (mesonephroid) tumors (e.g., begin clear cell tumors, clear cell tumors with proliferating activity of the epithelial cells and nuclear abnormalities but with no infiltrative destructive growth, or clear cell cystadenocarcinomas), unclassified tumors that cannot be allotted to one of the above groups, or other malignant tumors. In various embodiments, the ovarian epithelial cancer is stage I (e.g., stage IA, IB, or IC), stage II (e.g., stage IIA, IIB, or IIC), stage III (e.g., stage IIIA, IIIB, or IIIC), or stage IV. In some embodiments, the individual may be a human who has a gene, genetic mutation, or polymorphism associated with ovarian cancer (e.g., BRCA1 or BRCA2) or has one or more extra copies of a gene associated with ovarian cancer (e.g., one or more extra copies of the HER2 gene).

In some embodiments, the cancer is an ovarian germ cell tumor. Exemplary histologic subtypes include dysgerminomas or other germ cell tumors (e.g., endodermal sinus tumors such as hepatoid or intestinal tumors, embryonal carcinomas, olyembryomas, choriocarcinomas, teratomas, or mixed form tumors). Exemplary teratomas are immature teratomas, mature teratomas, solid teratomas, and cystic teratomas (e.g., dermoid cysts such as mature cystic teratomas, and dermoid cysts with malignant transformation). Some teratomas are monodermal and highly specialized, such as struma ovarii, carcinoid, struma ovarii and carcinoid, or others (e.g., malignant neuroectodermal and ependymomas). In some embodiments, the ovarian germ cell tumor is stage I (e.g., stage IA, IB, or IC), stage II (e.g., stage IIA, IIB, or IIC), stage III (e.g., stage IIIA, IIIB, or IIIC), or stage IV.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is a neuroendocrine cancer. In some embodiments, the individual may be a human who has a gene, genetic mutation, or polymorphism associated with neuroendocrine cancer (e.g., TSC1, TSC2, IGF-1, IGF-1R, and/or VHL) or has one or more extra copies of a gene associated with neurondocrine cancer.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is colon cancer. In some embodiments, the individual may be a human who has a gene, genetic mutation, or polymorphism associated with colon cancer (e.g., RAS, AKT, PTEN, PI3K, and/or EGFR) or has one or more extra copies of a gene associated with colon cancer.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by PI3K and/or AKT activation. In some embodiments, the cancer characterized by PI3K and/or AKT activation is HER2$^+$ breast cancer, chronic myelogenous leukemia, ovarian cancer, endometrial cancer, sarcoma, squamous cell carcinoma of the head and neck, or thyroid cancer. In some variations, the cancer is further characterized by AKT gene amplification.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by cyclin D1 overexpression. In some embodiments, the cancer characterized by cyclin D overexpression is mantle cell lymphoma or breast cancer.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by cMYC overexpression. In some embodiments, the cancer characterized by cMYC overexpression is Burkitt lymphoma.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by HIF overexpression. In some embodiments, the cancer characterized by HIF overexpression is renal cell carcinoma or Von Hippel-Lindau. In some embodiments, the cancer further comprises a VHL mutation.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by TSC1 and/or TSC2 loss. In some embodiments, the cancer characterized by TSC1 and/or TSC2 is tuberous sclerosis or pulmonary lymphangiomyomatosis.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by a TSC2 mutation. In some embodiments, the cancer characterized by TSC2 mutation is renal angiomyolipomas.

In some embodiments, there are provided methods of treating cancer in an individual by administering to the individual (e.g., a human) an effective amount of a composition comprising nanoparticles comprising rapamycin or a derivative thereof and a carrier protein (e.g., albumin), wherein the cancer is characterized by a PTEN mutation. In some embodiments, the PTEN mutation is a loss of PTEN function. In some embodiments, the cancer characterized by a PTEN mutation is glioblastoma, endometrial cancer, prostate cancer, sarcoma, or breast cancer.

In some embodiments, the methods of treatment provided herein may also be used to treat a cancer which is not a solid tumor (i.e., other than a solid tumor). In some embodiments, the methods of treatment provided herein may also be used to treat a cancer which is not a carcinoma. In some embodiments, the methods of treatment provided herein may also be used to treat a cancer which is not a sarcoma. In some embodiments, the methods of treatment provided herein may also be used to treat a cancer which is not a lymphoma. In some embodiments, the methods of treatment provided herein may also be used to treat a cancer which is not colon cancer (i.e., other than colon cancer). In some embodiments, the methods of treatment provided herein may also be used to treat a cancer which is not breast cancer (i.e., other than breast cancer). In some embodiments, the methods of treatment provided herein may also be used to treat a cancer which is not an ovarian cancer, brain cancer, and/or prostate cancer (i.e., other than ovarian cancer, brain cancer, and/or prostate cancer).

Any of the methods of treatment provided herein may be used to treat a primary tumor. Any of the methods of treatment provided herein may also be used to treat a metastatic cancer (that is, cancer that has metastasized from the primary tumor). Any of the methods of treatment provided herein may be used to treat cancer at an advanced stage. Any of the methods of treatment provided herein may be used to treat cancer at a locally advanced stage. Any of the methods of treatment provided herein may be used to treat early stage cancer. Any of the methods of treatment provided herein may be used to treat cancer in remission. In some of the embodiments of any of the methods of treatment provided herein, the cancer has reoccurred after remission. In some embodiments of any of the methods of treatment provided herein, the cancer is progressive cancer. Any of the methods of treatment provided herein may be used to treat cancer substantially refractory to hormone therapy. Any of the methods of treatment provided herein may be used to treat HER-2 positive cancer. Any of the methods of treatment provided herein may be used to treat HER-2 negative cancer.

Any of the methods of treatment provided herein may be used to treat and individual (e.g., human) who has been diagnosed with or is suspected of having cancer. In some embodiments, the individual may be a human who exhibits one or more symptoms associated with cancer. In some embodiments, the individual may have advanced disease or a lesser extent of disease, such as low tumor burden. In some embodiments, the individual is at an early stage of a cancer. In some embodiments, the individual is at an advanced stage of cancer. In some of the embodiments of any of the methods of treatment provided herein, the individual may be a human who is genetically or otherwise predisposed (e.g., risk factor) to developing cancer who has or has not been diagnosed with cancer. In some embodiments, these risk factors include, but are not limited to, age, sex, race, diet, history of previous disease, presence of precursor disease, genetic (e.g., hereditary) considerations, and environmental exposure. In some embodiments, the individuals at risk for cancer include, e.g., those having relatives who have experienced this disease, and those whose risk is determined by analysis of genetic or biochemical markers.

Any of the methods of treatment provided herein may be practiced in an adjuvant setting. Any of the methods of treatment provided herein may be practiced in a neoadjuvant setting, i.e., the method may be carried out before the primary/definitive therapy. In some embodiments, any of the methods of treatment provided herein may be used to treat an individual who has previously been treated. Any of the methods of treatment provided herein may be used to treat an individual who has not previously been treated. Any of the methods of treatment provided herein may be used to treat an individual at risk for developing cancer, but has not been diagnosed with cancer. Any of the methods of treatment provided herein may be used as a first line therapy. Any of the methods of treatment provided herein may be used as a second line therapy.

In some embodiments of any of the methods of treatment provided herein, a taxane is not administered to the individual. In some embodiments, the taxane administered is not a nanoparticle composition. In some embodiments, the nanoparticle composition comprising rapamycin or a derivative thereof is not administered in conjunction with a taxane. In some embodiments, a taxane is not administered to the individual during the time period in which the individual is receiving one or more doses of a nanoparticle composition comprising rapamycin or a derivative thereof In some embodiments, the individual was treated with a taxane before treatment begins with a nanoparticle composition comprising rapamycin or a derivative thereof For example, the individual may have received a taxane one or more days, weeks, months, or years before treatment begins with a nanoparticle composition comprising rapamycin or a derivative thereof In other embodiments, the individual never receives a taxane before treatment begins with a nanoparticle composition comprising rapamycin or a derivative thereof In some embodiments, the individual is treated with a taxane after treatment with a nanoparticle composition comprising rapamycin or derivative thereof terminates. In other embodiments, the individual is never treated with a taxane after treatment with a nanoparticle composition comprising rapamycin or derivative thereof terminates. In some embodiments, the composition, first therapy, and/or second therapy do not contain a taxane. In other embodiments, the composition, first therapy, and/or second therapy comprise a taxane. In some embodiments, the first and/or second therapies do not comprise a SPARC polypeptide or anti-SPARC antibody (i.e., other than. SPARC polypeptide or anti-SPARC antibody).

Any of the methods of treatment provided herein may be used to treat, stabilize, prevent, and/or delay any type or stage of cancer. In some embodiments, the individual is at least about any of 40, 45, 50, 55, 60, 65, 70, 75, 80, or 85 years old. In some embodiments, one or more symptoms of the cancer are ameliorated or eliminated. In some embodiments, the size of a tumor, the number of cancer cells, or the growth rate of a tumor decreases by at least about any of 10%, 20%, 30%, 40%, 50%, 60%, 70%, 80%, 90%, 95% or 100%. In some embodiments, the cancer is delayed or prevented.

Combination Therapy

The present invention also features methods for the treatment of cancer using combination therapies. Accordingly, in some embodiments, a second therapy useful for treating cancer is also administered to the individual. In some embodiments, the second therapy includes surgery, radiation, gene therapy, immunotherapy, bone marrow transplantation, stem cell transplantation, hormone therapy, targeted therapy, cryotherapy, ultrasound therapy, photodynamic therapy, and/or chemotherapy (e.g., one or more compounds or pharmaceutically acceptable salts thereof useful for treating cancer). It is understood that reference to and description of methods of treating cancer above is exemplary and that the description applies equally to and includes methods of treating cancer using combination therapy.

In one such aspect, the invention provides a method of treating cancer in an individual by administering to the individual an effective amount of a combination of a) a first therapy that includes a composition comprising nanoparticles that include rapamycin or a derivative thereof and a carrier protein (e.g., albumin) and b) a second therapy useful for treating cancer. In some embodiments, the second therapy includes surgery, radiation, gene therapy, immunotherapy, bone marrow transplantation, stem cell transplantation, hormone therapy, targeted therapy, cryotherapy, ultrasound therapy, photodynamic therapy, and/or chemotherapy (e.g., one or more compounds useful for treating cancer). In some embodiments, the first and/or second therapies do not include a taxane. In other embodiments, the first and/or second therapies do include a taxane. In some embodiments, the first and/or second therapies do not comprise a SPARC polypeptide or anti-SPARC antibody.

In some embodiments, the invention provides methods of treating cancer in an individual, comprising administering to the individual a) an effective amount of a composition comprising nanoparticles comprising a rapamycin or a derivative thereof and a carrier protein (e.g., albumin); and b) an effective amount of at least one other chemotherapeutic agent. In some embodiments, the nanoparticles comprise rapamycin and an albumin. In some embodiments, the chemotherapeutic agent is any of (and in some embodiments selected from the group consisting of) antimetabolite agents (including nucleoside analogs), platinum-based agents, alkylating agents, tyrosine kinase inhibitors, anthracycline antibiotics, vinca alkloids, proteasome inhibitors, taxanes, modulators of HER2/neu (such as inhibitors of HER2/neu for example Herceptin®), modulators of EGFR (such as inhibitors of EGFR for example Erbitux®), modulators of VEGFR, farnosyltransferase inhibitors, and topoisomerase inhibitors. In some embodiments, the chemotherapeutic is not a taxane (i.e., the compound is a chemotherapeutic agent other than a taxane). Preferred drug combinations for sequential or co-administration or simultaneous administration with nanoparticles comprising a rapamycin or a derivative thereof and a carrier protein (e.g., albumin) are those which show enhanced anticancer activity when compared with the single components alone, especially combinations that lead to regression of cancer and/or cure from cancer.

The chemotherapeutic agents described herein can be the agents themselves, pharmaceutically acceptable salts thereof, and pharmaceutically acceptable esters thereof, as well as stereoisomers, enantiomers, racemic mixtures, and the like. The chemotherapeutic agent or agents as described can be administered as well as a pharmaceutical composition containing the agent(s), wherein the pharmaceutical composition comprises a pharmaceutically acceptable carrier vehicle, or the like.

The chemotherapeutic agent may be present in a nanoparticle composition. For example, in some embodiments, there is provided a method of treating cancer in an individual, comprising administering to the individual a) an effective amount of a composition comprising nanoparticles comprising a rapamycin or a derivative thereof and a carrier protein (e.g., albumin); and b) an effective amount of a composition comprising nanoparticles comprising at least one other chemotherapeutic agent and a carrier protein (such as albumin). In some embodiments, the method comprises administering to the individual a) an effective amount of a composition comprising nanoparticles comprising a rapamycin and an albumin; and b) an effective amount of a composition comprising nanoparticles comprising at least one other chemotherapeutic agent and a carrier protein (such as albumin). In some embodiments, the chemotherapeutic agent is any of (and in some embodiments selected from the group consisting of) thiocolchicine or its derivatives (such as dimeric thiocolchicine, including for example nab-5404, nab-5800, and nab-5801), and geldanamycin or its derivatives (such as 17-allyl amino geldanamycin (17-AAG)). In some embodiments, the chemotherapeutic agent is a taxane or a derivative thereof (e.g., paclitaxel, docetaxel, and ortataxel). In some embodiments, the chemotherapeutic agent is not a taxane. In other embodiments, the chemotherapeutic is not a taxane. In some embodiments, the chemotherapeutic agent is 17-AAG. In some embodiments, the chemotherapeutic agent is dimeric thiocolchicine.

An exemplary and non-limiting list of chemotherapeutic agents contemplated is provided herein. Suitable chemotherapeutic agents include, for example, vinca alkaloids, agents that disrupt microtubule formation (such as colchicines and its derivatives), anti-angiogenic agents, therapeutic antibodies, EGFR targeting agents, tyrosine kinase targeting agent (such as tyrosine kinase inhibitors), transitional metal complexes, proteasome inhibitors, antimetabolites (such as nucleoside analogs), alkylating agents, platinum-based agents, anthracycline antibiotics, topoisomerase inhibitors, therapeutic antibodies, retinoids (such as all-trans retinoic acids or a derivatives thereof); geldanamycin or a derivative thereof (such as 17-AAG), and other standard chemotherapeutic agents well recognized in the art.

In some embodiments, the chemotherapeutic agent is any of (and in some embodiments selected from the group consisting of) adriamycin, colchicine, cyclophosphamide, actinomycin, bleomycin, duanorubicin, doxorubicin, epirubicin, mitomycin, methotrexate, mitoxantrone, fluorouracil, carboplatin, carmustine (BCNU), methyl CCNU, cisplatin, etoposide, epotetin alfa, interferons (e.g., IFN-α), camptothecin and derivatives thereof, letrozole, panitumumab (Vectibix®), phenesterine, topetecan, vinblastine, vincristine, tamoxifen, thalidomide, tipifarnib (Zarnestra®), piposulfan, nab-5404, nab-5800, nab-5801, Irinotecan, HKP, Ortataxel, gemcitabine, Herceptin®, vinorelbine, Doxil®, capecitabine, Alimta®, Avastin®, Velcade®, Tarceva®, Neulasta®, Lapatinib, Sorafenib, derivatives thereof, chemotherapeutic agents known in the art, and the like. In some embodiments, the chemotherapeutic agent is a composition comprising nanoparticles comprising a thiocolchicine derivative and a carrier protein (such as albumin). In some embodiments, the chemotherapeutic agent is a taxane or a derivative thereof (e.g., paclitaxel, docetaxel, and ortataxel). In some embodiments, the chemotherapeutic is not a taxane.

In some embodiments, the chemotherapeutic agent is a antineoplastic agent including, but is not limited to, carboplatin, Navelbine® (vinorelbine), anthracycline (Doxil®), lapatinib (GW57016), Herceptin®, gemcitabine (Gemzar®), capecitabine (Xeloda®), Alimta®, cisplatin, 5-fluorouracil, epirubicin, cyclophosphamide, Avastin®, Velcade®, etc.

In some embodiments, the chemotherapeutic agent is an antagonist of other factors that are involved in tumor growth, such as EGFR, ErbB2 (also known as Herb), ErbB3, ErbB4, or TNF. Sometimes, it may be beneficial to also administer one or more cytokines to the individual. In some embodiments, the therapeutic agent is a growth inhibitory agent. Suitable dosages for the growth inhibitory agent are those presently used and may be lowered due to the combined action (synergy) of the growth inhibitory agent and the rapamycin or derivative thereof. In some embodiments, the chemotherapeutic agent is a chemotherapeutic agent other than an anti-VEGF antibody, a HER2 antibody, interferon, and an HGFβ antagonist.

Reference to a chemotherapeutic agent herein applies to the chemotherapeutic agent or its derivatives and accordingly the invention contemplates and includes either of these embodiments (agent; agent or derivative(s)). "Derivatives" of a chemotherapeutic agent or other chemical moiety include, but are not limited to, compounds that are structurally similar to the chemotherapeutic agent or moiety, compounds that are in the same general chemical class as the chemotherapeutic agent or moiety, analogs of chemotherapeutic agents, or pharmaceutically acceptable salts of chemotherapeutic agents or their derivatives. In some embodiments, the derivative of the chemotherapeutic agent or moiety retains similar chemical and/or physical property (including, for example, functionality) of the chemotherapeutic agent or moiety.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a tyrosine kinase inhibitor. In some embodiments, the invention provides a method of treating cancer in an individual, comprising administering to the individual a) an effective amount of a composition comprising nanoparticles comprising rapamycin and an albumin, and b) an effective amount of a tyrosine kinase inhibitor. Suitable tyrosine kinase inhibitors include, for example, imatinib (Gleevec®), nilotinim, gefitinib (Iressa®; ZD-1839), erlotinib (Tarceva®; OSI-774), sunitinib malate (Sutent®), sorafenib (Nexavar®), and Lapatinib (GW562016; Tykerb). In some embodiments, the tyrosine kinase inhibitor is a multiple reversible ErbB1 family tyrosine kinase inhibitor (e.g., laptinib). In some embodiments, the tyrosine kinase inhibitor is a single reversible EGFR tyrosine kinase inhibitor (e.g., gefitinib or erlotinib). In some embodiments, the tyrosine kinase inhibitor is erlotinib. In some embodiments, the tyrosine kinase inhibitor is gefitinib. In some embodiments, the tyrosine kinase inhibitor is a single irreversible EGFR tyrosine kinase inhibitor (e.g., EKB-569 or CL-387,785). In some embodiments, the tyrosine kinase inhibitor is a multiple irreversible ErbB family tyrosine kinase inhibitor (e.g. canertinib (CL-1033; PD183805), HKI-272, BIBW 2992, or HKI-357). In some embodiments, the tyrosine kinase inhibitor is a multiple reversible tyrosine kinase inhibitor (e.g., ZD-6474, ZD-6464, AEE 788, or XL647). In some embodiments, the tyrosine kinase inhibitor inhibits ErbB family heterodimerization (e.g., BMS-599626). In some embodiments, the tyrosine kinase inhibitor inhibits protein folding by affecting HSP90 (e.g., benzoquinone ansamycin, IPI-504, or 17-AAG). In some embodiments, there is provided a method to inhibit the proliferation of EGFR expressing tumors in a mammal comprising administering to a mammal infected with such tumors an effective amount of a composition comprising nanoparticles comprising a rapamycin or a derivative thereof and a carrier protein (e.g., albumin) and gefitinib, wherein the gefitinib is administered by pulse-dosing. In some embodiments, the tyrosine kinase inhibitor is an inhibitor of BCR-Abl. In some embodiments, the tyrosine kinase inhibitor is an inhibitor of IGF-1R.

In some embodiments, the method is for treating non-small cell lung carcinoma. In some embodiments, the method is for treating brain cancer (e.g., glioblastoma). In some embodiments, the method is for treating colorectal cancer, gastrointestinal stromal tumor, prostate cancer, ovarian cancer, or thyroid cancer. In some embodiments, the method is for treatment of prostate cancer (e.g., advanced prostate cancer). In some embodiments, the method is for treatment of breast cancer, including treatment of metastatic breast cancer and treatment of breast cancer in a neoadjuvant setting. In some embodiments, the method is for treatment of advanced solid tumor. In some embodiments, the method is for treatment of multiple myeloma. In some embodiments, the method comprises simultaneous and/or sequential administration of at least one EGFR blocker, inhibitor, or antagonist. In some embodiments, the individual has activating mutation(s) in the kinase domain of EGFR. In some embodiments, the individual is of Asian or East Asian ancestry. In some embodiments, the individual is female.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of an antimetabolite agent (such as a nucleoside analog, including for example purine analogs and pyrimidine analogs). In some embodiments, the invention provides a method of treating cancer in an individual, comprising administering to the individual a) an effective amount of a composition comprising nanoparticles comprising rapamycin and an albumin, and b) an effective amount of an antimetabolite agent. An "antimetabolic agent" is an agent which is structurally similar to a metabolite, but cannot be used by the body in a productive manner. Many antimetabolite agents interfere with production of nucleic acids, RNA and DNA. For example, the antimetabolite can be a nucleoside analog, which includes, but is not limited to, azacitidine, azathioprine, capecitabine (Xeloda®), cytarabine, cladribine, cytosine arabinoside (ara-C, cytosar), doxifluridine, fluorouracil (such as 5-fluorouracil), 9-(2-phosphonylmethoxyethyl) adenine, UFT, hydoxyurea, gemcitabine, mercaptopurine, methotrexate, thioguanine (such as 6-thioguanine). Other anti-metabolites include, for example, L-asparaginase (Elspa), decarbazine (DTIC), 2-deoxy-D-glucose, and procarbazine (matulane). In some embodiments, the nucleoside analog is any of (and in some embodiments selected from the group consisting of) gemcitabine, fluorouracil, and capecitabine. In some embodiments, the method is for treatment of metastatic breast cancer or locally advanced breast cancer. In some embodiments, the method is for first line treatment of metastatic breast cancer. In some embodiments, the method is for treatment of breast cancer in a neoadjuvant setting. In some embodiments, the method is for treatment of any of NSCLC, metastatic colorectal cancer, pancreatic cancer, or advanced solid tumor.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of an alkylating agent. In some embodiments, the invention provides a method of treating cancer in an individual, comprising administering to the individual a) an effective amount of a composition comprising nanoparticles comprising rapamycin and an albumin, and b) an effective amount of an alkylating agent. Suitable alkylating agents include, but are not limited to, cyclophosphamide (Cytoxan), mechlorethamine, chlorambucil, melphalan, carmustine (BCNU), thiotepa, busulfan, alkyl sulphonates, ethylene imines, nitrogen mustard analogs, estramustine sodium phosphate, ifosfamide, nitrosoureas, lomustine, and streptozocin. In some embodiments, the alkylating agent is cyclophosphamide. In some embodiments, the cyclophosphamide is administered prior to the administration of the nanoparticle composition. In some embodiments, the method is for treatment of an early stage breast cancer. In some embodiments, the method is for treatment of a breast cancer in an adjuvant or a neoadjuvant setting.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a platinum-based agent. In some embodiments, the invention provides a method of treating cancer in an individual, comprising administering to the individual a) an effective amount of a composition comprising nanoparticles comprising rapamycin and an albumin, and b) an effective amount of a platinum-based agent. Suitable platinum-based agents include, but are not limited to, carboplatin, cisplatin, and oxaliplatin. In some embodiments, the platinum-based agent is carboplatin. In some embodiments, the platinum-based agent is oxaliplatin. We have observed that rapamycin inhibited oxaliplatin induced apoptosis in a dose dependent manner. This inhibition was not overwhelmed by increasing amount of oxaliplatin up to 1:1 (w/w) ratio of the two drugs. The same was observed for Eloxatin® (oxaliplatin injection).

In some embodiments, the method is for treatment of breast cancer (HER2 positive or HER2 negative, including metastatic breast cancer and advanced breast cancer); lung cancer (including advanced NSCLC, first line NSCLC, SCLC, and advanced solid tumor malignancies in the lung); ovarian cancer; head and neck cancer; and melanoma (including metastatic melanoma).

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of an anthracycline antibiotic. In some embodiments, the invention provides a method of treating cancer in an individual, comprising administering to the individual a) an effective amount of a composition comprising nanoparticles comprising rapamycin and an albumin, and b) an effective amount of an anthracycline antibiotic. Suitable anthracycline antibiotic include, but are not limited to, Doxil®, actinomycin, dactinomycin, daunorubicin (daunomycin), doxorubicin (adriamycin), epirubicin, idarubicin, mitoxantrone, and valrubicin. In some embodiments, the anthracycline is any of (and in some embodiments selected from the group consisting of) Doxil®, epirubicin, and doxorubicin. In some embodiments, the method is for treatment of an early stage breast cancer. In some embodiments, the method is for treatment of a breast cancer in an adjuvant or a neoadjuvant setting.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a vinca alkloid. In some embodiments, the invention provides a method of treating cancer in an individual, comprising administering to the individual a) an effective amount of a composition comprising nanoparticles comprising rapamycin and an albumin, and b) an effective amount of a vinca alkloid. Suitable vinca alkaloids include, for example, vinblastine, vincristine, vindesine, vinorelbine (Navelbine®), and VP-16. In some embodiments, the vinca alkaloid is vinorelbine (Navelbine®). In some embodiments, the method is for treatment of stage IV breast cancer and lung cancer.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a topoisomerase inhibitor. In some embodiments, the invention provides a method of treating cancer in an individual, comprising administering to the individual a) an effective amount of a composition comprising nanoparticles comprising rapamycin and an albumin, and b) an effective amount of a topoisomerase inhibitor. In some embodiments, the chemotherapeutic agent is a topoisomerase inhibitor, including, for example, inhibitor of topoisomerase I and topoisomerase II. Exemplary inhibitors of topoisomerase I include, but are not limited to, camptothecin, such as irinotecan and topotecan. Exemplary inhibitors of topoisomerase II include, but are not limited to, amsacrine, etoposide, etoposide phosphate, and teniposide.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of an antiangiogenic agent. In some embodiments, the invention provides a method of treating cancer in an individual, comprising administering to the individual a) an effective amount of a composition comprising nanoparticles comprising rapamycin and an albumin, and b) an effective amount of an antiangiogenic agent. In some embodiments, the method is for treatment of metastatic breast cancer, breast cancer in an adjuvant setting or a neoadjuvant setting, lung cancer (such as first line advanced NSCLC and NSCLC), ovarian cancer, and melanoma (including metastatic melanoma).

Many anti-angiogenic agents have been identified and are known in the art, including those listed by Carmeliet and Jain (2000). The anti-angiogenic agent can be naturally occurring or non-naturally occurring. In some embodiments, the chemotherapeutic agent is a synthetic antiangiogenic peptide. For example, it has been previously reported that the antiangiogenic activity of small synthetic pro-apoptic peptides comprise two functional domains, one targeting the CD13 receptors (aminopeptidase N) on tumor microvessels and the other disrupting the mitochondrial membrane following internalization. Nat. Med. 1999, 5(9):1032-8. A second generation dimeric peptide, CNGRC-GG-d (KLAKLAK)2, named HKP (Hunter Killer Peptide) was found to have improved antitumor activity. Accordingly, in some embodiments, the antiangiogenic peptide is HKP. In some embodiments, the antiangiogenic agent is other than an anti-VEGF antibody (such as Avastin®). In some embodiments, the anti-angiogenic agent is a small molecule inhibitor of VEGFR (such as VEGFR1, VEGFR2, and/or VEGFR3). Suitable small molecule inhibitors of VEGFR include, but are not limited to, vatalanib, AZD2171, pazopanib (GW786034), Sunitinib, AG013736, Sorafenib, ZD6474, XL647, and XL999.

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a proteasome inhibitor, such as bortezomib (Velcade). In some embodiments, the invention provides a method of treating cancer in an individual, comprising administering to the individual a) an effective amount of a composition comprising nanoparticles comprising rapamycin and an albumin, and b) an effective amount of a proteasome inhibitor such as bortezomib (Velcade).

In some embodiments, the invention provides a method of treating cancer in an individual, comprising administering to the individual a) an effective amount of a composition comprising nanoparticles comprising a rapamycin or a derivative thereof and a carrier protein (e.g., albumin), and b) an effective amount of a therapeutic antibody. In some embodiments, the invention provides a method of treating cancer in an individual, comprising administering to the individual a) an effective amount of a composition comprising nanoparticles comprising rapamycin and an albumin, and b) an effective amount of a therapeutic antibody. Suitable therapeutic antibodies include, but are not limited to, anti-VEGF antibody (such as Avastin® (bevacizumab)), anti-HER2 antibody (such as Herceptin® (trastuzumab)), Erbitux® (cetuximab), Campath (alemtuzumab), Myelotarg (gemtuzumab), Zevalin (ibritumomab tiuextan, Rituxan (rituximab), and Bexxar (tositumomab)). In some embodiments, the chemotherapeutic agent is Erbitux® (cetuximab). In some embodiments, the chemotherapeutic agent is a therapeutic antibody other than an antibody against VEGF or HER2. In some embodiments, the method is for treatment of HER2 positive breast cancer, including treatment of advanced breast cancer, treatment of metastatic cancer, treatment of breast cancer in an adjuvant setting, and treatment of cancer in a neoadjuvant setting. In some embodiments, the method is for treatment of any of metastatic breast cancer, breast cancer in an adjuvant setting or a neoadjuvant setting, lung cancer (such as first line advanced NSCLC and NSCLC), ovarian cancer, head and neck cancer, and melanoma (including metastatic melanoma). For example, in some embodiments, there is provided a method for treatment of HER2 positive metastatic breast cancer in an individual, comprising administering to the individual about 54 mg to 540 mg rapamycin or about 30 mg/m2 to 300 mg/m2 rapamycin in a nanoparticle composition weekly for three weeks with the fourth week off, concurrent with the administration of Herceptin®.

In some embodiments, there is provided a method of treating cancer in an individual, comprising administering to the individual: a) an effective amount of a composition comprising nanoparticles comprising rapamycin or a derivative thereof and a carrier protein (e.g., albumin), and b) an effective amount of an anti-VEGF antibody. In some embodiments, the effective amounts of the rapamycin or a derivative thereof nanoparticle composition and the anti-VEGF antibody synergistically inhibit cell proliferation (such as tumor cell growth). In some embodiments, at least about 10% (including for example at least about any of about 20%, 30%, 40%, 60%, 70%, 80%, 90%, or 100%) cell proliferation is inhibited. In some embodiments, the rapamycin or a derivative thereof is rapamycin. In some embodiments, the anti-VEGF antibody is bevacizumab (such as Avastin®). In some embodiments, the rapamycin or a derivative thereof in the nanoparticle in the composition is administered by intravenous administration. In some embodiments, the anti-VEGF antibody is administered by intravenous administration. In some embodiments, both the rapamycin or a derivative thereof in the nanoparticle composition and the anti-VEGF antibody are administered by intravenous administration.

In some embodiments, there is provided a method of inhibiting tumor metastasis in an individual, comprising administering to the individual: a) an effective amount of a composition comprising nanoparticles comprising rapamycin or a derivative thereof and a carrier protein (e.g., albumin), and b) an effective amount of an anti-VEGF antibody. In some embodiments, the effective amounts of the rapamycin or a derivative thereof nanoparticle composition and the anti-VEGF antibody synergistically inhibit tumor metastasis. In some embodiments, at least about 10% (including for example at least about any of about 20%, 30%, 40%, 60%, 70%, 80%, 90%, or 100%) metastasis is inhibited. In some embodiments, method of inhibiting metastasis to lymph node is provided. In some embodiments, method of inhibiting metastasis to the lung is provided. In some embodiments, the rapamycin or a derivative thereof is rapamycin. In some embodiments, the anti-VEGF antibody is bevacizumab (such as Avastin®). In some embodiments, the rapamycin or a derivative thereof in the nanoparticle in the composition is administered by intravenous administration. In some embodiments, the anti-VEGF antibody is administered by intravenous administration. In some embodiments, both the rapamycin or a derivative thereof in the nanoparticle composition and the anti-VEGF antibody are administered by intravenous administration.

In some embodiments, two or more chemotherapeutic agents are administered in addition to the rapamycin or a derivative thereof in the nanoparticle composition. These two or more chemotherapeutic agents may (but not necessarily) belong to different classes of chemotherapeutic agents. Examples of these combinations are provided herein. Other combinations are also contemplated.

In some embodiments, there is provided a method of treating cancer in an individual, comprising administering to the individual a) an effective amount of a composition comprising nanoparticles comprising a rapamycin or a derivative thereof and a carrier protein (e.g., albumin), b) an effective amount of an antimetabolite (such as a nucleoside analog, for example, gemcitabine), and c) an anthracycline antibiotic (such as epirubicin). In some embodiments, there is provided a method of treating cancer in an individual, comprising administering to the individual a) an effective amount of a composition comprising nanoparticles comprising rapamycin and an albumin, b) an effective amount of an antimetabolite (such as a nucleoside analog, for example, gemcitabine), and c) an effective amount of an anthracycline antibiotic (such as epirubicin). In some embodiments, the method is for treatment of breast cancer in a neoadjuvant setting. For example, in some embodiments, there is provided a method of treating locally advanced/inflammatory cancer in an individual comprising administering to the individual rapamycin (such as about 30 mg/m2 to about 300 mg/m2 or such as about 50 mg to 540 mg rapamycin) in a nanoparticle composition every two weeks; 2000 mg/m2 gemcitabine, every two weeks; and 50 mg/m2 epirubicin, every two weeks. In some embodiments, there is provided a method of treating breast cancer in an individual in an adjuvant setting, comprising administering to the individual rapamycin (such as about 30 mg/m2 to about 300 mg/m2 or such as about 50 mg to 540 mg rapamycin) in a nanoparticle composition every two weeks, 2000 mg/m2 gemcitabine, every two weeks, and 50 mg/m2 epirubicin, every two weeks.

In some embodiments, there is provided a method of treating cancer in an individual, comprising administering to the individual a) an effective amount of a composition comprising nanoparticles comprising a rapamycin or a derivative thereof and a carrier protein (e.g., albumin), b) an effective amount of a platinum-based agent (such as carboplatin), and c) a therapeutic antibody (such as ant-HER2 antibody (such as Herceptin®) and anti-VEGF antibody (such as Avastin®)). In some embodiments, there is provided a method of treating cancer in an individual, comprising administering to the individual a) an effective amount of a composition comprising nanoparticles comprising rapamycin and an albumin, b) an effective amount of a platinum-based agent (such as carboplatin), and c) a therapeutic antibody (such as ant-HER2 antibody (such as Herceptin®) and anti-VEGF antibody (such as Avastin®)). In some embodiments, the method is for treatment of any of advanced breast cancer, metastatic breast cancer, breast cancer in an adjuvant setting, and lung cancer (including NSCLC and advanced NSCLC). In some embodiments, there is provided a method of treating metastatic cancer in an individual, comprising administering to the individual rapamycin (such as about 30 mg/m2 to about 300 mg/m2 or such as about 50 mg to 540 mg rapamycin) in a nanoparticle composition and carboplatin, AUC=2, wherein the administration is carried out weekly for three weeks with the fourth week off. In some embodiments, the method further comprises weekly administering about 2-4 mg/kg of Herception®.

In some embodiments, there is provided a method of treating cancer in an individual, comprising administering to the individual a) an effective amount of a composition comprising nanoparticles comprising a rapamycin or a derivative thereof and a carrier protein (e.g., albumin), b) an effective amount of a platinum-based agent (such as carboplatin), and c) a vinca alkaloid (such as Navelbine®). In some embodiments, there is provided a method of treating cancer in an individual, comprising administering to the individual a) an effective amount of a composition comprising nanoparticles comprising rapamycin and an albumin, b) an effective amount of a platinum-based agent (such as carboplatin), and c) a vinca alkaloid (such as Navelbine®). In some embodiments, the method is for treatment of lung cancer.

In some embodiments, the invention provides a method of treating cancer in an individual, comprising administering to the individual a) an effective amount of a composition comprising nanoparticles comprising a rapamycin or a derivative thereof and a carrier protein (e.g., albumin), b) an effective amount of an alkylating agent (such as cyclophosphamide) and c) an anthracycline antibiotic (such as adriamycin). In some embodiments, the invention provides a method of treating cancer in an individual, comprising administering to the individual a) an effective amount of a composition comprising nanoparticles comprising rapamycin and an albumin, b) an effective amount of an alkylating agent (such as cyclophosphamide) and c) an anthracycline antibiotic (such as adriamycin). In some embodiments, the method is for treatment of an early stage breast cancer. In some embodiments, the method is for treatment of a breast cancer in an adjuvant or a neoadjuvant setting. For example, in some embodiments, there is provided a method of treating an early stage breast cancer in an individual, comprising administering rapamycin (such as about 30 mg/m2 to about 300 mg/m2 or 50 mg to 540 mg rapamycin) in a nanoparticle composition, 60 mg/m2 adriamycin, and 600 mg/m2 cyclophosphamide, wherein the administration is carried out once every two weeks.

In some embodiments, the invention provides a method of treating cancer in an individual, comprising administering to the individual a) an effective amount of a composition comprising nanoparticles comprising a rapamycin or a derivative thereof and a carrier protein (e.g., albumin) and b) an effective amount of an p110α-specific inhibitor (e.g., PX-866). In some embodiments, the method further comprises administering an effective amount of a tyrosine kinase inhibitor (e.g., gefitinib or erlotinib). In some embodiments, the cancer is non-small cell lung carcinoma.

In some embodiments, the invention provides a method of treating cancer in an individual, comprising administering to the individual a) an effective amount of a composition comprising nanoparticles comprising a rapamycin or a derivative thereof and a carrier protein (e.g., albumin) and b) an effective amount of a compound that affects the MAPK pathway (e.g., sorafenib (BAY49-9006). In some embodiments, the method further comprises administering an effective amount of a tyrosine kinase inhibitor (e.g., gefitinib or erlotinib). In some embodiments, the cancer is non-small cell lung carcinoma. In some embodiments, the cancer is brain cancer (e.g., glioblastoma).

In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that affects a signaling pathway involving a target of rapamycin. In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that affects a signaling pathway involving mTOR. In some embodiments, the other agent affects a signaling pathway involving TORC1. In some embodiments, the other agent affects a signaling pathway involving mTORC2. Signaling pathways involving mTOR include, but are not limited to, PI3K/Akt pathwayn and cAMP/AMPK pathway. These pathways are interrelated. Accordingly, an agent that affects one signaling pathway frequently affects the other pathway (either directly or indirectly).

In some embodiments, the signaling pathway involving mTOR is the PI3K/Akt signaling pathway. For example, in some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that inhibits PI3K/Akt activation. In some embodiments, the cancer is any of HER2+ breast cancer, chronic mylogenous leukemia CML, ovarian cancer, endometrial cancer, sarcoma, SCCHN (squamous cell carcinomaterm of the head and neck), and thyroid cancer.

The PI3/Akt signaling pathway described herein includes any members or components that directly or indirectly participate in the signal transduction cascade. These include, but are not limited to, PI3 kinase, Akt, PDK1, RAPTOR (regulatory associated protein if mTOR), TSC1 (tuberous sclerosis complex 1), TSC2, PTEN (phosphatase and tenesin homolog), and downstream effectors such as cyclin D, HIF1, HIF2, Glut1, LAT1, and c-Myc. Components of the PI3/Akt signaling pathway may also include RHEB, Rictor, S6K, 4EBP1, cAMP, cAMPK, GβL, IRS, PIP2, PIP3, Rho, Ras, Abl, PKC, eIF4E, PDGFR, VEGFR, and VHL. The agent that affects (such as inhibits) the PI3K/Akt signaling pathway can thus act through modulation of any one or more of these components.

In some embodiments, the other agent inhibits PI3 kinase (PI3K). Suitable inhibitors of PI3K include, but are not limited to, wortmannin and the derivatives or analogs thereof; celecoxib and analogs thereof, such as OSU-03012 and OSU-03013; 3-deoxy-D-myo-inositol analogs, such as PX-316; 2'-substituted 3'-deoxy-phosphatidyl-myo-inositol analogs; fused heteroaryl derivatives; 3-(imidazo[1,2-a]pyridin-3-yl) derivatives; Ly294002; quinazoline-4-one derivatives, such as IC486068; 3-(hetero)aryloxy substituted benzo(b) thiophene derivatives; viridins, including semi-synthetic viridins such as such as PX-866 (acetic acid (1S, 4E, 10R, 11 R, 13S, 14R)-[4-dially laminomethylene-6-hydroxy-1-methoxymethyl-10,13-dimethyl-3,7,17-trioxo-1,3,4,7,10,11,12, 13,14,15,16,17-dodecahydro-2-oxa-cyclopenta[a]phenanthren-11-yl ester); and wortmannin and derivatives thereof.

In some embodiments, the other agent inhibits Akt kinase, including Akt1, Akt2, and Akt3. In some embodiments, the other agent inhibits phosphorylation of 5473 of the human Akt kinase, but not T308. In some embodiments, the second compound inhibits phosphorylation of T308 of the human Akt kinase, but not S473. In some embodiments, the other agent inhibits phorphorylation of both S473 and T308 of the Akt kinase. In some embodiments, the other agent interferes with the membrane localization of the Akt kinase. Suitable inhibitors of Akt kinase include, but are not limited to, Akt-1-1 (inhibits Akt 1), Akt-1-1,2 (inhibits Akt1 and 2), API-59CJ-Ome, 1-H-imidazo[4,5-c]pyridinyl compounds, indole-3-carbinol and derivatives thereof, perifosine, phosphatidylinositol ether lipid analogues, triciribine (TCN or API-2 or NCI identifier: NSC 154020). In some embodiments, the other agent is perifosine.

In some embodiments, the other agent is an inhibitor of PDK1.

In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that inhibits cyclin D1 (such as cycline D1 overexpression). In some embodiments, the cancer is any of mantle cell lymphoma and breast cancer.

In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that inhibits Myc over expression. In some embodiments, the cancer is burkitt lymphoma.

In some embodiments, the other agent inhibits HIF. In some embodiments, the HIF is HIF 1. In some embodiments, the HIF is HIF2. In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of another agent that inhibits HIF (such as HIF overexpression). In some embodiments, the other agent inhibits HIF-mediated angiogenesis. In some embodiments, the cancer is RCC and Von Hippel-Lindau (VHL).

Other PI3K/Akt signaling pathway inhibitors include, but are not limited to, e.g., FTY720 and UCN-01.

While the agents described herein are sometimes referred to as signaling pathway inhibitors, the methods described herein includes the use of these inhibitors to treat cancer regardless of the mechanism of action or how the therapeutic effect is achieved. Indeed, it is recognized that such compounds may have more than one target, and the initial activity recognized for a compound may not be the activity that it possesses in vivo when administered to a subject, or whereby it achieves its therapeutic efficacy. Thus, the description of a compound as a pathway or protein target (e.g., Akt or mTOR) inhibitor indicates that a compound possesses such activity, but in no way restricts a compound to having that activity when used as a therapeutic or prophylactic agent.

Other agents that can be used in combination with rapamycin (or its derivative) compositions described herein include, for example, flavopiridol, antifolates, SN38, inhibitor of breast cancer resistant protein (such as KO143 and fumitremorgin C).

In some embodiments, there is provided a method of treating advanced breast cancer in an individual, comprising administering to the individual a) an effective amount of a composition comprising nanoparticles comprising a rapamycin and an albumin, b) an effective amount of carboplatin. In some embodiments, the method further comprises administering an effective amount of Herceptin® to the individual. In some embodiments, there is provided a method of treating metastatic breast cancer in an individual, comprising administering to the individual a) an effective amount of a composition comprising nanoparticles comprising rapamycin and an albumin, b) an effective amount of gemcitabine. In some embodiments, there is provided a method of treating advanced non-small cell lung cancer in an individual, comprising administering to the individual a) an effective amount of a composition comprising nanoparticles comprising rapamycin and an albumin, b) an effective amount of carboplatin.

In some embodiments, the method further comprises identifying a cancer patient population (e.g., breast cancer) based on a hormone receptor status of patients having tumor tissue not expressing both ER and PgR and administering to the patient population an effective amount of a composition comprising nanoparticles comprising rapamycin or a derivative thereof and a carrier protein (e.g., albumin). In some embodiments, the method further comprises administering to the patient population an effective amount of at least one other chemotherapeutic agent. The at least one other chemotherapeutic agent may be administered concurrently or sequentially with rapamycin or a derivative thereof nanoparticles. In some embodiments, the at least one other chemotherapeutic agent comprises 5-Fluoruracil, Epirubicin and Cyclophosphamide (FEC) administered concurrently or sequentially. These methods may have higher efficacy in ER(−)/PgR(−) populations in all patient populations, both HER-2 positive and HER-2 negative.

In some embodiments of any of the above methods of combination therapy with a chemotherapeutic agent, there is provided a composition comprising nanoparticles comprising rapamycin or a derivative thereof and a carrier protein (such as albumin) and at least one other chemotherapeutic agent. The compositions described herein may comprise effective amounts of the rapamycin or a derivative thereof and the chemotherapeutic agent for the treatment of a cancer. In some embodiments, the chemotherapeutic agent and rapamycin or a derivative thereof are present in the composition at a predetermined ratio, such as the weight ratios described herein. In some embodiments, the invention provides a synergistic composition of an effective amount of a composition comprising nanoparticles comprising rapamycin or a derivative thereof and an effective amount of at least one other chemotherapeutic agent.

In some embodiments of any of the above methods of combination therapy with a chemotherapeutic agent, the invention provides pharmaceutical compositions comprising nanoparticles comprising a rapamycin or a derivative thereof and a carrier protein (such as albumin) for use in the treatment of a cancer, wherein said use comprises simultaneous and/or sequential administration of at least one other chemotherapeutic agent. In some embodiments, the invention provides a pharmaceutical composition comprising a chemotherapeutic agent for use in the treatment of a cancer, wherein said use comprises simultaneous and/or sequential administration of a composition comprising nanoparticles comprising rapamycin or a derivative thereof and a carrier protein (such as albumin). In some embodiments, the invention provides rapamycin or a derivative thereof-containing nanoparticle compositions and compositions comprising one other chemotherapeutic agent for simultaneous, and/or sequential use for treatment of a cancer.

In some embodiments, the invention provides a method to treat cancer comprising administering to an individual an effective amount of a composition comprising nanoparticles comprising a rapamycin or a derivative thereof and a carrier protein (such as albumin) simultaneously and/or sequentially with surgery, radiation, gene therapy, immunotherapy, bone marrow transplantation, stem cell transplantation, hormone therapy, targeted therapy, cryotherapy, ultrasound therapy, and/or photodynamic therapy. In some embodiments, the present invention provides a method of treating cancer comprising a first therapy comprising administering nanoparticles comprising rapamycin and an albumin, and a second therapy comprising surgery, radiation, gene therapy, immunotherapy, bone marrow transplantation, stem cell transplantation, hormone therapy, targeted therapy, cryotherapy, ultrasound therapy, and/or photodynamic therapy. In some embodiments, the cancer may be prostate cancer. In some embodiments, the second therapy is hormone therapy. In some embodiments, the second therapy is radiation therapy. In some embodiments, the second therapy is surgery.

The administration of rapamycin or a derivative thereof nanoparticle composition may be prior to the hormone therapy, radiation, and/or surgery, after the hormone therapy, radiation, and/or surgery, or concurrent with hormone therapy, radiation, and/or surgery. For example, the administration of rapamycin or a derivative thereof nanoparticle composition may precede or follow hormone therapy, radiation, and/or surgery therapy by intervals ranging from minutes to weeks. In some embodiments, the time period between the first and the second therapy is such that the rapamycin or a derivative thereof and a carrier protein (e.g., albumin) and hormone therapy, radiation, and/or surgery would still be able to exert an advantageously combined effect on the cell. In some embodiments, it may be desirable to extend the time period for treatment significantly, where several days to several weeks lapse between the two therapies.

Surgery described herein includes resection in which all or part of cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of superficial surgery, precancers, or normal tissues are also contemplated.

The hormone therapy, radiation therapy, and/or surgery may be carried out in addition to the administration of chemotherapeutic agents. For example, the individual may first be administered with a rapamycin or its derivative thereof-containing nanoparticle composition and at least one other chemotherapeutic agent, and subsequently be subject to hormone therapy, radiation therapy, and/or surgery. Alternatively, the individual may first be treated with hormone therapy, radiation therapy, and/or surgery, which is then followed by the administration of a nanoparticle composition and at least one other chemotherapeutic agent. Other combinations are also contemplated.

Administration of nanoparticle compositions disclosed above in conjunction with administration of chemotherapeutic agent is equally applicable to those in conjunction with hormone therapy, radiation therapy, and/or surgery.

The term hormone therapy, as used herein, includes, but is not limited to, androgen ablation therapy, androgen deprivation therapy, hormonal ablation therapy, combined hormone blockade, intermittent hormonal therapy, neoadjuvant hormonal therapy, neoadjuvant androgen suppression, and neoadjuvant androgen deprivation. Androgens, such as testosterone, regulate the growth, differentiation, and rate of apoptosis in the prostate and its malignancies. In some embodiments, prostate cancer may be treated by exploiting the general dependency of prostate cancer on androgen through several therapies referred to as hormone therapy.

In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of a gonadotropin-releasing hormone (GnRH) agonist (also called LHRH agonist, luteinizing-hormone releasing hormone agonist). In some embodiments, there is provided a method of treating cancer in an individual, comprising administering to the individual a) an effective amount of a composition comprising nanoparticles comprising rapamycin and an albumin and b) an effective amount of a GnRH agonist. In some embodiments, the method is for treatment of prostate cancer. In some embodiments, the invention provides pharmaceutical compositions comprising nanoparticles comprising a rapamycin or a derivative thereof and a carrier protein (such as albumin) for use in the treatment of a cancer, wherein said use comprises simultaneous and/or sequential administration of at least one GnRH agonist. Suitable therapeutic GnRH agonists include, but are not limited to, leuprolide, goserelin, naferelin, meterelin, buserelin, historelin, deslorelin, and triptorelin.

In some embodiments, there is provided a method of treating cancer in an individual, comprising administering to the individual a) an effective amount of a composition comprising nanoparticles comprising a rapamycin or a derivative thereof and a carrier protein (e.g., albumin), b) an effective amount of a GnRH agonist, and c) antiandrogen. In some embodiments, there is provided a method of treating cancer in an individual, comprising administering to the individual a) an effective amount of a composition comprising nanoparticles comprising rapamycin and an albumin, b) an effective amount of a GnRH agonist, c) and an antiandrogen. In some embodiments, the method is for treatment of prostate cancer. In some embodiments, the antiandrogen administration begins prior to treatment with the GnRH agonist and/or the rapamycin-containing nanoparticle composition. In some embodiments, the invention provides pharmaceutical compositions comprising nanoparticles comprising a rapamycin or a derivative thereof and a carrier protein (such as albumin) for use in the treatment of a cancer, wherein said use comprises simultaneous and/or sequential administration of at least one GnRH agonist or antiandrogen. In some embodiments, the antiandrogen is administered before the GnRH agonist and/or the rapamycin-containing nanoparticle composition, and the administration of the antiandrogen is continued for at least the first month of GnRH agonist therapy. In some embodiments, the antiandrogen administration begins any of about 1, 2, 3, 4, 5, 6, 7, 8, 9, 10, 11, 12, 13, 14, 15, 16, 17, 18, 19, 20, 21, 22, 23, and 24 weeks prior to treatment with the GnRH agonist and/or the rapamycin-containing nanoparticle composition Suitable therapeutic GnRH agonists include, but are not limited to, leuprolide, goserelin, naferelin, meterelin, buserelin, historelin, deslorelin, and triptorelin. Suitable therapeutic antiandrogens include, but are not limited to, bicalutamide (Casodex), flutamide (Eulexin), cyproterone, nilutamide (Nilandron), and other therapeutic agents that are effective in ultimately reducing circulating androgen levels to the castrate level In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of a gonadotropin-releasing hormone (GnRH) antagonist (also called LHRH antagonist, luteinizing-hormone releasing hormone antagonist). In some embodiments, there is provided a method of treating cancer in an individual, comprising administering to the individual a) an effective amount of a composition comprising nanoparticles comprising rapamycin and an albumin and b) an effective amount of a GnRH antagonist. In some embodiments, the method is for treatment of prostate cancer. In some embodiments, the invention provides pharmaceutical compositions comprising nanoparticles comprising a rapamycin or a derivative thereof and a carrier protein (such as albumin) for use in the treatment of a cancer, wherein said use comprises simultaneous and/or sequential administration of at least one GnRH antagonist. Suitable therapeutic GnRH antagonist include, but are not limited to, Cetrorelix acetate (Cetrotide), by Serono, Ganirelix acetate (Antagon), by Organon International, Abarelix (Plenaxis), and the like.

In an embodiment, the method comprises the administration of a therapeutic effective amount of a rapamycin-containing nanoparticle composition at any one or more of the following times: prior to hormone therapy, in conjunction with hormone therapy, during hormone therapy, or following hormone therapy to treat prostate cancer. In some embodiments, the method comprises the administration of a therapeutic effective amount of a rapamycin-containing nanoparticle composition either simultaneously with or separately from the hormone therapeutic agent to treat prostate cancer. A combination of a therapeutically effective amount of one or more standard hormone therapy drugs and a therapeutically effective amount of rapamycin or a derivative in a nanoparticle composition may result in a synergistic effect in prostate tumor inhibition (including regression of existing prostate tumor).

In some embodiments, there is provided a method of treating cancer in an individual, comprising administering to the individual a) an effective amount of a composition comprising nanoparticles comprising a rapamycin or a derivative thereof and a carrier protein (e.g., albumin) and b) an effective amount of an endothelin-A receptor blocker, inhibitor, or antagonist. In some embodiments, there is provided a method of treating cancer in an individual, comprising administering to the individual a) an effective amount of a composition comprising nanoparticles comprising rapamycin and an albumin and b) an effective amount of an endothelin-A receptor blocker, inhibitor, or antagonist. In some embodiments, the method is for treatment of prostate cancer (such as advanced prostate cancer). In some embodiments, the invention provides pharmaceutical compositions comprising nanoparticles comprising a rapamycin or a derivative thereof and a carrier protein (such as albumin) for use in the treatment of a cancer, wherein said use comprises simultaneous and/or sequential administration of at least one endothelin-A receptor blocker, inhibitor, or antagonist. A suitable therapeutic endothelin-A receptor blocker, inhibitor, or antagonist includes, but is not limited to, Atrasentan (ABT 627, Abbott Laboratories, Abbott Park, Ill.).

It is understood that any of the methods of treating cancer described herein (such as above section "Methods of Treating Cancer") apply to and include description of combination therapies. In some embodiments of any of the methods of treatment related to combination therapy described herein, treatment with the combination of the first therapy (e.g., a nanoparticle composition comprising rapamycin or a derivative thereof and a carrier protein) and the second therapy (e.g., one or more compounds useful for treating cancer) may result in an additive or even synergistic (e.g., greater than additive) result compared to administration of either therapy alone. In some embodiments, a lower amount of each pharmaceutically active compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. Preferably, the use of a small amount of pharmaceutically active compound results in a reduction in the number, severity, frequency, or duration of one or more side-effects associated with the compound.

In some embodiments of any of the methods of treatment related to combination therapy, the rapamycin or derivative thereof and the second compound (e.g., a chemotherapeutic agent and/or hormone therapeutic agent) are present in a single composition containing at least two different nanoparticles, wherein some of the nanoparticles in the composition comprise the rapamycin or derivative thereof and a carrier protein, and some of the other nanoparticles in the composition comprise a second pharmaceutically active compound and a carrier protein. In some embodiments, only the rapamycin or derivative thereof is contained in nanoparticles. In some embodiments, simultaneous administration of rapamycin or derivative thereof in the nanoparticle composition and the second compound can be combined with supplemental doses of rapamycin and/or the second compound.

In some embodiments of any of the above embodiments related to combination therapies described herein, the first and second therapies are administered simultaneously, either in the same composition or in separate compositions. In some embodiments, the first and second therapies are administered sequentially, i.e., the first therapy is administered either prior to or after the administration of the first and second therapy. In some embodiments, the administration of the first and second therapies is concurrent, i.e., the administration period of the first therapy and that of the second therapy overlap with each other. In some embodiments, the administration of the first and second therapies is non-concurrent. For example, in some embodiments, the administration of the first therapy is terminated before the second therapy is administered. In some embodiments, the administration of the second therapy is terminated before the first therapy is administered. In some embodiments, the second therapy is radiation therapy. In some embodiments, the second therapy is surgery.

In some embodiments of any of the above embodiments related to combination therapy, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer.

In some embodiments of any of the above embodiments related to combination therapy, a taxane is not administered to the individual. In some embodiments, the taxane administered is not a nanoparticle composition. In some embodiments, the nanoparticle composition comprising rapamycin or a derivative thereof is not administered in conjunction with a taxane. In some embodiments, a taxane is not administered to the individual during the time period in which the individual is receiving one or more doses of a nanoparticle composition comprising rapamycin or a derivative thereof In some embodiments, the individual was treated with a taxane before treatment begins with a nanoparticle composition comprising rapamycin or a derivative thereof For example, the individual may have received a taxane one or more days, weeks, months, or years before treatment begins with a nanoparticle composition comprising rapamycin or a derivative thereof In other embodiments, the individual never receives a taxane before treatment begins with a nanoparticle composition comprising rapamycin or a derivative thereof In some embodiments, the individual is treated with a taxane after treatment with a nanoparticle composition comprising rapamycin or derivative thereof terminates. In other embodiments, the individual is never treated with a taxane after treatment with a nanoparticle composition comprising rapamycin or derivative thereof terminates. In some embodiments, the composition, first therapy, and/or second therapy do not contain a taxane. In other embodiments, the composition, first therapy, and/or second therapy comprise a taxane.

Dosing and Method of Administration

The dose of the inventive composition administered to an individual (such as a human) may vary with the particular composition, the method of administration, and the particular stage of cancer being treated. The amount should be sufficient to produce a desirable response, such as a therapeutic or prophylactic response against cancer. In some embodiments, the amount of the composition is a therapeutically effective amount. In some embodiments, that amount of the composition is a prophylactically effective amount. In some embodiments, the amount of rapamycin or a derivative thereof in the composition is below the level that induces a toxicological effect (i.e., an effect above a clinically acceptable level of toxicity) or is at a level where a potential side effect can be controlled or tolerated when the composition is administered to the individual.

In some embodiments, the amount of rapamycin or a derivative thereof in the composition is an amount sufficient to increase basal AKT activity, increase AKT phosphorylation, increase PI3-kinase activity, increase the length of activation of AKT (e.g., activation induced by exogenous IGF-1), inhibit serine phosphorylation of IRS-1, inhibit IRS-1 degradation, inhibit or alter CXCR4 subcellular localization, inhibit VEGF secretion, decrease expression of cyclin D2, decrease expression of survivin, inhibit IL-6-induced multiple myeloma cell growth, inhibit cancer cell proliferation, increase apoptosis, increase cell cycle arrest, increase cleavage of poly(ADPribose) polymerase, increase cleavage of caspase-8/caspase-9, alter or inhibit signaling in the phosphatidylinositol 3-kinase/AKT/mTOR and/or cyclin D1/retinoblastoma pathways, inhibit angiogenesis, and/or inhibit osteoclast formation.

In some embodiments, the invention provides a method of treating cancer in an individual by administering to the individual (e.g., a human) an effective amount of a composition comprising nanoparticles that comprise rapamycin or a derivative thereof and a carrier protein (e.g., albumin such as human serum albumin). In some embodiments, the amount of rapamycin or a derivative thereof in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of rapamycin or derivative thereof in the effective amount of the composition (e.g., a unit dosage form) is in the range of about 54 mg to about 540 mg, such as about 180 mg to about 270 mg or about 216 mg. In some embodiments, the concentration of the rapamycin in the composition is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg /ml. In some embodiments, the concentration of the rapamycin is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of rapamycin or a derivative thereof in the nanoparticle composition include, but are not limited to, about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$ rapamycin. In various embodiments, the composition includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ rapamycin or a derivative thereof. In some embodiments, the amount of the rapamycin or a derivative thereof per administration is less than about any of 25 mg/m$^2$, 22 mg/m$^2$, 20 mg/m$^2$, 18 m g/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of rapamycin or a derivative thereof in the composition is included in any of the following ranges: about 1 to about 5 mg/m$^2$, about 5 to about 10 mg/m², about 10 to about 25 mg/m², about 25 to about 50 mg/m², about 50 to about 75 mg/m², about 75 to about 100 mg/m², about 100 to about 125 mg/m², about 125 to about 150 mg/m², about 150 to about 175 mg/m², about 175 to about 200 m g/m², about 200 to about 225 mg/m², about 225 to about 250 mg/m², about 250 to about 300 mg/m², about 300 to about 350 mg/m², or about 350 to about 400 mg/m². Preferably, the effective amount of rapamycin or a derivative thereof in the composition is about 30 to about 300 mg/m², such as about 100 to about 150 mg/m², about 120 mg/m², about 130 mg/m², or about 140 mg/m².

In some embodiments of any of the above aspects, the effective amount of rapamycin or a derivative thereof in the composition includes at least about any of 1 mg/kg, 2.5 mg/kg, 5 mg/kg, 7.5 mg/kg, 10 mg/kg, 15 mg/kg, or 20 mg/kg. In various embodiments, the effective amount of rapamycin or a derivative thereof in the composition includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 5 mg/kg, or 1 mg/kg rapamycin or a derivative thereof.

Exemplary dosing frequencies include, but are not limited to, weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the composition can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. In some embodiments, the rapamycin or derivative thereof is administered over a period of at least one month, wherein the interval between each administration is no more than about a week, and wherein the dose of the rapamycin or a derivative thereof at each administration is about 0.25 mg/m² to about 75 mg/m², such as about 0.25 mg/m² to about 25 m g/m² or about 25 mg/m² to about 50 mg/m².

In some embodiments, the dosage of rapamycin in a nanoparticle composition can be in the range of 100-400 mg/m² when given on a 3 week schedule, or 50-250 mg/m² when given on a weekly schedule. Preferably, the amount of rapamycin is about 80 to about 180 mg/m² (e.g., about 100 mg/m² to about 150 mg/m², such as about 120 mg/m²).

Other exemplary dosing schedules for the administration of the nanoparticle composition (e.g., rapamycin/albumin nanoparticle composition) include, but are not limited to, 100 mg/m², weekly, without break; 75 mg/m² weekly, 3 out of four weeks; 100 mg/m², weekly, 3 out of 4 weeks; 125 mg/m², weekly, 3 out of 4 weeks; 125 mg/m², weekly, 2 out of 3 weeks; 130 mg/m², weekly, without break; 175 mg/m², once every 2 weeks; 260 mg/m², once every 2 weeks; 260 mg/m², once every 3 weeks; 180-300 mg/m², every three weeks; 60-175 mg/m², weekly, without break; 20-150 mg/m² twice a week; and 150-250 mg/m² twice a week. The dosing frequency of the composition may be adjusted over the course of the treatment based on the judgment of the administering physician.

In some embodiments, the composition is administered about 20 to about 40 mg/kg three times weekly. In some embodiments, the composition is administered about 60 to about 120 mg/m², three times weekly or about 90 mg/m² daily. In some embodiments, the composition is administered about 30 mg/kg daily. In some embodiments, methods of treating multiple myeloma following these dosing regimes are provided.

In yet another aspect, the invention provides a method of treating cancer in an individual by parenterally administering to the individual (e.g., a human) an effective amount of a composition comprising nanoparticles that comprise rapamycin or a derivative thereof and a carrier protein (e.g., albumin such as human serum albumin). In some embodiments, the route of administration is intravenous, intra-arterial, intramuscular, or subcutaneous. In various embodiments, about 54 mg to about 540 mg, such as about 180 mg to about 270 mg or about 216 mg, of the rapamycin or derivative thereof is administered per dose. In some embodiments, a taxane is not contained in the composition. In some embodiments, the rapamycin or derivative thereof is the only pharmaceutically active agent for the treatment of cancer that is contained in the composition.

The compositions described herein can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. For example, the inventive composition can be administered by inhalation to treat conditions of the respiratory tract. The composition can be used to treat respiratory conditions such as pulmonary fibrosis, broncheolitis obliterans, lung cancer, bronchoalveolar carcinoma, and the like. In one embodiment of the invention, nanoparticles (such as albumin nanoparticles) of the inventive compounds can be administered by any acceptable route including, but not limited to, orally, intramuscularly, transdermally, intravenously, through an inhaler or other air borne delivery systems and the like. In some embodiments, the rapamycin or derivative thereof is not coating a stent or is not administered using a stent.

The dosing frequency of the rapamycin-containing nanoparticle composition and the second compound may be adjusted over the course of the treatment based on the judgment of the administering physician. In some embodiments, the first and second therapies are administered simultaneously, sequentially, or concurrently. When administered separately, the rapamycin-containing nanoparticle composition and the second compound can be administered at different dosing frequency or intervals. For example, the rapamycin-containing nanoparticle composition can be administered weekly, while a second compound can be administered more or less frequently. In some embodiments, sustained continuous release formulation of the rapamycin-containing nanoparticle and/or second compound may be used. Various formulations and devices for achieving sustained release are known in the art. A combination of the administration configurations described herein can be used.

Modes of Administration of Combination Therapies

In some embodiments, the present invention provides a method of treating cancer comprising a first therapy comprising administering nanoparticles comprising rapamycin or a derivative thereof and a carrier protein (e.g., albumin) and a second therapy comprising chemotherapy and/or hormone therapy. In some embodiments, the method comprises a) a first therapy comprising administering to the individual a composition comprising nanoparticles of rapamycin and an albumin; and b) a second therapy comprising chemotherapy and/or hormone therapy.

The dose of the inventive composition administered to an individual (e.g., a human) in combination therapy may vary with the particular composition, the method of administration, and the particular stage of cancer being treated. The amount should be sufficient to produce a desirable response, such as a therapeutic or prophylactic response against cancer. In some embodiments, the amount of the composition is a therapeutically effective amount. In some embodiments, that amount of the composition is a prophylactically effective amount. In some embodiments, the amount of rapamycin or a derivative thereof in the composition is below the level that induces a toxicological effect (e.g., an effect above a clinically acceptable level of toxicity) or is at a level where a potential side effect can be controlled or tolerated when the composition is administered to the individual.

The composition comprising nanoparticles comprising rapamycin or a derivative thereof and a carrier protein (e.g., albumin) (also referred to as "nanoparticle composition") and the chemotherapeutic agent and/or hormone therapeutic agent can be administered simultaneously (e.g., simultaneous administration) and/or sequentially (e.g., sequential administration).

In some embodiments, the nanoparticle composition and the chemotherapeutic agent and/or hormone therapeutic agents (including the specific chemotherapeutic agents described herein) are administered simultaneously. The term "simultaneous administration," as used herein, means that the nanoparticle composition and the chemotherapeutic agent and/or hormone therapeutic agent are administered with a time separation of no more than about 15 minute(s), such as no more than about any of 10, 5, or 1 minutes. When the drugs are administered simultaneously, the rapamycin or a derivative thereof in the nanoparticles and the chemotherapeutic agent and/or hormone therapeutic agent may be contained in the same composition (e.g., a composition comprising both the nanoparticles and the chemotherapeutic agent) or in separate compositions (e.g., the nanoparticles are contained in one composition and the chemotherapeutic agent is contained in another composition). For example, rapamycin or a derivative thereof and a carrier protein (e.g., albumin) and the chemotherapeutic agent may be present in a single composition containing at least two different nanoparticles, wherein some of the nanoparticles in the composition comprise rapamycin or a derivative thereof and a carrier protein, and some of the other nanoparticles in the composition comprise the chemotherapeutic agent and a carrier protein. The invention contemplates and encompasses such compositions. In some embodiments, only rapamycin or a derivative thereof is contained in nanoparticles. In some embodiments, simultaneous administration of the rapamycin or a derivative thereof in the nanoparticle composition and the chemotherapeutic agent and/or hormone therapeutic agent can be combined with supplemental doses of the rapamycin or a derivative thereof and/or the chemotherapeutic agent and/or hormone therapeutic agent.

In some embodiments, the rapamycin or a derivative thereof nanoparticle composition and the chemotherapeutic agent and/or hormone therapeutic agent are administered sequentially. The term "sequential administration" as used herein means that the rapamycin or a derivative thereof in the nanoparticle composition and the chemotherapeutic agent and/or hormone therapeutic agent are administered with a time separation of more than about 15 minutes, such as more than about any of 20, 30, 40, 50, 60 or more minutes. Either the rapamycin or a derivative thereof nanoparticle composition or the chemotherapeutic agent and/or hormone therapeutic agent may be administered first. The rapamycin or a derivative thereof nanoparticle composition and the chemotherapeutic agent and/or hormone therapeutic agent are contained in separate compositions, which may be contained in the same or different packages.

In some embodiments, the administration of the rapamycin or a derivative thereof nanoparticle composition and the chemotherapeutic agent and/or hormone therapeutic agent are concurrent, e.g., the administration period of the nanoparticle composition and that of the chemotherapeutic agent and/or hormone therapeutic agent overlap with each other. In some embodiments, the administration of the rapamycin or a derivative thereof nanoparticle composition and the chemotherapeutic agent and/or hormone therapeutic agent are non-concurrent. For example, in some embodiments, the administration of the rapamycin or a derivative thereof nanoparticle composition is terminated before the chemotherapeutic agent and/or hormone therapy is administered. In some embodiments, the administration of the chemotherapeutic agent and/or hormone therapy is terminated before the rapamycin or a derivative thereof nanoparticle composition is administered. The time period between these two non-concurrent administrations can range from about two to eight weeks, such as about four weeks.

The dosing frequency of the rapamycin or a derivative thereof-containing nanoparticle composition and the chemotherapeutic agent and/or hormone therapy may be adjusted over the course of the treatment, based on the judgment of the administering physician. When administered separately, the rapamycin or a derivative thereof-containing nanoparticle composition and the chemotherapeutic agent and/or hormone therapy can be administered at different dosing frequency or intervals. For example, the rapamycin or a derivative thereof-containing nanoparticle composition can be administered weekly, while a chemotherapeutic agent and/or hormone therapeutic agent can be administered more or less frequently. In some embodiments, sustained continuous release formulation of the rapamycin or a derivative thereof-containing nanoparticle and/or chemotherapeutic agent and/or hormone therapeutic agent may be used. Various formulations and devices for achieving sustained release are known in the art.

The rapamycin or a derivative thereof nanoparticle composition and the chemotherapeutic agent and/or hormone therapeutic agent can be administered using the same route of administration or different routes of administration. In some embodiments (for both simultaneous and sequential administrations), the rapamycin or a derivative thereof in the nanoparticle composition and the chemotherapeutic agent and/or hormone therapeutic agent are administered at a predetermined ratio. For example, in some embodiments, the ratio by weight of the rapamycin or a derivative thereof in the nanoparticle composition and the chemotherapeutic agent or the hormone therapeutic agent is about 1 to 1. In some embodiments, the weight ratio may be between about 0.001 to about 1 and about 1000 to about 1, or between about 0.01 to about 1 and 100 to about 1. In some embodiments, the ratio by weight of the rapamycin or a derivative thereof in the nanoparticle composition and the chemotherapeutic agent or hormone therapeutic agent is less than any of about 100:1, 50:1, 30:1, 10:1, 9:1, 8:1, 7.5:1, 7:1, 6:1, 5:1, 4:1, 3:1, 2:1, and 1:1. In some embodiments, the ratio by weight of the rapamycin or a derivative thereof in the nanoparticle composition and the chemotherapeutic agent or hormone therapeutic agent is more than any of about 1:1, 2:1, 3:1, 4:1, 5:1, 6:1, 7:1, 7.5:1, 8:1, 9:1, 30:1, 50:1, 100:1. Other ratios are contemplated.

The doses required for the rapamycin or a derivative thereof and/or the chemotherapeutic agent and/or hormone therapeutic agent may (but not necessarily) be lower than what is normally required when each agent is administered alone. Thus, in some embodiments, a subtherapeutic amount of the rapamycin or a derivative thereof in the nanoparticle composition and/or the chemotherapeutic agent and/or hormone therapeutic agent are administered. "Subtherapeutic amount" or "subtherapeutic level" refer to an amount that is less than the therapeutic amount, that is, less than the amount normally used when the rapamycin or a derivative thereof in the nanoparticle composition and/or the chemotherapeutic agent and/or hormone therapeutic agent are administered alone. The reduction may be reflected in terms of the amount administered at a given administration and/or the amount administered over a given period of time (reduced frequency).

In some embodiments, enough chemotherapeutic agent and/or hormone therapeutic agent is administered so as to allow reduction of the normal dose of the rapamycin or a derivative thereof in the nanoparticle composition required to effect the same degree of treatment by at least about any of 5%, 10%, 20%, 30%, 50%, 60%, 70%, 80%, 90%, or more. In some embodiments, enough rapamycin or a derivative thereof in the nanoparticle composition is administered so as to allow reduction of the normal dose of the chemotherapeutic agent and/or hormone therapeutic agent required to affect the same degree of treatment by at least about any of 5%, 10%, 20%, 30%, 50%, 60%, 70%, 80%, 90%, or more.

In some embodiments, the dose of both the rapamycin or a derivative thereof in the nanoparticle composition and the chemotherapeutic agent and/or hormone therapeutic agent are reduced as compared to the corresponding normal dose of each when administered alone. In some embodiments, both the rapamycin or a derivative thereof in the nanoparticle composition and the chemotherapeutic agent and/or hormone therapeutic agent are administered at a subtherapeutic, e.g., reduced level. In some embodiments, the dose of the nanoparticle composition and/or the chemotherapeutic agent is substantially less than the established maximum toxic dose (MTD). For example, the dose of the rapamycin or a derivative thereof nanoparticle composition and/or the chemotherapeutic agent and/or hormone therapeutic agent is less than about 50%, 40%, 30%, 20%, or 10% of the MTD.

A combination of the administration configurations described herein can be used. The combination therapy methods described herein may be performed alone or in conjunction with another therapy, such as surgery, radiation, gene therapy, immunotherapy, bone marrow transplantation, stem cell transplantation, hormone therapy, targeted therapy, cryotherapy, ultrasound therapy, photodynamic therapy, and/or chemotherapy and the like. Additionally, a person having a greater risk of developing the proliferative disease may receive treatments to inhibit or and/or delay the development of the disease.

As will be understood by those of ordinary skill in the art, the appropriate doses of chemotherapeutic agents and/or hormone therapeutic agent will be approximately those already employed in clinical therapies wherein the chemotherapeutic agent and/or hormone therapeutic agent are administered alone or in combination with other chemotherapeutic agents. Variation in dosage will likely occur depending on the condition being treated. As described above, in some embodiments, the chemotherapeutic agents and/or hormone therapeutic agents may be administered at a reduced level.

The dose of the rapamycin or its derivative therein in the nanoparticle composition will vary with the nature of the combination therapy and the particular disease being treated. In some embodiments, the amount of rapamycin or a derivative thereof in the nanoparticle composition in the combination therapy is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of rapamycin or derivative thereof in the effective amount of the nanoparticle composition (e.g., a unit dosage form) for combination therapy is in the range of about 54 mg to about 540 mg, such as about 180 mg to about 270 mg or about 216 mg. In some embodiments, the concentration of the rapamycin in the nanoparticle composition for use in combination therapy is dilute (about 0.1 mg/ml) or concentrated (about 100 mg/ml), including for example any of about 0.1 to about 50 mg/ml, about 0.1 to about 20 mg/ml, about 1 to about 10 mg/ml, about 2 mg/ml to about 8 mg/ml, about 4 to about 6 mg/ml, about 5 mg /ml. In some embodiments, the concentration of the rapamycin or a derivative thereof in the nanoparticle composition in combination therapy is at least about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml.

Exemplary effective amounts of rapamycin or a derivative thereof in the nanoparticle composition for use in combination therapy include, but are not limited to, about any of 25 $mg/m^2$, 30 $mg/m^2$, 50 $mg/m^2$, 60 $mg/m^2$, 75 $mg/m^2$, 80 $mg/m^2$, 90 $mg/m^2$, 100 $mg/m^2$, 120 $mg/m^2$, 160 $mg/m^2$, 175 $mg/m^2$, 180 $mg/m^2$, 200 $mg/m^2$, 210 $mg/m^2$, 220 $mg/m^2$, 250 $mg/m^2$, 260 $mg/m^2$, 300 $mg/m^2$, 350 $mg/m^2$, 400 $mg/m^2$, 500 $mg/m^2$, 540 $mg/m^2$, 750 $mg/m^2$, 1000 $mg/m^2$, or 1080 $mg/m^2$ rapamycin. In various embodiments, the rapamycin or a derivative thereof in the nanoparticle composition includes less than about any of 350 m g/$m^2$, 300 $mg/m^2$, 250 $mg/m^2$, 200 $mg/m^2$, 150 $mg/m^2$, 120 $mg/m^2$, 100 $mg/m^2$, 90 $mg/m^2$, 50 $mg/m^2$, or 30 $mg/m^2$ rapamycin or a derivative thereof. In some embodiments, the amount of the rapamycin or a derivative thereof per administration in combination therapy is less than about any of 25 $mg/m^2$, 22 $mg/m^2$, 20 $mg/m^2$, 18 $mg/m^2$, 15 $mg/m^2$, 14 $mg/m^2$, 13 $mg/m^2$, 12 $mg/m^2$, 11 $mg/m^2$, 10 $mg/m^2$, 9 $mg/m^2$, 8 $mg/m^2$, 7 $mg/m^2$, 6 $mg/m^2$, 5 $mg/m^2$, 4 $mg/m^2$, 3 $mg/m^2$, 2 $mg/m^2$, or 1 $mg/m^2$. In some embodiments, the effective amount of rapamycin or a derivative thereof in the composition for use in combination therapy is included in any of the following ranges: about 1 to about 5 $mg/m^2$, about 5 to about 10 $mg/m^2$, about 10 to about 25 $mg/m^2$, about 25 to about 50 $mg/m^2$, about 50 to about 75 $mg/m^2$, about 75 to about 100 $mg/m^2$, about 100 to about 125 $mg/m^2$, about 125 to about 150 $mg/m^2$, about 150 to about 175 $mg/m^2$, about 175 to about 200 $mg/m^2$, about 200 to about 225 $mg/m^2$, about 225 to about 250 $mg/m^2$, about 250 to about 300 $mg/m^2$, about 300 to about 350 $mg/m^2$, or about 350 to about 400 $mg/m^2$. Preferably, the effective amount of rapamycin or a derivative thereof in the composition for use in combination therapy is about 30 to about 300 $mg/m^2$, such as about 100 to about 150 $mg/m^2$, about 120 $mg/m^2$, about 130 $mg/m^2$, or about 140 $mg/m^2$.

In some embodiments of any of the above aspects, the effective amount of rapamycin or a derivative thereof in the nanoparticle composition for use in combination therapy includes at least about any of 1 mg/kg, 2.5 mg/kg, 5 mg/kg, 7.5 mg/kg, 10 mg/kg, 15 mg/kg, or 20 mg/kg. In various embodiments, the effective amount of rapamycin or a derivative thereof in the nanoparticle composition for use in combination therapy includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 5 mg/kg, or 1 mg/kg rapamycin or a derivative thereof.

Exemplary dosing frequencies of rapamycin or a derivative thereof in the nanoparticle composition for use in combination therapy include, but are not limited to, weekly without break; weekly, three out of four weeks; once every three weeks; once every two weeks; weekly, two out of three weeks. In some embodiments, the rapamycin or a derivative thereof in the nanoparticle composition is administered in combination about once every 2 weeks, once every 3 weeks, once every 4 weeks, once every 6 weeks, or once every 8 weeks. In some embodiments, the rapamycin or a derivative thereof in the nanoparticle composition is administered in combination therapy at least about any of 1×, 2×, 3×, 4×, 5×, 6×, or 7× (i.e., daily) a week. In some embodiments, the intervals between each administration in combination therapy are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration in combination therapy are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

The administration of the rapamycin or a derivative thereof in the nanoparticle composition in combination therapy can be extended over an extended period of time, such as from about a month up to about seven years. In some embodiments, the rapamycin or a derivative thereof in the nanoparticle composition is administered over a period of at least about any of 2, 3, 4, 5, 6, 7, 8, 9, 10, 11, 12, 18, 24, 30, 36, 48, 60, 72, or 84 months. In some embodiments, the rapamycin or derivative thereof nanoparticle composition is administered over a period of at least one month, wherein the interval between each administration is no more than about a week, and wherein the dose of the rapamycin or a derivative thereof in the nanoparticle composition at each administration is about 0.25 mg/m$^2$ to about 75 mg/m$^2$, such as about 0.25 mg/m$^2$ to about 25 mg/m$^2$ or about 25 mg/m$^2$ to about 50 mg/m$^2$.

In some embodiments, the dosage of rapamycin in the nanoparticle composition in the combination therapy can be in the range of 100-400 mg/m$^2$ when given on a 3 week schedule, or 50-250 mg/m$^2$ when given on a weekly schedule. Preferably, the amount of rapamycin is about 80 to about 180 mg/m$^2$ (e.g., about 100 mg/m$^2$ to about 150 mg/m$^2$, such as about 120 mg/m$^2$).

Other exemplary dosing schedules for the administration of the nanoparticle composition (e.g., rapamycin/albumin nanoparticle composition) in combination therapy include, but are not limited to, 100 mg/m$^2$, weekly, without break; 75 mg/m$^2$ weekly, 3 out of four weeks; 100 mg/m$^2$, weekly, 3 out of 4 weeks; 125 mg/m$^2$, weekly, 3 out of 4 weeks; 125 mg/m$^2$, weekly, 2 out of 3 weeks; 130 mg/m$^2$, weekly, without break; 175 mg/m$^2$, once every 2 weeks; 260 mg/m$^2$, once every 2 weeks; 260 mg/m$^2$, once every 3 weeks; 180-300 mg/m$^2$, every three weeks; 60-175 mg/m$^2$, weekly, without break; 20-150 mg/m$^2$ twice a week; and 150-250 mg/m$^2$ twice a week. The dosing frequency of the composition may be adjusted over the course of the treatment based on the judgment of the administering physician.

The rapamycin or a derivative thereof nanoparticle compositions described herein can be administered to an individual (such as human) during combination therapy via various routes, such as parenterally, including intravenous, intra-arterial, intraperitoneal, intrapulmonary, oral, inhalation, intravesicular, intramuscular, intra-tracheal, subcutaneous, intraocular, intrathecal, or transdermal. For example, the nanoparticle composition can be administered by inhalation to treat conditions of the respiratory tract. The rapamycin or a derivative thereof nanoparticle compositions can be used to treat respiratory conditions such as pulmonary fibrosis, broncheolitis obliterans, lung cancer, bronchoalveolar carcinoma, and the like. In some embodiments, the nanoparticle compositions is administrated intravenously. In some embodiments, the nanoparticle compositions is administered orally.

In some embodiments, the nanoparticle composition of the rapamycin or a derivative thereof and the chemotherapeutic agent is administered according to any of the dosing regimes described in Table 1.

In some embodiments, there is provided a method of treating cancer in an individual comprising administering to the individual: a) an effective amount of a composition comprising nanoparticles comprising a rapamycin or a derivative thereof and an albumin, and b) an effective amount of at least one other chemotherapeutic agent as provided in Rows 1 to 53 in Table 1. In some embodiments, the administration of the nanoparticle composition and the chemotherapeutic agent may be any of the dosing regimes as indicated in Rows 1 to 53 in Table 1. In some embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer. In some embodiments, one or more symptoms of the cancer are ameliorated. In some embodiments, the cancer is delayed or prevented.

TABLE 1

| Row No. | Combination | Regime/Dosage |
|---|---|---|
| 1. | RAPA + Carboplatin + Herceptin ® | RAPA: Rapamycin or a derivative thereof: any doses or regimes described above for combination therapy<br>Carbo: AUC = 2 D 1, 8, 15 q4wk × 6<br>Herceptin ®: 4 mg/kg on wk 1, 2 mg/kg all subsequent weeks |

TABLE 1-continued

| Row No. | Combination | Regime/Dosage |
|---|---|---|
| 2. | RAPA alone (+Herceptin ®) | RAPA: Rapamycin or a derivative thereof: any doses or regimes described above for combination therapy |
| 3. | RAPA + Navelbine ® (±G-CSF) | L1: Rapamycin or a derivative thereof: any doses or regimes described above for combination therapy<br>Nav: 15 mg/m²<br>L2: Rapamycin or a derivative thereof: any doses or regimes described above for combination therapy<br>Nav: 20 mg/m²<br>L3: Rapamycin or a derivative thereof: any doses or regimes described above for combination therapy<br>Nav: 22.5 mg/m²<br>L4: Rapamycin or a derivative thereof: any doses or regimes described above for combination therapy<br>Nav: 25 mg/m²<br>L5: Rapamycin or a derivative thereof: any doses or regimes described above for combination therapy<br>Nav: 25 mg/m²<br>qwk all levels |
| 4. | RAPA + Xeloda ® | RAPA: Rapamycin or a derivative thereof: any doses or regimes described above for combination therapy<br>Xeloda ®: 825 mg/m² D 1-14 q3wk |
| 5. | RAPA + Anthracycline | |
| 6. | RAPA + Gemcitabine | RAPA: Rapamycin or a derivative thereof: any doses or regimes described above for combination therapy<br>Gem: 1000 mg/m2 qwk × 2/3 |
| 7. | RAPA + Lapatinib | Rapamycin or a derivative thereof: any doses or regimes described above for combination therapy<br>Lapatinib: starting at 1000 mg/d × 2 days |
| 8. | RAPA + FEC (+Herceptin ®) | RAPA: Rapamycin or a derivative thereof: any doses or regimes described above for combination therapy<br>FEC: 4 cycles (+Herceptin ® for HER2+ pts) |
| 9. | RAPA + Carboplatin + Avastin ® | RAPA: Rapamycin or a derivative thereof: any doses or regimes described above for combination therapy<br>Carbo: AUC = 2 qwk D 1, 8, 15<br>Avastin ®: 10 mg/m² q2wk |
| 10. | RAPA + Avastin ® | RAPA: Rapamycin or a derivative thereof: any doses or regimes described above for combination therapy + Avastin ® |
| 11. | RAPA + Xeloda ® + Lapatinib | RAPA: Rapamycin or a derivative thereof: any doses or regimes described above for combination therapy |
| 12. | RAPA + Gemcitabine | RAPA: Rapamycin or a derivative thereof: any doses or regimes described above for combination therapy<br>Gem: 1250 mg/m² D 1, 8 q3wk |
| 13. | RAPA + Sutent ® | |
| 14. | RAPA + AC + G-CSF (+Herceptin ®) | AC + G-CSF q2wk × 4 followed by RAPA: Rapamycin or a derivative thereof: any doses or regimes described above for combination therapy (+Herceptin ® for HER2+ pts) |
| 15. | RAPA + AC + G-CSF (+Herceptin ®) | Dose dense AC + G-CSF followed by RAPA: Rapamycin or a derivative thereof: any doses or regimes described above for combination therapy (+Herceptin ® for HER2+ pts) |
| 16. | RAPA + AC | AC followed by RAPA: Rapamycin or a derivative thereof: any doses or regimes described above for combination therapy |
| 17. | RAPA + AC (+G-CSF) | AC q2wk followed by RAPA: Rapamycin or a derivative thereof: any doses or regimes described above for combination therapy<br>Rx length 16 wks |
| 18. | RAPA + AC (+Avastin ®) | Dose dense AC followed by RAPA: Rapamycin or a derivative thereof: any doses or regimes described above for combination therapy (+Avastin ® in HER2+ pts) |
| 19. | RAPA + AC | AC (such as about 60 mg/m² adriamycin and 600 mg/m² cyclophosphamide, once every two weeks) followed by RAPA: Rapamycin or a derivative thereof: any doses or regimes described above for combination therapy |
| 20. | RAPA + AC + Neulasta ® | AC followed by RAPA: Rapamycin or a derivative thereof: any doses or regimes described above for combination therapy |
| 21. | RAPA + FEC (+Herceptin ®) | RAPA: Rapamycin or a derivative thereof: any doses or regimes described above for combination therapy followed by<br>5-FU: 500 mg/m² q3wk<br>Epirubicin: 100 mg/m²<br>(without Herceptin ®) or<br>Epirubicin: 75 mg/m²<br>(with Herceptin ® for HER2+ pts)<br>Cyclophosphamide: 500 mg/m² q3wk |

TABLE 1-continued

| Row No. | Combination | Regime/Dosage |
|---|---|---|
| 22. | RAPA + Gemcitabine + Epirubicin | Arm 1: Neoadjuvant: Gem: 2000 mg/m$^2$, RAPA: Rapamycin or a derivative thereof: any doses or regimes described above for combination therapy, Epi 50 mg/m$^2$ q2wk × 6<br>Arm 2: Adjuvant: Gem: 2000 mg/m$^2$, RAPA: Rapamycin or a derivative thereof: any doses or regimes described above for combination therapy |
| 23. | RAPA + Herceptin ® + Navelbine | RAPA: Rapamycin or a derivative thereof: any doses or regimes described above for combination therapy + Herceptin ® followed by Navelbine ® + Herceptin ® |
| 24. | RAPA + Carboplatin (+Herceptin ®) + AC | TAC vs AC followed by RAPA: Rapamycin or a derivative thereof: any doses or regimes described above for combination therapy + carbo vs AC followed by RAPA: Rapamycin or a derivative thereof: any doses or regimes described above for combination therapy + carbo + Herceptin ® |
| 25. | RAPA + Capecitabine | RAPA: Rapamycin or a derivative thereof: any doses or regimes described above for combination therapy<br>Xeloda ® 850 mg/m$^2$ D 1-14 q3wk × 4 |
| 26. | RAPA + Carboplatin (+Avastin ®) | RAPA: Rapamycin or a derivative thereof: any doses or regimes described above for combination therapy<br>Carbo qwk + Avastin ® in HER2+ pts |
| 27. | RAPA + Carboplatin + Herceptin ® + Avastin ® | RAPA: Rapamycin or a derivative thereof: any doses or regimes described above for combination therapy<br>Carbo: AUC = 5 + Herceptin ® + Avastin ®<br>4 week cycle × 6 |
| 28. | RAPA + Lapatinib | RAPA: Rapamycin or a derivative thereof: any doses or regimes described above for combination therapy<br>Lapatinib: 1000 mg/day |
| 29. | RAPA + Capecitabine | RAPA: Rapamycin or a derivative thereof: any doses or regimes described above for combination therapy<br>Xeloda ®: 1000 mg/m$^2$ D 1-14 q3wk × 4 |
| 30. | RAPA ± Avastin ® + AC (+G-CSF) | RAPA: Rapamycin or a derivative thereof: any doses or regimes described above for combination therapy ± Avastin ® followed by A qwk + C daily |
| 31. | RAPA + AC | RAPA: Rapamycin or a derivative thereof: any doses or regimes described above for combination therapy followed by AC |
| 32. | RAPA + Carboplatin + Avastin ® | RAPA: Rapamycin or a derivative thereof: any doses or regimes described above for combination therapy<br>Carbo: AUC = 6 q3wk<br>Avastin ®: 15 mg/kg<br>4 cycles |
| 33. | RAPA + Carboplatin | RAPA: Rapamycin or a derivative thereof: any doses or regimes described above for combination therapy<br>Carbo fixed at AUC = 6 q3wk |
| 34. | RAPA + Carboplatin + Avastin ® | |
| 35. | RAPA + Gemcitabine or RAPA + Avastin ® | |
| 36. | RAPA + Carboplatin + Avastin ® | RAPA: Rapamycin or a derivative thereof: any doses or regimes described above for combination therapy<br>Carbo: AUC = 6 q3wk + Avastin ® |
| 37. | RAPA + Alimta ® | RAPA: Rapamycin or a derivative thereof: any doses or regimes described above for combination therapy<br>Pemetrexed: 500 mg q3wk |
| 38. | RAPA + Cisplatin | |
| 39. | RAPA + Navelbine ® + Cisplatin | |
| 40. | RAPA + Carboplatin | RAPA: Rapamycin or a derivative thereof: any doses or regimes described above for combination therapy<br>Carbo: AUC = 6 q3wk |
| 41. | RAPA + Carboplatin | RAPA: Rapamycin or a derivative thereof: any doses or regimes described above for combination therapy<br>Carbo: AUC = 6 |
| 42. | RAPA + Avastin ® | RAPA: Rapamycin or a derivative thereof: any doses or regimes described above for combination therapy<br>Avastin ®: 10 mg/m$^2$ q2wk |
| 43. | RAPA + 5-FU + Cisplatin | RAPA: Rapamycin or a derivative thereof: any doses or regimes described above for combination therapy<br>5-FU: 750 mg/m$^2$ CIV × 5<br>cisplatin: 75 mg/m$^2$ D 1<br>followed by XRT/surgery |
| 44. | RAPA + Cetuximab | |
| 45. | RAPA + Satraplatin | |
| 46. | RAPA + Gemcitabine | RAPA: Rapamycin or a derivative thereof: any doses or regimes described above for combination therapy<br>Gemcitabine: 1000 mg/m$^2$ D 1 and D 8 |

TABLE 1-continued

| Row No. | Combination | Regime/Dosage |
|---|---|---|
| 47. | RAPA + Gefitinib | RAPA: Rapamycin or a derivative thereof: any doses or regimes described above for combination therapy<br>Gefitinib starting at 1000 mg/d × 2 |
| 48. | RAPA + Sorafenib + Carboplatin | RAPA: Rapamycin or a derivative thereof: any doses or regimes described above for combination therapy<br>Sorafenib: D 2-19<br>Carbo: AUC = 6 D 1 |
| 49. | RAPA + Capecitabine | RAPA: Rapamycin or a derivative thereof: any doses or regimes described above for combination therapy + Xeloda ® at a range of about 500-2500 mg/m$^2$ (such as any of about 550 mg/m$^2$, 650 mg/m$^2$, 85 mg/m$^2$, 850 mg/m$^2$, 100 mg/m$^2$, 1250 mg/m$^2$) |
| 50. | RAPA + Gemcitabine | Weekly |
| 51. | RAPA + anti-angiogenic agent(s) | |
| 52. | RAPA + proteasome inhibitor(s) | |
| 53. | RAPA + tyrosine kinase inhibitor(s) | |
| 54. | RAPA + EGFR inhibitor(s) | |

As used in herein (for example in Table 1), RAPA refers to a composition comprising nanoparticles comprising rapamycin or a derivative thereof and a carrier protein (e.g., albumin); GW572016 refers to lapatinib; Xel refers to capecitabine or Xeloda®; bevacizumab is also known as Avastin®; trastuzumab is also known as Herceptin®; pemetrexed is also known as Alimta®; cetuximab is also known as Erbitux®; gefitinib is also known as Iressa®; FEC refers to a combination of 5-fluorouracil, Epirubicin and Cyclophosphamide; AC refers to a combination of Adriamycin plus Cyclophosphamide.

As used herein (for example in Table 1), AUC refers to area under curve; q4wk refers to a dose every 4 weeks; q3wk refers to a dose every 3 weeks; q2wk refers to a dose every 2 weeks; qwk refers to a weekly dose; qwk x 3/4 refers to a weekly dose for 3 weeks with the 4$^{th}$ week off; qwk x 2/3 refers to a weekly dose for 2 weeks with the 3$^{rd}$ week off.

In some embodiments, the present invention provides a method of treating cancer comprising a first therapy comprising administering nanoparticles comprising rapamycin or a derivative thereof and a carrier protein (e.g., albumin) and a second therapy comprising surgery, radiation, gene therapy, immunotherapy, bone marrow transplantation, stem cell transplantation, targeted therapy, cryotherapy, ultrasound therapy, and/or photodynamic therapy. In some embodiments, the method comprises a) a first therapy comprising administering to the individual a composition comprising nanoparticles of rapamycin and an albumin; and b) a second therapy comprising surgery, radiation, gene therapy, immunotherapy, bone marrow transplantation, stem cell transplantation, targeted therapy, cryotherapy, ultrasound therapy, and/or photodynamic therapy. In some embodiments, the cancer may be prostate cancer. In some embodiments, the second therapy is radiation therapy. In some embodiments, the second therapy is surgery.

The administration of the rapamycin or a derivative thereof nanoparticle composition may be prior to the radiation and/or surgery, after the radiation and/or surgery, or concurrent with the radiation and/or surgery. For example, the administration of the nanoparticle composition may precede or follow the radiation and/or surgery therapy by intervals ranging from minutes to weeks. In some embodiments, the time period between the first and the second therapy is such that the rapamycin or a derivative thereof nanoparticles and the radiation/surgery would still be able to exert an advantageously combined effect on the cell. For example, the rapamycin or derivative thereof in the nanoparticle composition may be administered less than about any of 1, 3, 6, 9, 12, 18, 24, 48, 60, 72, 84, 96, 108, 120 hours prior to the radiation and/or surgery. In some embodiments, the nanoparticle composition is administered less than about 9 hours prior to the radiation and/surgery. In some embodiments, the nanoparticle composition is administered less than about any of 1, 2, 3, 4, 5, 6, 7, 8, 9, or 10 days prior to the radiation/surgery. In some embodiments, the rapamycin or a derivative thereof in the nanoparticle composition is administered less than about any of 1, 3, 6, 9, 12, 18, 24, 48, 60, 72, 84, 96, 108, or 120 hours after the radiation and/or surgery. In some embodiments, it may be desirable to extend the time period for treatment significantly, where several days to several weeks lapse between the two therapies.

Radiation contemplated herein includes, for example, γ-rays, X-rays (external beam), and the directed delivery of radioisotopes to tumor cells. Other forms of DNA damaging factors are also contemplated such as microwaves and UV irradiation are also contemplated. Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted.

When the radiation comprises use of radioactive isotopes, the isotope may be conjugated to a targeting agent, such as a therapeutic antibody, which carries the radionucleotide to the target tissue. Suitable radioactive isotopes include, but are not limited to, astatine$^{211}$, carbon$^{14}$, chromium$^{51}$, chlorine$^{36}$, iron$^{57}$, cobalt$^{58}$, copper$^{67}$, Eu$^{152}$, gallium$^{67}$, hydrogen$^{3}$, iodine$^{123}$, iodine$^{131}$, indium", iron$^{59}$, phosphorus$^{32}$, rhenium$^{186}$, selenium$^{75}$, sulphur$^{35}$, technicium$^{99m}$, and/or yttrium$^{90}$.

In some embodiments, enough radiation is applied to the individual so as to allow reduction of the normal dose of the rapamycin or a derivative thereof in the nanoparticle composition required to affect the same degree of treatment by at least about any of 5%, 10%, 20%, 30%, 50%, 60%, 70%, 80%, 90%, or more. In some embodiments, enough rapamycin or derivative thereof in the nanoparticle composition is administered so as to allow reduction of the normal dose of the radiation required to affect the same degree of treatment by at least about any of 5%, 10%, 20%, 30%, 50%, 60%, 70%, 80%, 90%, or more. In some embodiments, the dose of both the rapamycin or a derivative thereof in the nanoparticle composition and the radiation are reduced as compared to the corresponding normal dose of each when used alone.

In some embodiments, the combination of administration of the rapamycin or a derivative thereof nanoparticle composition and the radiation therapy produce supra-additive effect. In some embodiments, the rapamycin or a derivative thereof in the nanoparticle composition is administered once at the dose of about 50 mg to 540 mg or about 30 mg/m$^2$ to 300 mg/m$^2$, and the radiation is applied five times at 80 Gy daily.

Administration of rapamycin or a derivative thereof nanoparticle compositions disclosed above in conjunction with administration of chemotherapeutic agent and/or hormone therapeutic agent is equally applicable to those in conjunction with radiation therapy and/or surgery.

In some embodiments, the nanoparticle composition of the rapamycin or a derivative thereof nanoparticles and/or the chemotherapeutic agent is administered in conjunction with radiation according to any of the dosing regimes described in Table 2.

In some embodiments, there is provided a method of treating cancer in an individual comprises a) a first therapy comprising administering to the individual a composition comprising nanoparticles comprising rapamycin or a derivative thereof and an albumin; and b) a second therapy comprising radiation as provided in Rows 1 to 11 in Table 2. In some embodiments, the administration of the nanoparticle composition and the chemotherapeutic agent may be any of the dosing regimes as indicated in Rows 1 to 11 in Table 2. In some embodiments, the cancer is early stage cancer, non-metastatic cancer, primary cancer, advanced cancer, locally advanced cancer, metastatic cancer, cancer in remission, recurrent cancer, cancer in an adjuvant setting, cancer in a neoadjuvant setting, or cancer substantially refractory to hormone therapy. In some embodiments, the cancer is a solid tumor. In some embodiments, the cancer is not a solid tumor (i.e., other than a solid tumor). In some embodiments, the cancer is a plasmacytoma. In some embodiments, the cancer is multiple myeloma, renal cell carcinoma, prostate cancer, lung cancer, melanoma, brain cancer (e.g., glioblastoma), ovarian cancer, or breast cancer. In some embodiments, the cancer is a carcinoma (i.e., other than a carcinoma). In some embodiments, the cancer is not colon cancer (i.e., other than colon cancer). In some embodiments, the cancer is not breast cancer (i.e., other than breast cancer). In some embodiments, the cancer is not ovarian cancer, prostate cancer, or brain cancer.

TABLE 2

| Row No. | Combination | Regime/Dosage |
| --- | --- | --- |
| 1 | RAPA + Radiation | |
| 2 | RAPA + Carboplatin + Radiation | |
| 3 | RAPA + Carboplatin + Radiation | 1 cycle RAPA/Carbo induction followed by 2 or 3 times weekly pulse RAPA + radiation |
| 4 | RAPA + Carboplatin + Radiation | |
| 5 | RAPA + Carboplatin + Radiation | RAPA: Rapamycin or a derivative thereof: any doses or regimes described above for combination therapy + carbo + radiation followed by RAPA: Rapamycin or a derivative thereof: any doses or regimes described above for combination therapy + carbo |
| 6 | RAPA + Radiation | |
| 7 | RAPA + Cetuximab + Radiation | |
| 8 | RAPA + Carboplatin + 5-FU + Hydroxyurea + Radiation | Induction: RAPA: Rapamycin or a derivative thereof: any doses or regimes described above for combination therapy + carbo: AUC = 2 followed by Concurrent chemoradiation: RAPA: Rapamycin or a derivative thereof: any doses or regimes described above for combination therapy; 5-FU: 600 mg/m$^2$; hydroxyurea: 5000 mg BID |
| 9 | RAPA + Carboplatin + Erbitux ® + Radiation | RAPA: Rapamycin or a derivative thereof: any doses or regimes described above for combination therapy Eribitux ®: 400 mg/m$^2$ day 7, 250 mg/m$^2$ qwk × 7 Carbo: AUC = 1.5 qwk × 7 IMRT |
| 10 | RAPA + Gemcitabine + Radiation | Qwk |
| 11 | RAPA + Cisplatin + Radiation | |

Metronomic Therapy Regimes

The present invention also provides metronomic therapy regimes for any of the methods of treatment and methods of administration described herein. Exemplary metronomic therapy regimes and embodiments for the use of metronomic therapy regimes are discussed below and disclosed in U.S. Ser. No. 11/359,286, filed Feb. 21, 2006, published as U.S. Pub. No. 2006/0263434 (such as those described in paragraphs [0138] to [0157]), which is hereby incorporated by reference in its entirety. In some embodiments, the nanoparticle composition is administered over a period of at least one month, wherein the interval between each administration is no more than about a week, and wherein the dose of rapamycin or a derivative thereof at each administration is about 0.25% to about 25% of its maximum tolerated dose following a traditional dosing regime. In some embodiments, the nanoparticle composition is administered over a period of at least two months, wherein the interval between each administration is no more than about a week, and wherein the dose of rapamycin or a derivative thereof at each administration is about 1% to about 20% of its maximum tolerated dose following a traditional dosing regime. In some embodiments, the dose of rapamycin or a derivative thereof per administration is less than about any of 25%, 24%, 23%, 22%, 20%, 18%, 15%, 14%, 13%, 12%, 11%, 10%, 9%, 8%, 7%, 6%, 5%, 4%, 3%, 2%, or 1% of the maximum tolerated dose. In some embodiments, the nanoparticle composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, the composition is administered over a period of at least about any of 2, 3, 4, 5, 6, 7, 8, 9, 10, 11, 12, 18, 24, 30, 36, 48, 60, 72, or 84 months.

Pharmaceutical Agents

Provided herein are compositions comprising nanoparticles that comprise rapamycin for use in the methods of treatment of cancer, methods of administration, and dosing regimes described herein. In some embodiments, rapamycin may be rapamycin or its derivatives or pharmaceutically acceptable salts and accordingly the invention contemplates and includes all these embodiments. Rapamycin is sometimes referred to elsewhere as sirolimus, rapammune, or rapamune. Derivatives of rapamycin include, but are not limited to, compounds that are structurally similar to rapamycin or are in the same general chemical class as rapamycin.

In some embodiments, the derivative of rapamycin retains one or more similar biological, pharmacological, chemical and/or physical properties (including, for example, functionality) as rapamycin. In some embodiments, the rapamycin derivative has at least about any of 10%, 20%, 30%, 40%, 50%, 60%, 70%, 80%, 90%, 95% or 100% of an activity of rapamycin. For example, the decrease in the size of a tumor, the number of cancer cells, or the growth rate of a tumor caused by a rapamycin derivative is preferably at least about any of 10%, 20%, 30%, 40%, 50%, 60%, 70%, 80%, 90%, 95% or 100% of the corresponding decrease caused by the same amount of rapamycin. An exemplary rapamycin derivative includes benzoyl rapamycin, such as that disclosed in paragraph [0022] of WO 2006/089207, which is hereby incorporated by reference in its entirety. Other exemplary rapamycin derivatives include WY-090217, AY-22989, NSC-226080, SiiA-9268A, oxaazacyclohentriacontine, temsirolimus (CCI-779 (Wyeth)), everolimus (RAD001 (Novartis)), pimecrolimus (ASM981), SDZ-RAD, SAR943, ABT-578, AP23573, and Biolimus A9.

Carrier Proteins

Provide herein are compositions comprising nanoparticles that comprise rapamycin and a carrier protein for use methods of treatment of cancer, methods of administration, and dosage regimes described herein. In some embodiments, rapamycin may be rapamycin or its derivatives or pharmaceutically acceptable salts and accordingly the invention contemplates and includes all these embodiments. In some embodiments, the carrier protein is albumin. In some embodiments, the carrier protein is human serum albumin.

Examples of suitable carrier proteins include proteins normally found in blood or plasma, which include, but are not limited to, albumin, immunoglobulin including IgA, lipoproteins, apolipoprotein B, α-acid glycoprotein, β-2-macroglobulin, thyroglobulin, transferin, fibronectin, factor VII, factor VIII, factor IX, factor X, and the like. In some embodiments, the carrier protein is a non-blood protein, such as casein, α-lactalbumin, or β-lactoglobulin. The carrier proteins may either be natural in origin or synthetically prepared. In some embodiments, the pharmaceutical acceptable carrier comprises albumin, such as human serum albumin (HSA). HSA is a highly soluble globular protein of $M_r$ 65K and consists of 585 amino acids. HSA is the most abundant protein in the plasma and accounts for 70-80% of the colloid osmotic pressure of human plasma. The amino acid sequence of HSA contains a total of 17 disulphide bridges, one free thiol (Cys 34), and a single tryptophan (Trp 214). Other albumins are contemplated, such as bovine serum albumin. Use of such non-human albumins could be appropriate, for example, in the context of use of these compositions in non-human mammals, such as the veterinary animals (including domestic pets and agricultural animals).

Human serum albumin (HSA) has multiple hydrophobic binding sites (a total of eight for fatty acids, an endogenous ligand of HSA) and binds a diverse set of drugs, especially neutral and negatively charged hydrophobic compounds (Goodman et al., *The Pharmacological Basis of Therapeutics,* $9^{th}$ ed, McGraw-Hill New York (1996)). Two high affinity binding sites have been proposed in subdomains IIA and IIIA of HSA, which are highly elongated hydrophobic pockets with charged lysine and arginine residues near the surface which function as attachment points for polar ligand features (see, e.g., Fehske et al., *Biochem. Pharmcol.,* 30, 687-92 (1981), Vorum, *Dan. Med. Bull.,* 46, 379-99 (1999), Kragh-Hansen, *Dan. Med. Bull.,* 1441, 131-40 (1990), Curry et al., *Nat. Struct. Biol.,* 5, 827-35 (1998), Sugio et al., *Protein. Eng.,* 12, 439-46 (1999), He et al., *Nature,* 358, 209-15 (1992), and Carter et al., *Adv. Protein. Chem.,* 45, 153-203 (1994)).

The carrier protein (e.g., albumin) in the composition generally serves as a carrier for rapamycin or derivative thereof, i.e., the carrier protein in the composition makes the rapamycin or derivative thereof more readily suspendable in an aqueous medium or helps maintain the suspension as compared to compositions not comprising a carrier protein. This can avoid the use of toxic solvents for solubilizing rapamycin or a derivative thereof, and thereby can reduce one or more side effects of administration of rapamycin or a derivative thereof into an individual (e.g., human). In some embodiments, the composition is substantially free (e.g. free) of organic solvents or surfactants. A composition is "substantially free of organic solvent" or "substantially free of surfactant" if the amount of organic solvent or surfactant in the composition is not sufficient to cause one or more side effect(s) in an individual when the composition is administered to the individual.

Rapamycin is "stabilized" in an aqueous suspension if it remains suspended in an aqueous medium (e.g., without visible precipitation or sedimentation) for an extended period of time, such as for at least about any of 0.1, 0.2, 0.25, 0.5, 1, 2, 3, 4, 5, 6, 7, 8, 9, 10, 11, 12, 24, 36, 48, 60, or 72 hours. The suspension is generally, but not necessarily, suitable for administration to an individual (e.g., human). Stability of the suspension is generally (but not necessarily) evaluated at storage temperature, such as room temperature (e.g., 20-25° C.) or refrigerated conditions (e.g., 4° C.). For example, a suspension is stable at a storage temperature if it exhibits no flocculation or particle agglomeration visible to the naked eye or when viewed under the optical microscope at 1000 times, at about fifteen minutes after preparation of the suspension. Stability can also be evaluated under accelerated testing conditions, such as at a temperature that is higher than about 40° C.

In some embodiments, the composition comprises nanoparticles comprising (in various embodiments consisting essentially of) rapamycin and a carrier protein. When rapamycin is in a liquid form, the particles or nanoparticles are also referred to as droplets or nanodroplets. In some embodiments, rapamycin is coated with the carrier protein. Particles (such as nanoparticles) of poorly water soluble pharmaceutical agents have been disclosed in, for example, U.S. Pat. Nos. 5,916,596; 6,506,405; and 6,537,579 and also in U.S. Pat. App. Pub. No. 2005/0004002A1.

The amount of carrier protein in the composition described herein will vary depending on the rapamycin or derivative thereof and other components in the composition. In some embodiments, the composition comprises a carrier protein in an amount that is sufficient to stabilize the rapamycin in an aqueous suspension, for example, in the form of a stable colloidal suspension (e.g., a stable suspension of nanoparticles). In some embodiments, the carrier protein is in an amount that reduces the sedimentation rate of rapamycin in an aqueous medium. For particle-containing compositions, the amount of the carrier protein also depends on the size and density of particles of rapamycin.

In some embodiments of any of the aspects of the invention, the rapamycin or a derivative thereof is coated with a carrier protein, such as albumin (e.g., human serum albumin). In various embodiments, the composition comprises more than about any of 50%, 60%, 70%, 80%, 90%, 95%, or 99% of the rapamycin or derivative thereof in nanoparticle form. In some embodiments, the rapamycin or derivative thereof constitutes more than about any of 50%, 60%, 70%, 80%, 90%, 95%, or 99% of the nanoparticles by weight. In some embodiments, the nanoparticle has a non-polymeric matrix. In some embodiments, the rapamycin or derivative thereof is in an anhydrous, amorphous, and/or non-crystalline form. In some embodiments, the rapamycin or derivative thereof is amorphous. In some embodiments, the nanoparticles comprise a core of rapamucin or derivative thereof that is substantially free of polymeric materials (such as polymeric matrix).

In some embodiments, the albumin to rapamycin weight ratio in the nanoparticles or in the nanoparticle composition is about any of 18:1 or less, 15:1 or less, 14:1 or less, 13:1 or less, 12:1 or less, 11:1 or less, 10:1 or less, 9:1 or less, 8:1 or less, 7.5:1 or less, 7:1 or less, 6:1 or less, 5:1 or less, 4:1 or less, or 3:1 or less. In some embodiments, the composition comprises a stable aqueous suspension of particles (e.g., nanoparticles) comprising rapamycin or a derivative thereof and albumin (e.g., particles of rapamycin or a derivative thereof coated with albumin).

In some embodiments, the composition comprises nanoparticles of any shape (e.g., a spherical or non-spherical shape) with an average or mean diameter of no greater than about 1000 nanometers (nm), such as no greater than about any of 900 nm, 800 nm, 700 nm, 600 nm, 500 nm, 400 nm, 300 nm, 200 nm, or 100 nm. In some embodiments, the average or mean diameter of the particles is no greater than about 200 nm. In some embodiments, the average or mean diameter of the particles is between about 20 to about 400 nm. In some embodiments, the average or mean diameter of the particles is between about 40 to about 200 nm. In some embodiments, the particles are sterile-filterable.

In some embodiments, the nanoparticles comprise the rapamycin or a derivative thereof coated with a coating comprising the carrier protein (such as albumin). In some embodiments, the coating consists essentially of or consists of the carrier protein. In some embodiments, at least a portion of the carrier protein in the nanoparticle portion of the rapamycin (or rapamycin derivative) nanoparticle composition is crosslinked (for example crosslinked by disulfide bonds).

The nanoparticles described herein may be present in a dry formulation (e.g., lyophilized composition) or suspended in a biocompatible medium. Suitable biocompatible media include, but are not limited to, water, buffered aqueous media, saline, buffered saline, optionally buffered solutions of amino acids, optionally buffered solutions of proteins, optionally buffered solutions of sugars, optionally buffered solutions of vitamins, optionally buffered solutions of synthetic polymers, lipid-containing emulsions, and the like.

In some embodiments, the nanoparticles do not comprise a blood-insoluble gas or do not comprise gas-filled microbubbles.

The amount of carrier protein in the composition described herein will vary depending on the rapamycin or derivative thereof and other components in the composition. In some embodiments, the composition comprises a carrier protein in an amount that is sufficient to stabilize the rapamycin in an aqueous suspension, for example, in the form of a stable colloidal suspension (e.g., a stable suspension of nanoparticles). In some embodiments, the carrier protein is in an amount that reduces the sedimentation rate of rapamycin in an aqueous medium. The amount of the carrier protein also depends on the size and density of particles of rapamycin.

Also provided herein are methods of reducing side effects associated with administration of a poorly water soluble pharmaceutical agent to a human, comprising administering to a human a pharmaceutical composition comprising the poorly water soluble pharmaceutical agent, and a biocompatible polymer (such as a carrier protein). For example, the invention provides methods of reducing various side effects associated with administration of the poorly water soluble pharmaceutical agent, including, but not limited to, myelosuppression, neurotoxicity, hypersensitivity, inflammation, venous irritation, phlebitis, pain, skin irritation, neutropenic fever, anaphylactic reaction, hematologic toxicity, and cerebral or neurologic toxicity, and combinations thereof. In some embodiments, there is provided a method of reducing hypersensitivity reactions associated with administration of rapamycin or a derivative thereof, including, for example, severe skin rashes, hives, flushing, dyspnea, tachycardia, cancer (e.g., lymphoma); chest pain; black, tarry stools; general feeling of illness, shortness of breath; swollen glands; weight loss; yellow skin and eyes, abdominal pain; unexplained anxiousness; bloody or cloudy urine; bone pain; chills; confusion; convulsions (seizures); cough; decreased urge to urinate; fast, slow, or irregular heartbeat; fever; frequent urge to urinate; increased thirst; loss of appetite; lower back or side pain; mood changes; muscle pain or cramps; nausea or vomiting; numbness or tingling around lips, hands, or feet; painful or difficult urination; rash; sore throat; sores or white spots on lips or in mouth; swelling of hands, ankles, feet, or lower legs; swollen glands; trouble breathing; unusual bleeding or bruising; unusual tiredness or weakness; weakness or heaviness of legs, skin ulcer or sores, weight gain, acne; constipation; diarrhea; difficulty in moving; headache; loss of energy or weakness; muscle pain or stiffness; pain; shaking or trembling; trouble sleeping; nosebleed; and/or swelling of the face. These side effects, however, are merely exemplary and other side effects, or combination of side effects, associated with rapamycin can be reduced. The side effects may be immediate or delayed (such as not occurring for a few days, weeks, months, or years after treatment begins).

Antimicrobial Agents in Compositions

In some embodiments, the compositions of the invention also includes an antimicrobial agent (e.g., an agent in addition to the rapamycin or derivative thereof in an amount sufficient to significantly inhibit (e.g., delay, reduce, slow, and/or prevent) microbial growth in the composition for use in the methods of treatment, methods of administration, and dosage regimes described herein. Exemplary microbial agents and embodiments for the use of microbial agents are disclosed in U.S. Ser. No. 11/514,030, filed Aug. 30, 2006 (such as those described in paragraphs [0036] to [0058]). In some embodiments, the antimicrobial agent is a chelating agent, such as EDTA, edetate, citrate, pentetate, tromethamine, sorbate, ascorbate, derivatives thereof, or mixtures thereof In some embodiments, the antimicrobial agent is a polydentate chelating agent. In some embodiments, the antimicrobial agent is a non-chelating agent, such as any of sulfites, benzoic acid, benzyl alcohol, chlorobutanol, paraben, or derivatives thereof In some embodiments, an antimicrobial other than rapamycin or derivatives thereof discussed above is not contained or used in the methods of treatment, methods of administration, and dosage regimes described herein Sugar Containing Composition In some embodiments, the compositions of the invention include a sugar for use in the methods of treatment described herein. In some embodiments, the compositions of the invention include both a sugar and an antimicrobial agent for use in the methods of treatment described herein. Exemplary sugars and embodiments for the use of sugars are disclosed in U.S. Ser. No. 11/514,030, filed Aug. 30, 2006 (such as those described in paragraphs [0084] to [0090]). In some embodiments, the sugar serves as a reconstitution enhancer which causes a lyophilized composition to dissolve or suspend in water and/or aqueous solution more quickly than the lyophilized composition would dissolve without the sugar. In some embodiments, the composition is a liquid (e.g., aqueous) composition obtained by reconstituting or resuspending a dry composition. In some embodiments, the concentration of sugar in the composition is greater than about 50 mg/ml. In some embodiments, the sugar is in an amount that is effective to increase the stability of the rapamycin or derivative thereof in the composition as compared to a composition without the sugar. In some embodiments, the sugar is in an amount that is effective to improve filterability of the composition as compared to a composition without the sugar.

The sugar-containing compositions described herein may further comprise one or more antimicrobial agents, such as the antimicrobial agents described herein or in U.S. Ser. No. 11/514,030, filed Aug. 30, 2006. In addition to one or more sugars, other reconstitution enhancers (such as those described in U.S. Pat. App. Publication No. 2005/0152979, which is hereby incorporated by reference in its entirety) can also be added to the compositions. In some embodiments, a sugar is not contained or used in the methods of treatment, methods of administration, and dosage regimes described herein Stabilizing Agents in Composition In some embodiments, the compositions of the invention also include a stabilizing agent for use in the methods of treatment, methods of administration, and dosage regimes described herein. In some embodiments, the compositions of the invention include an antimicrobial agent and/or a sugar and/or a stabilizing agent for use in the methods of treatment, methods of administration, and dosage regimes described herein. Exemplary stabilizing agents and embodiments for the use of stabilizing agents are disclosed in U.S. Ser. No. 11/513,756, filed Aug. 30, 2006 (such as those described in paragraphs [0038] to [0083] and [0107] to [0114]). The present invention in one of its embodiments provides for compositions and methods of preparation of rapamycin which retain the desirable therapeutic effects and remain physically and/or chemically stable upon exposure to certain conditions such as prolonged storage, elevated temperature, or dilution for parenteral administration. The stabilizing agent includes, for example, chelating agents (e.g., citrate, malic acid, edetate, or pentetate), sodium pyrophosphate, and sodium gluconate. In one embodiment, the invention provides pharmaceutical formulations of rapamycin or a derivative thereof comprising citrate, sodium pyrophosphate, EDTA, sodium gluconate, citrate and sodium chloride, and/or a derivative thereof. In another embodiment, the invention provides a composition of rapamycin comprising a surfactant, wherein the rapamycin used for preparing the formulation is in an anhydrous form prior to being incorporated into the composition.

In some embodiments, a stabilizing agent is not contained or used in the methods of treatment, methods of administration, and dosage regimes described herein.

Pharmaceutical Compositions and Formulations

The compositions described herein may be used in the preparation of a formulation, such as a pharmaceutical formulation, by combining the nanoparticle composition(s) described with a pharmaceutical acceptable carrier, excipients, stabilizing agents or other agent, which are known in the art, for use in the methods of treatment, methods of administration, and dosage regimes described herein. In some embodiments, the pharmaceutical composition includes nanoparticles comprising rapamycin or a derivative thereof and a carrier protein (e.g., albumin). In some embodiments, the pharmaceutical composition includes a) nanoparticles comprising rapamycin or a derivative thereof and a carrier protein (e.g., albumin) and b) at least one other therapeutic agent. In some embodiments, the other therapeutic agent comprises a chemotherapeutic agent (such as any of the chemotherapeutic agents described herein). In some embodiments, the other therapeutic agent comprises a hormone therapeutic agent.

To increase stability by increasing the negative zeta potential of nanoparticles, certain negatively charged components may be added. Such negatively charged components include, but are not limited to bile salts, bile acids, glycocholic acid, cholic acid, chenodeoxycholic acid, taurocholic acid, glycochenodeoxycholic acid, taurochenodeoxycholic acid, litocholic acid, ursodeoxycholic acid, dehydrocholic acid, and others; phospholipids including lecithin (egg yolk) based phospholipids which include the following phosphatidylcholines: palmitoyloleoylphosphatidylcholine, palmitoyllinoleoylphosphatidylcholine, stearoyllinoleoylphosphatidylcholine, stearoyloleoylphosphatidylcholine, stearoylarachidoylphosphatidylcholine, and dipalmitoylphosphatidylcholine. Other phospholipids including L-α-dimyristoylphosphatidylcholine (DMPC), dioleoylphosphatidylcholine (DOPC), distearoylphosphatidylcholine (DSPC), hydrogenated soy phosphatidylcholine (HSPC), and other related compounds. Negatively charged surfactants or emulsifiers are also suitable as additives, e.g., sodium cholesteryl sulfate and the like.

In some embodiments, the composition is suitable for administration to a human. In some embodiments, the composition is suitable for administration to a mammal such as, in the veterinary context, domestic pets and agricultural animals. There are a wide variety of suitable formulations of the inventive composition (see, e.g., U.S. Pat. Nos. 5,916,596 and 6,096,331, which are hereby incorporated by reference in their entireties). The following formulations and methods are merely exemplary and are in no way limiting. Formulations suitable for oral administration can comprise (a) liquid solutions, such as an effective amount of the compound dissolved in diluents, such as water, saline, or orange juice, (b) capsules, sachets or tablets, each containing a predetermined amount of the active ingredient, as solids or granules, (c) suspensions in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The formulations can be presented in unit-dose or multi-dose sealed containers, such as ampules and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions can be prepared from sterile powders, granules, and tablets of the kind previously described. Injectable formulations are preferred.

Formulations suitable for aerosol administration comprise the inventive composition include aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

In some embodiments, the composition is formulated to have a pH in the range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (e.g., about 8). The composition can also be made to be isotonic with blood by the addition of a suitable tonicity modifier, such as glycerol.

The nanoparticles of this invention can be enclosed in a hard or soft capsule, can be compressed into tablets, or can be incorporated with beverages or food or otherwise incorporated into the diet. Capsules can be formulated by mixing the nanoparticles with an inert pharmaceutical diluent and inserting the mixture into a hard gelatin capsule of the appropriate size. If soft capsules are desired, a slurry of the nanoparticles with an acceptable vegetable oil, light petroleum or other inert oil can be encapsulated by machine into a gelatin capsule.

Also provided are unit dosage forms comprising the compositions and formulations described herein. These unit dosage forms can be stored in a suitable packaging in single or multiple unit dosages and may also be further sterilized and sealed. For example, the pharmaceutical composition (e.g., a dosage or unit dosage form of a pharmaceutical composition) may include (i) nanoparticles that comprise rapamycin or a derivative thereof and a carrier protein and (ii) a pharmaceutically acceptable carrier. In other examples, the pharmaceutical composition (e.g., a dosage or unit dosage form of a pharmaceutical composition includes a) nanoparticles comprising rapamycin or a derivative thereof and a carrier protein (e.g., albumin) and b) at least one other therapeutic agent. In some embodiments, the other therapeutic agent comprises a chemotherapeutic agent (such as any of the chemotherapeutic agents described herein). In some embodiments, the other therapeutic agent comprises a hormone therapeutic agent. In some embodiments, the pharmaceutical composition also includes one or more other compounds (or pharmaceutically acceptable salts thereof) that are useful for treating cancer. In various embodiments, the amount of rapamycin or a derivative thereof in the composition is included in any of the following ranges: about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, or about 300 to about 350 mg. In some embodiments, the amount of rapamycin or derivative thereof in the composition (e.g., a dosage or unit dosage form) is in the range of about 54 mg to about 540 mg, such as about 180 mg to about 270 mg or about 216 mg, of the rapamycin or derivative thereof. In some embodiments, the carrier is suitable for parental administration (e.g., intravenous administration). In some embodiments, a taxane is not contained in the composition. In some embodiments, the rapamycin or derivative thereof is the only pharmaceutically active agent for the treatment of cancer that is contained in the composition.

In some embodiments, the invention features a dosage form (e.g., a unit dosage form) for the treatment of cancer comprising (i) nanoparticles that comprise a carrier protein and rapamycin or a derivative thereof, wherein the amount of rapamycin or derivative thereof in the unit dosage from is in the range of about 180 mg to about 270 mg, and (ii) a pharmaceutically acceptable carrier. In some embodiments, the amount of the rapamycin or derivative thereof in the unit dosage form includes about 216 mg.

Also provided are articles of manufacture comprising the compositions, formulations, and unit dosages described herein in suitable packaging for use in the methods of treatment, methods of administration, and dosage regimes described herein. Suitable packaging for compositions described herein are known in the art, and include, for example, vials (such as sealed vials), vessels (such as sealed vessels), ampules, bottles, jars, flexible packaging (e.g., sealed Mylar or plastic bags), and the like. These articles of manufacture may further be sterilized and/or sealed.

Kits

The invention also provides kits comprising the compositions, formulations, unit dosages, and articles of manufacture described herein for use in the methods of treatment, methods of administration, and dosage regimes described herein. Kits of the invention include one or more containers comprising rapamycin or a derivative thereof-containing nanoparticle compositions (formulations or unit dosage forms and/or articles of manufacture), and in some embodiments, further comprise instructions for use in accordance with any of the methods of treatment described herein. In some embodiments, the kit further comprises at least one other therapeutic agent. In some embodiments, the other therapeutic agent comprises a chemotherapeutic agent (such as any of the chemotherapeutic agents described herein). In some embodiments, the other therapeutic agent comprises a hormone therapeutic agent. In some embodiments, the kit comprises i) a composition comprising nanoparticles comprising a rapamycin and a carrier protein (such as albumin) and ii) instructions for administering the nanoparticles and the chemotherapeutic agents simultaneously and/or sequentially, for treatment of cancer. In various embodiments, the cancer is early stage cancer, non-metastatic cancer, primary cancer, advanced cancer, stage IV cancer, locally advanced cancer, metastatic cancer, cancer in remission, recurrent cancer, cancer in an adjuvant setting, cancer in a neoadjuvant setting, or cancer substantially refractory to hormone treatment. In various embodiments, the amount of rapamycin or a derivative thereof in the kit is included in any of the following ranges: about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, or about 300 to about 350 mg. In some embodiments, the amount of rapamycin or a derivative thereof in the kit is in the range of about 54 mg to about 540 mg, such as about 180 mg to about 270 mg or about 216 mg. In some embodiments, the kit includes one or more other compounds (i.e., one or more compounds other than a taxane) that are useful for treating cancer. In some embodiments, the other compound is a chemotherapeutic agent. In some embodiments, the other compound is a hormone therapeutic.

Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of the nanoparticle compositions generally include information as to dosage, dosing schedule, and route of administration for the intended treatment. In some embodiments, the instructions comprise instructions for providing a first and second therapy, wherein either the first or second therapy comprises administering a composition that comprises nanoparticles of rapamycin or derivative thereof and a carrier protein. The kit may further comprise a description of selecting an individual suitable or treatment.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. In other embodiments, the kit of the invention comprises the packaging described above and a second packaging comprising a buffer. It may further include other materials desirable from a commercial and user standpoint, including other buffers, diluents, filters, needles, syringes, and package inserts with instructions for performing any methods described herein.

For combination therapies of the invention, the kit may contain instructions for administering the first and second therapies simultaneously and/or sequentially for the effective treatment of cancer. The first and second therapies can be present in separate containers or in a single container. It is understood that the kit may comprise one distinct composition or two or more compositions wherein one composition comprises a first therapy and one composition comprises a second therapy.

Kits may also be provided that contain sufficient dosages of rapamycin or a derivative thereof as disclosed herein to provide effective treatment for an individual for an extended period, such as any of a week, 2 weeks, 3 weeks, 4 weeks, 6 weeks, 8 weeks, 3 months, 4 months, 5 months, 6 months, 7 months, 8 months, 9 months or more. Kits may also include multiple unit doses of rapamycin or a derivative thereof compositions, pharmaceutical compositions, and formulations described herein and instructions for use and packaged in quantities sufficient for storage and use in pharmacies, for example, hospital pharmacies and compounding pharmacies. In some embodiments, the kit comprises a dry (e.g., lyophilized) composition that can be reconstituted, resuspended, or rehydrated to form generally a stable aqueous suspension of nanoparticles comprising rapamycin or a derivative thereof and albumin (e.g., rapamycin or a derivative thereof coated with albumin).

The kits of the invention are in suitable packaging. Suitable packaging include, but is not limited to, vials, bottles, jars, flexible packaging (e.g., seled Mylar or plastic bags), and the like. Kits may optionally provide additional components such as buffers and interpretative information.

Methods of Making the Compositions

Methods of making compositions containing carrier proteins and poorly water soluble pharmaceutical agents are known in the art. For example, nanoparticles containing poorly water soluble pharmaceutical agents and carrier proteins (e.g., albumin) can be prepared under conditions of high shear forces (e.g., sonication, high pressure homogenization, or the like). These methods are disclosed in, for example, U.S. Pat. Nos. 5,916,596; 6,506,405; and 6,537,579 and also in U.S. Pat. Pub. No. 2005/0004002A1, which are each hereby incorporated by reference in their entireties.

Briefly, the rapamycin or derivative hereof is dissolved in an organic solvent. Suitable organic solvents include, for example, ketones, esters, ethers, chlorinated solvents, and other solvents known in the art. For example, the organic solvent can be methylene chloride, chloroform/ethanol, or chloroform/t-butanol (for example with a ratio of about any of 1:9, 1:8, 1:7, 1:6, 1:5, 1:4, 1:3, 1:2, 1:1, 2:1, 3:1, 4:1, 5:1, 6:1, 7:1, 8:1, or 9:1 or with a ratio of about any of 3:7, 5:7, 4:6, 5:5, 6:5, 8:5, 9:5, 9.5:5, 5:3, 7:3, 6:4, or 9.5:0.5). The solution is added to a carrier protein (e.g., human serum albumin). The mixture is subjected to high pressure homogenization (e.g., using an Avestin, APV Gaulin, Microfluidizer™ such as a Microfluidizer™ Processor M-110EH from Microfluidics, Stansted, or Ultra Turrax homogenizer). The emulsion may be cycled through the high pressure homogenizer for between about 2 to about 100 cycles, such as about 5 to about 50 cycles or about 8 to about 20 cycles (e.g., about any of 8, 10, 12, 14, 16, 18 or 20 cycles). The organic solvent can then be removed by evaporation utilizing suitable equipment known for this purpose, including, but not limited to, rotary evaporators, falling film evaporators, wiped film evaporators, spray driers, and the like that can be operated in batch mode or in continuous operation. The solvent may be removed at reduced pressure (such as at about any of 25 mm Hg, 30 mm Hg, 40 mm Hg, 50 mm Hg, 100 mm Hg, 200 mm Hg, or 300 mm Hg). The amount of time used to remove the solvent under reduced pressure may be adjusted based on the volume of the formulation. For example, for a formulation produced on a 300 mL scale, the solvent can be removed at about 1 to about 300 mm Hg (e.g., about any of 5-100 mm Hg, 10-50 mm Hg, 20-40 mm Hg, or 25 mm Hg) for about 5 to about 60 minutes (e.g., about any of 7, 8, 9, 10, 11, 12, 13, 14, 15 16, 18, 20, 25, or 30 minutes).

If desired, human albumin solution may be added to the dispersion to adjust the human serum albumin to rapamycin ratio or to adjust the concentration of rapamycin in the dispersion. For example, human serum albumin solution (e.g., 25% w/v) can be added to adjust the human serum albumin to rapamycin ratio to about any of 18:1, 15,:1 14:1, 13:1, 12:1, 11:1, 10:1, 9:1, 8:1, 7.5:1, 7:1, 6:1, 5:1, 4:1, or 3:1. For example, human serum albumin solution (e.g., 25% w/v) or another solution is added to adjust the concentration of rapamycin in the dispersion to about any of 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 15 mg/ml, 20 mg/ml, 25 mg/ml, 30 mg/ml, 40 mg/ml, or 50 mg/ml. The dispersion may be serially filtered through multiple filters, such as a combination of 1.2 μm and 0.8/0.2 μm filters; the combination of 1.2 μm, 0.8 μm, 0.45 μm, and 0.22 μm filters; or the combination of any other filters known in the art. The dispersion obtained can be further lyophilized. The nanoparticle compositions may be made using a batch process or a continuous process (e.g., the production of a composition on a large scale).

If desired, a second therapy (e.g., one or more compounds useful for treating breast cancer), an antimicrobial agent, sugar, and/or stabilizing agent can also be included in the composition. This additional agent can either be admixed with the rapamycin and/or the carrier protein during preparation of the rapamycin/carrier protein composition, or added after the rapamycin/carrier protein composition is prepared. For example, the agent can be added along with an aqueous medium used to reconstitute/suspend the rapamycin/carrier protein composition or added to an aqueous suspension of the carrier protein-associated rapamycin. In some embodiments, the agent is admixed with the rapamycin/carrier protein composition prior to lyophilization. In some embodiments, the agent is added to the lyophilized pharmaceutical agent/carrier protein composition. In some embodiments when the addition of the agent changes the pH of the composition, the pH in the composition are generally (but not necessarily) adjusted to a desired pH. Exemplary pH values of the compositions include, for example, in the range of about 5 to about 8.5. In some embodiments, the pH of the composition is adjusted to no less than about 6, including for example no less than any of about 6.5, 7, or 8 (e.g., about 8).

The invention also provides methods of making the combination therapies described herein for use in the treatment of cancer. For example, there is provided a method of preparing a composition comprising rapamycin or a derivative thereof, a carrier protein (e.g., albumin), and a second therapy by combining (e.g., admixing) a composition containing rapamycin (or a derivative thereof) and a carrier protein with a second therapy (e.g., one or more other pharmaceutically active agents for the treatment of cancer). If desired, an antimicrobial agent, sugar, and/or stabilizing agent can also be included in the composition.

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

The specification is most thoroughly understood in light of the references cited herein. The disclosures of all publications, patents, patent applications, and published patent applications referred to herein are each hereby incorporated herein by reference in their entireties.

The following Examples are provided to illustrate, but not limit, the invention.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Exemplary Methods for the Formation of Nanoparticle Compositions with Rapamycin and Albumin

Example 1-A

This example demonstrates the preparation of a pharmaceutical composition comprising rapamycin and albumin in which the rapamycin concentration was 8 mg/mL in the emulsion and the formulation was made on a 300 mL scale. Rapamycin (2400 mg) was dissolved in 12 mL of chloroform/t-butanol. The solution was then added into 288 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (25 mm of Hg). The resulting dispersion was translucent. At this stage, human serum albumin solution was added to the dispersion to adjust the human serum albumin to rapamycin ratio. The dispersion was serially filtered through multiple filters. The size of the filtered formulation was 85-100 nm ($Z_{av}$, Malvern Zetasizer). The dispersion was further lyophilized (FTS Systems, Dura-Dry μP, Stone Ridge, N.Y.) for 60 hours. The resulting cake was easily reconstitutable to the original dispersion by the addition of sterile water or 0.9% (w/v) sterile saline. The particle size after reconstitution was the same as before lyophilization.

Example 1-B

This example demonstrates the preparation of a pharmaceutical composition comprising rapamycin and albumin in which the rapamycin concentration was 8.3 mg/mL in the emulsion and the formulation was made on a 200 mL scale. Rapamycin (1660 mg) was dissolved in 8.5 mL of chloroform/ethanol. The solution was then added into 191.5 mL of a human serum albumin solution (6% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (25 mm of Hg). The dispersion was serially filtered. The size of the 0.22 µm filtered formulation was 85 nm ($Z_{av}$, Malvern Zetasizer). The dispersion was further lyophilized (FTS Systems, Dura-Dry µP, Stone Ridge, N.Y.) for 60 hours. The resulting cake was easily reconstitutable to the original dispersion by addition of 0.9% (w/v) sterile saline. The particle size after reconstitution was the same as before lyophilization.

Example 1-C

This example demonstrates the preparation of a pharmaceutical composition comprising rapamycin and albumin in which the rapamycin concentration was 16.2 mg/mL in the emulsion and the formulation was made on a 200 mL scale. Rapamycin (3240 mg) was dissolved in 16 mL of chloroform/ethanol. The solution was then added into 184 mL of a human serum albumin solution (6% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (25 mm of Hg). At this stage, human serum albumin solution was added to the dispersion and the volume of the dispersion was made to 400 mL to adjust the human serum albumin to rapamycin ratio and to adjust the rapamycin concentration. The dispersion was serially filtered. The size of the 0.22 µm filtered formulation was 99 nm ($Z_{av}$, Malvern Zetasizer). The dispersion was further lyophilized (FTS Systems, Dura-Dry µP, Stone Ridge, N.Y.) for 60 hours. The resulting cake was easily reconstitutable to the original dispersion by addition of 0.9% (w/v) sterile saline. The particle size after reconstitution was the same as before lyophilization.

Example 1-D

This example demonstrates the preparation of a pharmaceutical composition comprising rapamycin and albumin in which the rapamycin concentration was 8.2 mg/mL in the emulsion and the formulation was made on a 40 mL scale. Rapamycin (328 mg) was dissolved in 1.8 mL of chloroform/ethanol. The solution was then added into 38.2 mL of a human serum albumin solution (6% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 108 nm ($Z_{av}$, Malvern Zetasizer). The liquid suspension was found to be stable at 4° C. and 25° C. at least for 48 hours.

Example 1-E

This example demonstrates the preparation of a pharmaceutical composition comprising rapamycin and albumin in which the rapamycin concentration was 8.5 mg/mL in the emulsion and the formulation was made on a 30 mL scale. Rapamycin (255 mg) was dissolved in 1.35 mL of chloroform/ethanol. The solution was then added into 28.7 mL of a human serum albumin solution (6% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 136 nm ($Z_{av}$, Malvern Zetasizer). The liquid suspension was found to be stable at 4° C. and 25° C. at least for 24 hours.

Example 1-F

This example demonstrates the preparation of a pharmaceutical composition comprising rapamycin and albumin in which the rapamycin concentration was 9.2 mg/mL in the emulsion and the formulation was made on a 20 mL scale. Rapamycin (184 mg) was dissolved in 1.0 mL of chloroform/ethanol. The solution was then added into 19.0 mL of a human serum albumin solution (7% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 124 nm ($Z_{av}$, Malvern Zetasizer). The liquid suspension was found to be stable at 4° C. and 25° C. at least for 24 hours.

Example 1-G

This example demonstrates the preparation of a pharmaceutical composition comprising rapamycin and albumin in which the rapamycin concentration was 8.4 mg/mL in the emulsion and the formulation was made on a 20 mL scale. Rapamycin (168 mg) was dissolved in 1.2 mL of chloroform/ethanol. The solution was then added into 18.8 mL of a human serum albumin solution (6% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 95 nm ($Z_{av}$, Malvern Zetasizer).

Example 1-H

This example demonstrates the preparation of a pharmaceutical composition comprising rapamycin and albumin in which the rapamycin concentration was 8.2 mg/mL in the emulsion and the formulation was made on a 20 mL scale. Rapamycin (164 mg) was dissolved in 0.9 mL of chloroform/ethanol. The solution was then added into 19.1 mL of a human serum albumin solution (8% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 149 nm ($Z_{av}$, Malvern Zetasizer).

Example 1-I

This example demonstrates the preparation of a pharmaceutical composition comprising rapamycin and albumin in which the rapamycin concentration was 6.6 mg/mL in the emulsion and the formulation was made on a 20 mL scale. Rapamycin (132 mg) was dissolved in 0.8 mL of chloroform/ethanol. The solution was then added into 19.2 mL of a human serum albumin solution (5% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 129 nm ($Z_{av}$, Malvern Zetasizer).

Example 1-J

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 108 nm ($Z_{av}$, Malvern Zetasizer).

Example 1-K

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (1% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 99 nm ($Z_{av}$, Malvern Zetasizer).

Example 1-L

This example demonstrates the preparation of a pharmaceutical composition comprising rapamycin and albumin in which the rapamycin concentration was 5.0 mg/mL in the emulsion and the formulation was made on a 20 mL scale. Rapamycin (100 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 146 nm ($Z_{av}$, Malvern Zetasizer).

Example 1-M

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The resulting dispersion was a white milky suspension. The dispersion was serially filtered. The size of the 0.22 μm filtered formulation was 129 nm ($Z_{av}$, Malvern Zetasizer).

Example 1-N

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 μm filtered formulation was 166 nm ($Z_{av}$, Malvern Zetasizer).

Example 1-O

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 90 nm ($Z_{av}$, Malvern Zetasizer).

Example 1-P

This example demonstrates the preparation of a pharmaceutical composition comprising rapamycin and albumin in which the rapamycin concentration was 4.0 mg/mL in the emulsion and the formulation was made on a 20 mL scale. Rapamycin (80 mg) was dissolved in 0.8 mL of chloroform/ethanol. The solution was then added into 19.2 mL of a human serum albumin solution (3% w/v). The mixture was homogenized for 5 minutes at 10,000 rpm (Vitris homogenizer model Tempest I.Q.) in order to form a crude emulsion, and then transferred into a high pressure homogenizer. The emulsification was performed at 20,000 psi while recycling the emulsion. The resulting system was transferred into a Rotavap, and the solvent was rapidly removed at 40° C. at reduced pressure (40 mm of Hg). The dispersion was serially filtered. The size of the 0.22 µm filtered formulation was 81 nm ($Z_{av}$, Malvern Zetasizer).

Example 1-Q

This example demonstrates the preparation of a pharmaceutical composition comprising rapamycin and albumin. Rapamycin (30 mg) was dissolved in 2 ml chloroform/ethanol. The solution was then added into 27.0 ml of a human serum albumin solution (3% w/v). The mixture was homogenized for 5 minutes at low RPM (Vitris homogenizer model Tempest I.Q.) in order to form a crude emulsion, and then transferred into a high pressure homogenizer. The emulsification was performed at 9000-40,000 psi while recycling the emulsion for at least 5 cycles. The resulting system was transferred into a Rotavap, and the solvent was rapidly removed at 40° C. at reduced pressure (30 mm Hg) for 20-30 minutes. The resulting dispersion was translucent, and the typical average diameter of the resulting particles was in the range 50-220 nm (Z-average, Malvern Zetasizer). The dispersion was further lyophilized for 48 hours. The resulting cake was easily reconstituted to the original dispersion by addition of sterile water or saline. The particle size after reconstitution was the same as before lyophilization.

If desired, other compositions of the invention (e.g., compositions that contain rapamycin derivatives or carrier proteins other than human serum albumin) can be made using these methods or a variation of these methods. It should be recognized that the amounts, types, and proportions of drug, solvents, and proteins used in these examples are not limiting in any way.

Example 2A

Toxicology and Pharmacokinetic Studies of Nab-rapamycin

The overall toxicity of Nab-rapamycin was determined in a dose ranging study in Sprague Dawley rats. The dose levels of Nab-rapamycin used were 0, 15, 30, 45, 90 and 180 mg/kg with a q4dx3 schedule. The pharmacokinetics of Nab-rapamycin was also investigated in Sprague Dawley rats at dose levels of 1 (N=3), 15 (N=4), 30 (N=3), and 45 mg/kg (N=4). Blood samples were collected prior to dosing (baseline) and post-dosing at the following time points: 1, 5, 10, 15, 30 and 45 minutes, and 1, 4, 8, 24, 36 and 48 hours. Plasma samples were analyzed for rapamycin using LC/MS.

Nab-rapamycin was nontoxic at the highest dose of 180 mg/kg on a q4dx3 schedule. No changes in blood chemistry or CBC were observed. No hypercholesterolemia and hypertriglyceridemia were observed. As illustrated in FIGS. 1 and 2C, Nab-rapamycin exhibited linear pharmacokinetics with respect to dose and rapid extravascular distribution as demonstrated by large Vss and Vz. The Cmax and AUCinf of Nab-rapamycin were dose proportional (FIGS. 2A and 2B, respectively).

If desired, other compositions of the invention (e.g., compositions that contain rapamycin derivatives or carrier proteins other than human serum albumin) can be tested in these assays for toxicity and pharmacokinetics.

Example 2B

Toxicology and Pharmacokinetic Studies of Nab-rapamycin

The overall toxicity of Nab-rapamycin was determined in a dose ranging study in Sprague Dawley rats. Nab-rapamycin was intravenously administered at 0, 20, 40, 90, 120, and 180 mg/kg on a q4dx3 schedule on days 1, 5, and 9 (n=20). Nab-rapamycin was well tolerated at dose levels up to 90 mg/kg (540 mg/m$^2$) on a q4dx3 schedule. There was 20% and 100% mortality among the highest doses of 120 mg/kg and 180 mg/kg. No hypercholesterolemia and hypertriglyceridemia were observed.

The pharmacokinetics of Nab-rapamycin was also investigated in Sprague Dawley rats at dose levels of 1 (N=5), 15 (N=4), 30 (N=3), and 45 mg/kg (N=4). Blood samples were collected prior to dosing (baseline) and post-dosing at the following time points: 1, 5, 10, 15, 30 and 45 minutes, and 1, 4, 8, 24, 36 and 48 hours. Plasma samples were analyzed for rapamycin using LC/MS.

Nab-rapamycin exhibited a very rapid distribution phase and large $V_Z$ and $V_{SS}$. The $C_{max}$ and $AUC_{inf}$ of Nab-rapamycin were dose proportional. See FIG. 1. The PK of Nab-rapamyin is similar to Nab-paclitaxel and Nab-docetaxel. FIG. 2D shows the log-linear plot Nab-rapamycin blood concentration vs. time following IV administration to rats at dose levels of 15 mg/kg, 30 mg/kg, and 45 mg/kg.

Example 3

Inhibition of Breast Cancer Cells Using Nab-rapamycin

The antitumor activity of Nab-rapamycin was examined using a human mammary carcinoma xenograft in mice. MX-1 tumors were implanted subcutaneously into both the right and left flanks of female athymic mice (4-5 per group) and allowed to grow to 100 mm$^3$. The mice were then intravenously administered either saline or Nab-rapamycin at a dose level of 40 mg/kg with a three times weekly schedule for 4 weeks. The dosing volume was 2 ml/kg. Tumor growth data were analyzed by ANOVA.

Nab-rapamycin was highly effective against breast cancer, achieving a tumor growth inhibition of 88% against the MX-1 xenograft (p<0.0001 versus control, ANOVA; FIG. 3A). No significant weight loss was observed in the mice from Nab-rapamycin at 40 mg/kg (FIG. 3B). Thus, Nab-rapamycin was well tolerated even at the highest dose of 180 mg/kg with a q4dx3 schedule, showed linear pharmacokinetics, and was highly effective against a breast cancer model in vivo.

If desired, other compositions of the invention (e.g., compositions that contain rapamycin derivatives or carrier proteins other than human serum albumin) can be tested in this animal model to determine their ability to treat breast cancer in vivo.

Example 4

Use of Human Clinical Trials to Determine the Ability of Compositions of the Invention to Treat, Stabilize, Prevent, and/or Delay Cancer If desired, any of the compositions described herein can also be tested in humans to determine the ability of the compositions to treat, stabilize, prevent and/or delay cancer (e.g., breast cancer). Standard methods can be used for these clinical trials.

In one exemplary method, subjects (e.g., healthy subjects, subjects with cancer such as breast cancer, or subjects at increased risk for cancer such as breast cancer) are enrolled in a tolerability, pharmacokinetics, and pharmacodynamics phase I study of Nab-rapamycin or a derivative thereof using standard protocols. For example, escalating doses of rapamycin or a derivative thereof up to about 250 mg/m$^2$ as part of a composition of the invention can be tested. Then a phase II, double-blind randomized controlled trial is performed to determine the efficacy of the Nab-rapamycin or a derivative thereof. If desired, the activity of Nab-rapamycin or a derivative thereof can be compared to that of another treatment for cancer (e.g., breast cancer). Alternatively or additionally, the efficacy of a combination of Nab-rapamycin or a derivative thereof and another treatment for cancer (e.g., breast cancer) can be compared to that of either treatment alone.

Example 5

Multiple Myeloma (MM) Cell Lines for Use in Determination of Nab-rapamycin Activity Interleukin-6 (IL-6) and insulin like growth factor-1 (IGF-1) play a key role in the growth, survival, and drug resistance in multiple myeloma (MM) cells. Furthermore, their secretion in bone marrow stromal cells (BMSCs) is up-regulated by adherence of MM cells. IL-6 and IGF-1 mediate growth of MM cells via activation of the mitogen-activated protein kinase (MAPK) and phosphatidylinositol 3'-kinase/Akt kinase (PI3-K/Akt) signaling cascades. Several studies show that PI3-K/Akt signaling mediates growth, survival, migration and cell cycle regulation in MM. Activated Akt in turn phosphorylates downstream target molecules, including forkhead transcription factor (FKHR), glycogen synthase kinase (GSK)-3β, and mammalian target of rapamycin (mTOR).

MM cell lines can be used in standard cell-based assays to test the ability of any of the nanoparticle compositions of the invention (e.g., nanoparticles comprising rapamycin and a carrier protein such as albumin) to treat MM. The nanoparticle compositions of the invention are desirable because they may allow rapamycin to be delivered at higher doses with improved efficacy.

For these cell-based assays, RPMI 8226 and U266 human MM cell lines are obtained from the American Type Culture Collection (ATCC) of Rockville, Md. Patient derived MM cells are purified from patient BM samples, as described by Y. T. Tai, G. Teoh, Y. Shima, et al., J. Immunol. Methods 235:11, 2000. Human MM cell lines are cultured in RPMI-1640 media (Sigma Chemical, St. Louis, Mo.), containing 10% fetal bovine serum (FBS), 2 mmol/L L-glutamine (L-glut, GIBCO, Grand Island, N.Y.), 100 U/mL penicillin and 100 mg/mL streptomycin (P/S, GIBCO). MM patient cells are 95% CD38+, CD45RA−. Bone marrow stromal cells (BM-SCs) are prepared from aspirates of MM patients as well as healthy donors as described by D. Gupta, S. Treon, Y. Shima, et al. in Leukemia, 2001 and S. Gartner and H. S. Kaplan in Proc. Nag. Acad. Sci. USA 77:4756, 1980. Cells are cultured in ISCOVE's modified Dulbecco media containing 20% FBS, 2 mmol/L L-glut, and 100 µg/mL P/S. Human umbilical vein endothelial cells (HUVEC P168) are purchased from Clonetics, Biowhittaker, and maintained in EGM-2MV media (Clonetics, Biowhittaker). The nanoparticles comprising rapamycin and a carrier protein (such as albumin) are diluted in culture medium to concentrations ranging, e.g., from 0.01 to 100 µM.

Example 6

Panel of Drug-Resistant MM Cell Lines and Primary MM Tumor Cells for Use in Determination of Nab-rapamycin Activity Effectiveness of the nanoparticle compositions of the invention may further be evaluated in drug resistant cell lines. The use of drug resistant cells facilitates the determination of potential cancer patient subpopulations that may be effectively treated by the use of the nanoparticle compositions of the invention. The activity of any of the nanoparticle compositions of the invention (e.g., nanoparticles comprising rapamycin and a carrier protein such as albumin) can be evaluated in a panel of drug-sensitive and drug-resistant human MM cell lines using standard methods. Exemplary cell lines include a dexamethasone (Dex)-sensitive MM-1S cell line, a Dex-resistant MM-1R cell line; the chemo-sensitive parental MM cell line RPMI-8226/S, and its chemo-resistant sublines RPMI-8226/Dox40 (doxorubicin-resistant), RPMI-8226/MR20 (mitoxantrone-resistant), and RPMI-8226/LR5 (melphalan-resistant) cells; MM-1S-TR15 is a TRAIL/Apo2L-resistant subline; MM-SAR-1 (also referred to as MM-SA-1) cells that are primary MM tumor cells from a patient resistant to the proteasome inhibitor bortezomib (PS-341) (cells maintained in vitro resistance to PS-341);OCI-My-5 cells; S6B45 cells; ARD; ARK; ARP-1; OPM-1; OPM-6; K620; LP-1; U266; and NCI-H929 cells. All cells are cultured in RPMI 1640 medium (Life Technologies, Grand Island, N.Y.) supplemented with 10% fetal bovine serum, L-glutamine, penicillin, and streptomycin (Life Technologies).

Primary MM tumor cells additionally may be isolated from bone marrow (BM) aspirates of patients, who are resistant to conventional (steroid- and cytotoxic chemotherapy-based) and more recently developed anti-MM agents (e.g. thalidomide or proteasome inhibitors). The resistant primary MM tumor cells are collected from patients as described above in Example 4.

Example 7

Co-Culture Assays of MM Cells with Bone Marrow Stromal Cells (BMSCs) Treated with Nab-rapamycin When adhering to BMSCs, MM cells have reduced sensitivity to conventional anti-MM therapies, such as dexamethasone or cytotoxic chemotherapeutics (Chauhan D. et al., *Blood*. 1996, 87, 1104-1112). This form of drug resistance is considered a key reason why MM patients eventually relapse when they receive treatment based on administration of glucocorticoids and/or cytotoxic chemotherapy. Therefore, any of the nanoparticle compositions of the invention (e.g., nanoparticles comprising rapamycin and a carrier protein such as albumin) can be tested to determine whether they overcome the molecular sequelae of the interaction of BMSCs with MM cells and achieve anti-MM activity in this context. In particular, an in vitro co-culture assay is performed using MM cells with BMSCs as previously described. BMSCs are grown on 24-well plates to confluency. Following washings with serum-free medium, primary tumor cells (greater than about 95% purity in CD138+ cells) isolated from MM patients are added to BMSC-coated or control wells as described previously (Uchiyama H. et al., *Blood* 1993, 82, 3712-3720; Mitsiades N. et al., *Blood* 2003, 101, 4055-4062) and incubated for 48 hours in the presence or absence of a nanoparticle composition of the invention, such as nab-rapamycin. Flow cytometric analysis is performed to detect the CD138+ population of viable MM cells and the effect of the nanoparticle composition on MM cell viability is expressed as a percent of viable cells in comparison to the respective vehicle-treated cultures.

Example 8

MTT Calorimetric Survival Assay of MM Tissue Culture Cells Treated with Nab-rapamycin In this example, the effect of nanoparticle composition of the invention (e.g., nanoparticles comprising rapamycin and a carrier protein such as albumin) on cell viability and survival is assessed. Cell survival is examined using a 3-(4,5-dimethylthiazol-2-yl)-2,5-diphenyltetrazolium bromide (MTT; Sigma Chemical, St Louis, Mo.) colorimetric assay, as previously described (Mitsiades C. S. et al., *Blood* 2001, 98, 795-804; Mitsiades N. et al., *PNAS* 2002, 99, 14374-14379; Mitsiades N. et al., *Blood* 2003, 101, 2377-2380). Briefly, cells are plated in 48-well plates at 70% to 80% confluence in the presence of 2.5% fetal bovine serum (FBS) and in the presence of a nanoparticle composition of the invention (e.g., nanoparticles comprising rapamycin and a carrier protein such as albumin) at final concentration of 0-100 nM rapamycin or DMSO vehicle control. At the end of each treatment, cells are incubated with 1 mg/mL MTT for 4 hours at 37° C. A mixture of isopropanol and 1 N HCl (23:2, vol/vol) is then added under vigorous pipetting to dissolve the formazan crystals. Dye absorbance (A) in viable cells is measured at 570 nm, with 630 nm as a reference wavelength. Cell viability is estimated as a percentage of the value of untreated controls. Experiments are typically repeated at least 3 times, and each experimental condition is typically repeated at least in triplicate wells in each experiment. Data is reported are average values+/−SD of representative experiments.

Example 9

Proliferation of MM Cells Treated with Nab-rapamycin

In this example, the effect of nanoparticle composition of the invention (e.g., nanoparticles comprising rapamycin and a carrier protein such as albumin) on cell proliferation and viability is assessed. For proliferation and cell viability assays, MM cells are first starved for 12 hours in RPMI-1640 media containing 10% fetal bovine serum, and then plated into 96-well microtiter plates (Costar, Cambridge, Mass.), in the presence of a nanoparticle composition of the invention (e.g., nanoparticles comprising rapamycin and a carrier protein such as albumin) or DMSO control. Proliferation is measured by the incorporation of $^3$H-thymidine (NEN Products, Boston, Mass.). Specifically, cells are pulsed with $^3$H-thymidine (0.5 .muck/well) for the last 6 hours of 48 hour cultures, harvested onto glass filters with an automatic cell harvester (Cambridge Technology, Cambridge, Mass.), and counted using a LKB Betaplate scintillation counter (Wallac, Gaithersburg, Md.). Measurement of cell viability is performed colorimetrically using a MTS assay, utilizing the CellTiter96 One Solution Reagent (Promega, Madison, Wis.). Cells are exposed to the MTS for the last 2 hours of 48 hour cultures, and absorbance is measured using an ELISA plate reader (Molecular Devices Corp., Sunnyvale, Calif.) at OD of 570 nm.

Example 10

Cell Cycle Analysis of MM Tissue Culture Cells Treated with Nab-rapamycin

In this example, the effect of nanoparticle composition of the invention (e.g., nanoparticles comprising rapamycin and a carrier protein such as albumin) on cell cycle is assessed. MM cells (1×106 cells) are cultured in the presence of a nanoparticle composition of the invention (e.g., nanoparticles comprising rapamycin and a carrier protein such as albumin) or DMSO control for 24, 48 and 72 hours. Cells are then washed with phosphate buffered saline (PBS), fixed with 70% ethanol, and treated with RNAse (Sigma). Cells are next stained with propidium iodide (PI, 5 µg/mL), and the cell cycle profile is determined using the M software on an Epics flow cytometer (Coulter Immunology, Hialeah, Fla.).

Example 11

Other MM Cell Activity Assays for Cells Treated with Nab-rapamycin

Nanoparticle composition of the invention (e.g., nanoparticles comprising rapamycin and a carrier protein such as albumin) can be further assessed by other activity assays known in the art. For example, the molecular mechanisms of anti-MM activities of nanoparticle composition of the invention may be assessed using, but not limited to, cell cycle profiling by caspases/PARP cleavage and quantification of anti-apoptotic proteins by Western blotting.

Example 12A

Effect of Nab-rapamycin on Human MM Cells in vivo

In this example, the effect of nanoparticle composition of the invention (e.g., nanoparticles comprising rapamycin and a carrier protein such as albumin) on MM cell growth in vivo is assessed. Mice are inoculated subcutaneously into the right flank with 3×107 MM cells in 100 mL of RPMI 1640, together with 100 µL matrigel basement membrane matrix (Becton Dickinson, Bedford, Mass.). On day 6 post injection, mice are assigned into two treatment groups receiving a nanoparticle composition of the invention (e.g., nanoparticles comprising rapamycin and a carrier protein such as albumin) or into a control group. Treatment with a nanoparticle composition of the invention is then intravenously administered either saline or nanoparticles comprising rapamycin and a carrier protein such as albumin at a dose level of 40 mg/kg with a three times weekly schedule for 4 weeks. The dosing volume is 2 ml/kg. Caliper measurements of the longest perpendicular tumor diameters are performed twice per week to estimate the tumor volume. Animals are sacrificed when their tumor reached 2 cm or when the mice become moribund. Survival is evaluated from the first day of tumor injection until death.

Example 12B

Effect of Nab-rapamycin on Human MM1S Cells in vivo

Figure 7:
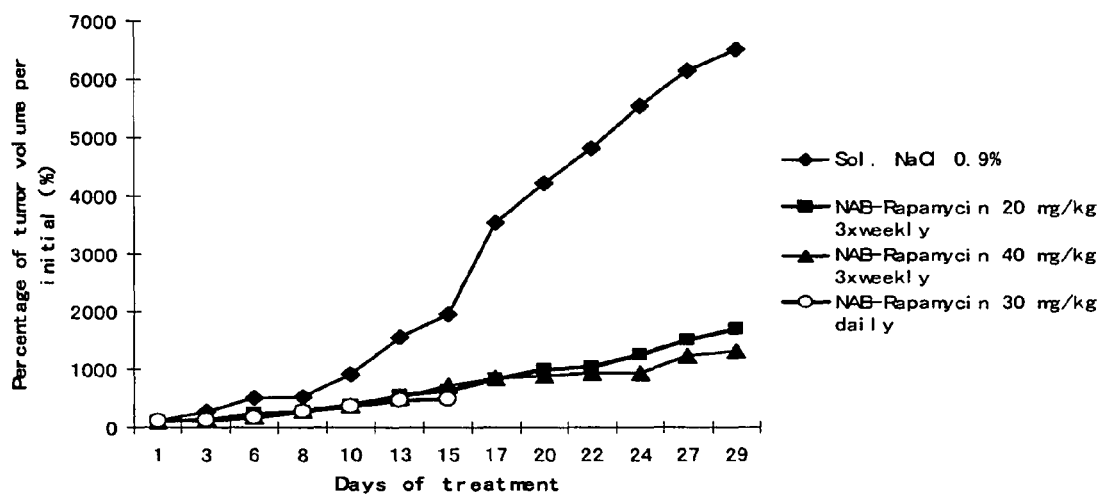
FIG. 7 is a graph showing the antitumor activity of Nab-rapamycin in mice with MM1S multiple myeloma tumor xenografts.

In this example, the effect of Nab-rapamycin on MM cell growth in vivo was assessed. Mice were inoculated subcutaneously into the right flank with $3 \times 10^7$ MM1S cells in 100 mL of RPMI 1640, together with 100 μL matrigel basement membrane matrix (Becton Dickinson, Bedford, Mass.). On day 6 post injection, mice were assigned into three treatment groups receiving Nab-rapamycin or into a control group. Animals in the control group were administered with 0.9% NaCl solution (i.v.). Animals in the three treatment groups were administered with Nab-rapamycin at a dose schedule of 20 or 40 mg/kg three times weekly or at a dose schedule of 30 mg/kg daily for 15 days. The dosing volume was 2 ml/kg. Caliper measurements of the longest perpendicular tumor diameters were performed twice per week to estimate the tumor volume. Animals were sacrificed when their tumor reached 2 cm or when the mice became moribund. As shown in FIG. 7, in all three treatment groups, Nab-rapamycin was highly effective against multiple myeloma.

Example 13

Figure 4:
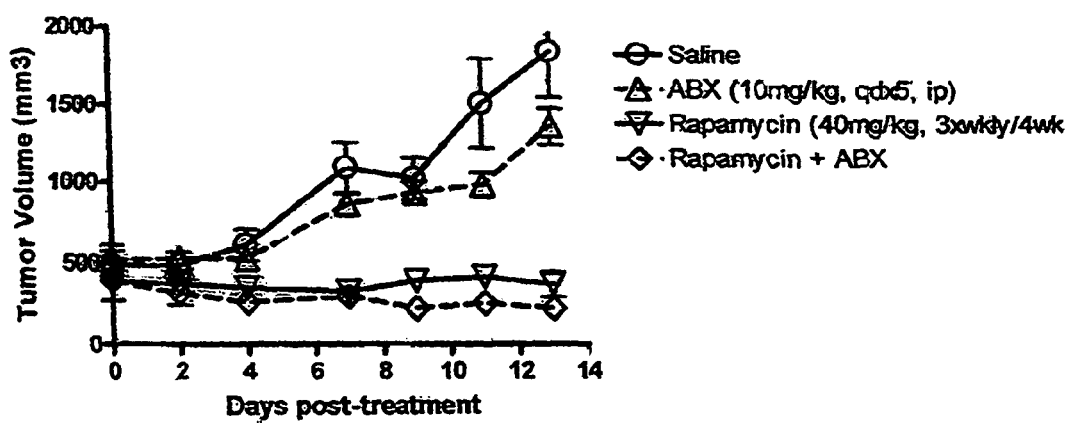
FIG. 4 is a graph showing the antitumor activity of Abraxane™, Nab-rapamycin, and Nab-rapamycin in combination with Abraxane™ in mice with HT29 colon tumor xenografts.

Cytotoxic Activity of Nab-rapamycin in Combination with Abraxane™ Against HT29 (Human Colon Carcinoma) Tumor Xenograft The following example is disclosed in U.S. Ser. No. 11/359,286, which was filed Feb. 21, 2006 (i.e., U.S. Pat. Pub. No. 2006/0263434, published Nov. 23, 2006). Nude mice were implanted with $10^6$ HT29 cells on their right flanks. Treatment was initiated once the tumors were palpable and were greater than 100-200 mm³. The mice were randomly sorted into 4 groups (n=8 per group). Group 1 received saline 3 times weekly for 4 weeks, i.v.; Group 2 received Abraxane™ at 10 mg/kg, daily for 5 days, i.p.; Group 3 received Nab-rapamycin at 40 mg/kg, 3 times weekly for 4 weeks, i.v.; and Group 4 received both Nab-rapamycin (40 mg/kg, 3 times weekly for 4 weeks, i.v.) and Abraxane™ (10 mg/kg, daily for 5 days, i.p.). As shown in FIG. 4, the tumor suppression was greater for the Abraxane™ plus Nab-rapamycin combination therapy than for either single therapy group.

Example 14

Cytotoxic Activity of Nab-rapamycin Against HT29 (Human Colon Carcinoma) Tumor Xenograft The antitumor activity of Nab-rapamycin was examined using HT29 human colon carcinoma xenograft in mice. Male athymic mice (3 per group) were implanted with $10^6$ HT29 cells on their right flanks and allowed to grow to ~100 mm³. The mice were then intravenously administered with either DMSO at 2 mL/kg or Nab-rapamycin at a dose level of 40 mg/kg with a three times weekly schedule for 4 weeks at a dosing volume of 5 mL/kg. Tumor growth data were analyzed by ANOVA.

Figures 5A, 5B:
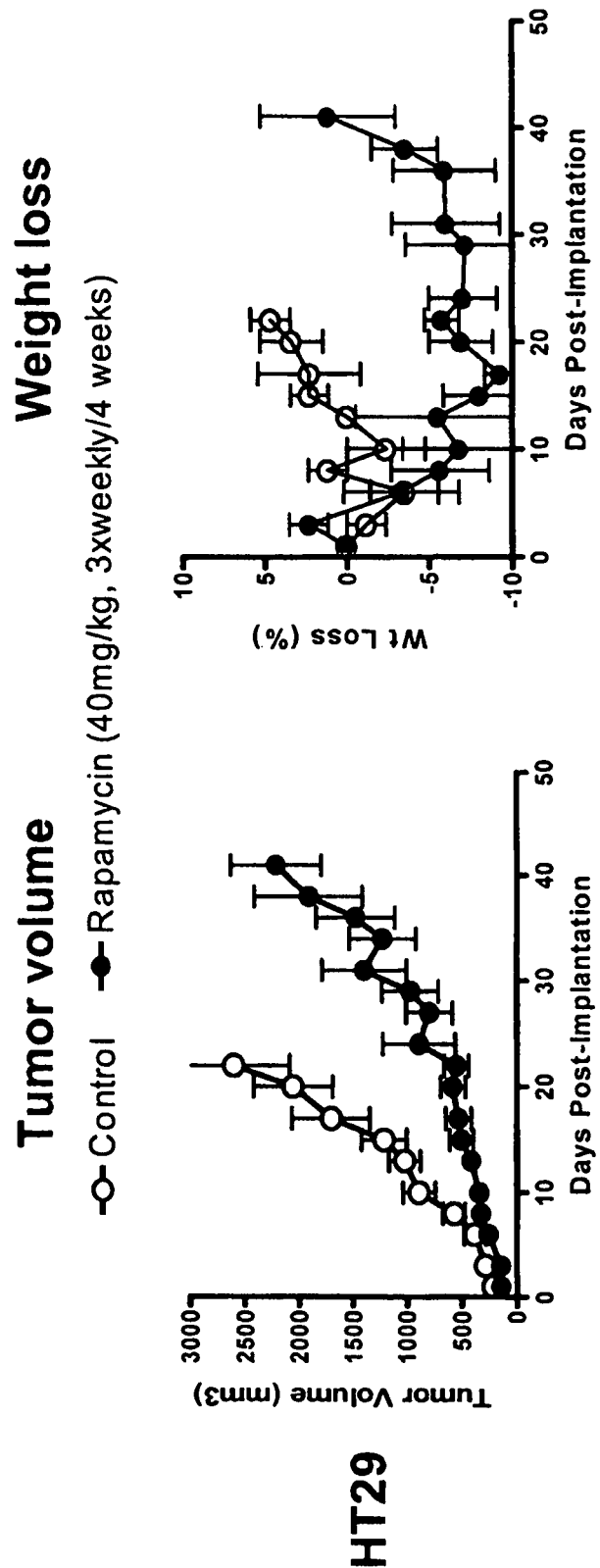
FIG. 5A is a graph showing the antitumor activity of Nab-rapamycin in mice with HT29 colon tumor xenografts.
FIG. 5B is a graph showing the weight loss in mice with H29 colon tumor xenografts after the administration of Nab-rapamycin or DMSO.

Nab-rapamycin significantly inhibited in vivo tumor growth for HT29 tumors, achieving a tumor growth inhibition of 78.9% against the HT29 tumor xenograft (p=0.005 versus control, ANOVA; FIG. 5A). A −9.2% weight loss was observed in the mice from Nab-rapamycin at 40 mg/kg (FIG. 5B).

Example 15

Cytotoxic Activity of Nab-rapamycin Against HCT-116 (Human Colon Carcinoma) Tumor Xenograft The antitumor activity of Nab-rapamycin was examined using HCT-116 human colon carcinoma xenograft in mice. HCT-116 tumors were implanted subcutaneously into the right flanks of male athymic nude mice (10 per group) and allowed to grow to 100-221 mm³. The mice were then intravenously administered with either saline or Nab-rapamycin at a dose level of 40 mg/kg with a three times weekly schedule for 4 weeks at a dosing volume of 10 mL/kg. Tumor growth data were analyzed by ANOVA.

Figures 6A, 6B:
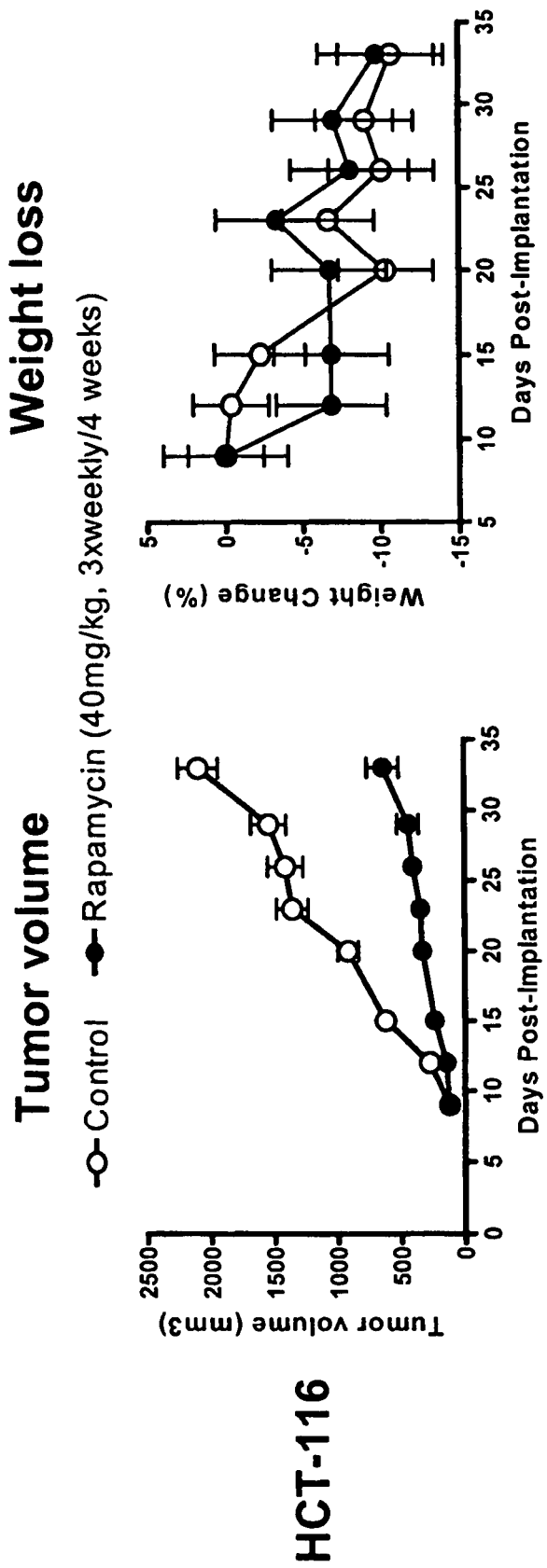
FIG. 6A is a graph showing the antitumor activity of Nab-rapamycin in mice with HCT-116 colon tumor xenografts.
FIG. 6B is a graph showing the weight loss in mice with HCT-116 colon tumor xenografts after the administration of Nab-rapamycin or saline.

Nab-rapamycin significantly inhibited in vivo tumor growth for HCT-116 tumors, achieving a tumor growth inhibition of 71% against the HCT-116 tumor xenograft (p<0.0001 versus control, ANOVA; FIG. 6A). A −9.7% weight loss was observed in the mice from Nab-rapamycin at 40 mg/kg, which is similar to the −10.7% weight loss for the control group (FIG. 6B).

What is claimed is:

1. A method of treating cancer in a human individual, comprising administering to an individual an effective amount of a composition comprising nanoparticles that comprise rapamycin or a derivative thereof and albumin, wherein the rapamycin or derivative thereof is coated with albumin, wherein the amount of the rapamycin or derivative thereof in the effective amount of the composition is in the range of about 54 mg to about 180 mg, and wherein the average diameter of the nanoparticle in the capsule is no greater than about 200 nm.

2. The method of claim 1, wherein the cancer is a plasmacytoma.

3. The method of claim 1, wherein the cancer is selected from the group consisting of multiple myeloma, pancreatic cancer, brain cancer, prostate cancer, lung cancer, melanoma, and breast cancer.

4. The method of claim 1, wherein the cancer is bladder cancer, renal cell carcinoma, mesothelioma, or neuroendocrine cancer.

5. The method of claim 4, wherein the cancer is bladder cancer.

6. The method of claim 1, wherein the albumin is human serum albumin.

7. A unit dosage form for treatment of cancer in a human individual comprising (a) nanoparticles that comprise rapamycin or a derivative thereof and albumin, wherein the rapamycin or derivative thereof is coated with albumin, wherein the amount of the rapamycin or derivative thereof in the unit dosage form is in the range of about 54 mg to about 180 mg, and (b) a pharmaceutically acceptable carrier, and wherein the average diameter of the nanoparticles in the composition is no greater than about 200 nm.

8. A kit comprising (a) nanoparticles that comprise rapamycin or a derivative thereof and albumin, wherein the rapamycin or derivative thereof is coated with albumin, wherein the amount of the rapamycin or derivative thereof in the kit is in the range of about 54 mg to about 180 mg, and (b) instructions for using the kit in treating cancer in a human individual, wherein the average diameter of the nanoparticles in the composition is no greater than about 200 nm.

9. A method of treating cancer in a human individual comprising (a) a first therapy comprising administering to an individual an effective amount of a composition comprising nanoparticles that comprise rapamycin or a derivative thereof and albumin, where the rapamycin or derivative thereof is coated with albumin and (b) a second therapy selected from second therapy selected from the group consisting of chemotherapy, radiation therapy, surgery, hormone therapy, gene therapy, bone marrow transplantation, stem cell transplantation, targeted therapy, cryotherapy, ultrasound therapy, and immunotherapy, wherein the amount of the rapamycin or derivative thereof in the effective amount of the composition is in the range of about 54 mg to about 180 mg, wherein the average diameter of the nanoparticles in the composition is no greater than about 200 nm.

10. The method of claim 9, wherein the second therapy is chemotherapy.

11. The method of claim 10, wherein chemotherapy comprises administration of a chemotherapeutic selected from the group consisting of antimetabolite agents, platinum-based agents, alkylating agents, tyrosine kinase inhibitors, anthracycline antibiotics, vinca alkloids, proteasome inhibitors, and topoisomerase inhibitors.

12. The method of claim 9, wherein the cancer is selected from the group consisting of multiple myeloma, pancreatic cancer, prostate cancer, lung cancer, melanoma, and breast cancer.

13. The method of claim 9, wherein the cancer is bladder cancer, renal cell carcinoma, mesothelioma, or neuroendocrine cancer.

14. The method of claim 9, wherein the first therapy and the second therapy are conducted sequentially.

15. The method of claim 9, wherein the albumin is human serum albumin.

16. The method of claim 10, wherein the chemotherapy comprises administering to the individual an inhibitor of the mTOR signaling pathway.

17. The method of claim 10, wherein the chemotherapy comprises administering to the individual an AKT kinase inhibitor.

18. The method of claim 17, wherein AKT kinase inhibitor is perifosine.

19. The method of claim 10, wherein the chemotherapy comprises administering to the individual a tyrosine kinase inhibitor.

20. The method of claim 19, wherein the tyrosine kinase inhibitor is erlotinib.

21. The method of claim 1, wherein the composition is administered via an intravenous, intraarterial, intraperitoneal, intravesicular, subcutaneous, or intrathecal route.

22. The method of claim 9, wherein the composition is administered via an intravenous, intraarterial, intraperitoneal, intravesicular, subcutaneous, or intrathecal route.

23. The method of claim 1, wherein the composition comprises nanoparticles comprising rapamycin.

24. The method of claim 23, wherein the composition comprises nanoparticles comprising rapamycin and human serum albumin.

25. The method of claim 9, wherein the composition comprises nanoparticles comprising rapamycin.

26. The method of claim 25, wherein the composition comprises nanoparticles comprising rapamycin and human serum albumin.

27. The method of claim 23, wherein the cancer is bladder cancer, renal cell carcinoma, mesothelioma, or neuroendocrine cancer.

28. The method of claim 27, wherein the cancer is bladder cancer.

29. The method of claim 24, wherein the cancer is bladder cancer, renal cell carcinoma, mesothelioma, or neuroendocrine cancer.

30. The method of claim 29, wherein the cancer is bladder cancer.

31. The method of claim 25, wherein the cancer is bladder cancer, renal cell carcinoma, mesothelioma, or neuroendocrine cancer.

32. The method of claim 31, wherein the cancer is bladder cancer.

33. The method of claim 25, wherein the cancer is bladder cancer, renal cell carcinoma, mesothelioma, or neuroendocrine cancer.

34. The method of claim 33, wherein the cancer is bladder cancer.

35. The method of claim 1, wherein the amount of the rapamycin or derivative thereof in the effective amount of the composition is in the range of about 75 mg to about 100 mg.

36. The method of claim 4, wherein the amount of the rapamycin or derivative thereof in the effective amount of the composition is in the range of about 75 mg to about 100 mg.

37. The method of claim 23, wherein the amount of the rapamycin or derivative thereof in the effective amount of the composition is in the range of about 75 mg to about 100 mg.

* * * * *